US010537633B2

(12) United States Patent
Tso et al.

(10) Patent No.: US 10,537,633 B2
(45) Date of Patent: Jan. 21, 2020

(54) ANTIBODIES TO TIGIT

(71) Applicants: JN Biosciences LLC, Mountain View, CA (US); Abmuno Therapeutics LLC, Berkeley, CA (US)

(72) Inventors: J. Yun Tso, Menlo Park, CA (US); Naoya Tsurushita, Palo Alto, CA (US); Omar Duramad, Berkeley, CA (US)

(73) Assignees: JN Biosciences LLC, Mountain View, CA (US); Abmuno Therapeutics LLC, Berkeley, CA (US)

( * ) Notice: Subject to any disclaimer, the term of this patent is extended or adjusted under 35 U.S.C. 154(b) by 0 days.

(21) Appl. No.: 15/449,665

(22) Filed: Mar. 3, 2017

(65) Prior Publication Data

US 2017/0281764 A1  Oct. 5, 2017

Related U.S. Application Data

(60) Provisional application No. 62/413,025, filed on Oct. 26, 2016, provisional application No. 62/304,045, filed on Mar. 4, 2016.

(51) Int. Cl.
*C07K 16/28* (2006.01)
*C07K 16/46* (2006.01)
*A61K 39/395* (2006.01)
*C07K 16/30* (2006.01)
*A61K 39/00* (2006.01)

(52) U.S. Cl.
CPC .... *A61K 39/39541* (2013.01); *A61K 39/3955* (2013.01); *C07K 16/2803* (2013.01); *C07K 16/2809* (2013.01); *C07K 16/2878* (2013.01); *C07K 16/2896* (2013.01); *C07K 16/3061* (2013.01); *A61K 2039/507* (2013.01); *A61K 2121/00* (2013.01); *C07K 2317/30* (2013.01); *C07K 2317/33* (2013.01); *C07K 2317/70* (2013.01); *C07K 2317/76* (2013.01); *C07K 2317/90* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 7,354,584 B2 * | 4/2008 | Reed | C07K 16/244 424/133.1 |
| 7,473,423 B2 | 1/2009 | Rodriguez et al. | |
| 7,736,647 B2 | 6/2010 | Boumsell et al. | |
| 8,163,279 B2 | 4/2012 | Bergstein | |
| 8,183,346 B2 | 5/2012 | Leung et al. | |
| 8,409,573 B2 | 4/2013 | Boumsell et al. | |
| 8,410,251 B2 | 4/2013 | Matsuura et al. | |
| 8,580,714 B2 | 11/2013 | Almagro et al. | |
| 8,715,941 B2 | 5/2014 | Abo et al. | |
| 8,858,949 B2 | 10/2014 | Yokoseki et al. | |
| 8,859,501 B2 | 10/2014 | Nodström et al. | |
| 8,962,804 B2 | 2/2015 | Williams et al. | |
| 9,127,061 B2 | 9/2015 | Zhang et al. | |
| 9,243,070 B2 | 1/2016 | Bansal | |
| 9,499,596 B2 | 11/2016 | Clark et al. | |
| 2004/0005560 A1 | 1/2004 | Isogai et al. | |
| 2004/0213791 A1* | 10/2004 | Bander | A61K 51/1072 424/155.1 |
| 2008/0032304 A1 | 2/2008 | Isogai et al. | |
| 2009/0258013 A1* | 10/2009 | Clark | C07K 16/18 424/133.1 |
| 2011/0150903 A1 | 6/2011 | Baurin et al. | |
| 2012/0082667 A1 | 4/2012 | Yokoseki et al. | |
| 2013/0216476 A1 | 8/2013 | Boumsell | |
| 2015/0166661 A1 | 6/2015 | Chen et al. | |
| 2015/0203579 A1 | 7/2015 | Papadopoulos et al. | |
| 2015/0203580 A1 | 7/2015 | Papadopoulos et al. | |
| 2015/0210769 A1 | 7/2015 | Freeman et al. | |
| 2015/0216970 A1 | 8/2015 | Grogan et al. | |
| 2015/0218274 A1 | 8/2015 | Sabatos-Peyton et al. | |
| 2015/0259420 A1 | 9/2015 | Triebel et al. | |
| 2015/0307617 A1 | 10/2015 | Du et al. | |
| 2015/0322119 A1 | 11/2015 | Engelhardt et al. | |
| 2016/0115234 A1 | 4/2016 | Salas et al. | |
| 2016/0115467 A1 | 4/2016 | Salas | |
| 2016/0176963 A1 | 6/2016 | Maurer et al. | |

FOREIGN PATENT DOCUMENTS

| | | |
|---|---|---|
| FR | 2 959 416 A1 | 11/2011 |
| FR | 2 959 416 B1 | 11/2011 |
| JP | 2006-311857 A | 11/2006 |
| WO | WO-94/29457 A2 | 12/1994 |
| WO | WO-94/29457 A3 | 12/1994 |
| WO | WO-97/43416 A1 | 11/1997 |
| WO | WO-03/072035 A2 | 9/2003 |
| WO | WO-03/072035 A8 | 9/2003 |
| WO | WO-2004/024068 A2 | 3/2004 |
| WO | WO-2004/024068 A3 | 3/2004 |
| WO | WO-2006/124667 A2 | 11/2006 |
| WO | WO-2006/124667 A3 | 11/2006 |
| WO | WO-2007/124283 A2 | 11/2007 |
| WO | WO-2007/124283 A3 | 11/2007 |

(Continued)

OTHER PUBLICATIONS

Rudikoff et al. (Proceedings of the National Academy of Sciences USA, vol. 79, p. 1979-1983, 1982) (Year: 1982).*

(Continued)

*Primary Examiner* — Michael Allen
(74) *Attorney, Agent, or Firm* — Mintz Levin Cohn Ferris Glovsky and Popeo P.C.

(57) ABSTRACT

The invention provides monoclonal antibodies that specifically bind to TIGIT. The monoclonal antibodies have the capacity for substantial activation of T cells and natural killer cells by inhibiting binding of TIGIT to CD155. The monoclonal antibodies can be used for treatment of cancer and infectious disease, among other applications.

9 Claims, 34 Drawing Sheets
Specification includes a Sequence Listing.

(56) References Cited

FOREIGN PATENT DOCUMENTS

| | | |
|---|---|---|
| WO | WO-2008/092992 A1 | 8/2008 |
| WO | WO-2008/092993 A1 | 8/2008 |
| WO | WO-2009/064944 A2 | 5/2009 |
| WO | WO-2009/064944 A3 | 5/2009 |
| WO | WO-2009/073163 A1 | 6/2009 |
| WO | WO-2009/126688 A2 | 10/2009 |
| WO | WO-2009/126688 A3 | 10/2009 |
| WO | WO-2009/126688 A8 | 10/2009 |
| WO | WO 2010/119704 A1 | 10/2010 |
| WO | WO-2011/156356 A1 | 12/2011 |
| WO | WO-2012/008494 A1 | 1/2012 |
| WO | WO-2012/021834 A1 | 2/2012 |
| WO | WO-2012/058588 A2 | 5/2012 |
| WO | WO-2012/058588 A3 | 5/2012 |
| WO | WO-2012/078793 A2 | 6/2012 |
| WO | WO-2012/078793 A3 | 6/2012 |
| WO | WO-2012/078813 A2 | 6/2012 |
| WO | WO-2012/078813 A3 | 6/2012 |
| WO | WO-2012/122396 A1 | 9/2012 |
| WO | WO-2012/129227 A1 | 9/2012 |
| WO | WO-2012/135132 A1 | 10/2012 |
| WO | WO-2013/125636 A1 | 8/2013 |
| WO | WO-2013/125654 A1 | 8/2013 |
| WO | WO-2013/126810 A1 | 8/2013 |
| WO | WO-2013/147169 A1 | 10/2013 |
| WO | WO 2013/147176 A1 | 10/2013 |
| WO | WO-2013/150623 A1 | 10/2013 |
| WO | WO-2013/172961 A1 | 11/2013 |
| WO | WO-2013/184912 A2 | 12/2013 |
| WO | WO-2013/184912 A3 | 12/2013 |
| WO | WO-2013/184912 A4 | 12/2013 |
| WO | WO-2014/089169 A2 | 6/2014 |
| WO | WO-2014/089169 A3 | 6/2014 |
| WO | WO-2014/089169 A4 | 6/2014 |
| WO | WO-2014/189973 A2 | 11/2014 |
| WO | WO-2014/189973 A3 | 11/2014 |
| WO | WO-2015/045447 A1 | 4/2015 |
| WO | WO-2015/099838 A2 | 7/2015 |
| WO | WO-2015/099838 A3 | 7/2015 |
| WO | WO-2015/133882 A1 | 9/2015 |
| WO | WO-2016/011264 A1 | 1/2016 |
| WO | WO-2016/022883 A1 | 2/2016 |
| WO | WO-2016/028656 A1 | 2/2016 |
| WO | WO-2016/073282 A1 | 5/2016 |
| WO | WO-2016/081640 A1 | 5/2016 |
| WO | WO-2016/081643 A1 | 5/2016 |
| WO | WO2016/191643 | * 12/2016 |
| WO | WO-2016/191643 A2 | 12/2016 |
| WO | WO-2016/191643 A3 | 12/2016 |
| WO | WO-2016/191643 A4 | 12/2016 |

OTHER PUBLICATIONS

Paul (Fundamental Immunology, 3rd Edition, 1993, pp. 292-295) (Year: 1993).*
Bendig M. M. (Methods: a Companion to Methods in Enzymology, 1995; 8:83-93) (Year: 1995).*
Harris (Biotechnology, vol. 11, Pg. 1293-1297, 1993) (Year: 1993).*
Anderson, A.C. et al. (May 17, 2016). "Lag-3, Tim-3, and TIGIT: Co-inhibitory Receptors with Specialized Functions in Immune Regulation," *Immunity* 44(5):989-1004.
Bruck, C. et al. (Sep. 1986). "Nucleic acid sequence of an internal image-bearing monoclonal anti-idiotype and its comparison to the sequence of the external antigen," *PNAS USA* 83(17):6578-6582.
GenBank Accession No. NP_0776160.2, Nov. 15, 2015, 3 pages.
Hampe, C.S. et al. (Jul. 2005). "Quantitative evaluation of a monoclonal antibody and its fragment as potential markers for pancreatic beta cell mass," *Exp Clin Endocrinol Diabetes* 113(7):381-387.
International Search Report dated Jul. 7, 2017, for PCT Application No. PCT/US2017/20719, filed Mar. 3, 2017, 5 pages.
Kofler, R. et al. (Jan. 1987). "Molecular analysis of the murine lupus-associated anti-self response: involvement of a large number of heavy and light chain variable region genes," *Eur J Immunol* 17(1):91-95.
Leahy, D.J. et al. (Jun. 1988). "Sequences of 12 monoclonal anti-dinitrophenyl spin-label antibodies for NMR studies," *PNAS USA* 85(11):3661-3665.
Li, S. et al. (Mar. 17, 2009, e-published Mar. 3, 2009). "Efalizumab binding to the LFA-1 alphaL I domain blocks ICAM-1 binding via steric hindrance," *PNAS USA* 106(11):4349-4354.
GenBank Accession No. AAB49890.1, Jan. 30, 1997, 2 pages.
Pennell, C.A. et al. (Sep. 1, 1990). "High frequency expression of S107 VH genes by peritoneal B cells of B10.H-2aH-4bP/WTS mice," *J Immunol* 145(5):1592-1597.
Stark, S.E. et al. (Sep. 1, 1991). "Antibodies that are specific for a single amino acid interchange in a protein epitope use structurally distinct variable regions," *J Exp Med* 174(3):613-624.
Stengel, K.F. et al. (Apr. 3, 2012, e-published Mar. 15, 2012). "Structure of TIGIT immunoreceptor bound to poliovirus receptor reveals a cell-cell adhesion and signaling mechanism that requires cis-trans receptor clustering," *PNAS USA* 109(14):5399-5404.
Written Opinion dated Jul. 7, 2017, for PCT Application No. PCT/US2017/20719, filed Mar. 3, 2017, 12 pages.
Extended European Search Report dated Sep. 25, 2019, for EP Patent Application No. 17760920.3, 8 pages.
Stanietsky, N. et al. (Oct. 20, 2009, e-published Oct. 7, 2009). "The interaction of TIGIT with PVR and PVRL2 inhibits human NK cell cytotoxicity," PNAS USA 106(42):17858-17863.

* cited by examiner

FIG. 3

TIG1 VH

```
         1          2          3
123456789 0123456789 0123456789 0123456789
DVQLVESGG GLVQPGGSRK LSCAASGFTF SNFGMHWVRQ
                                   CDR1

4          5           6          7
0123456789 0122345678  0123456789 0123456789
              a
APEKGLEWVA FISSGSSSIYY ADTVKGRFTI SRDNPKNTLF
           CDR2

1          1
8             9           0          1
0122223456789 0123456789  000123456789 0123
   abc                       ab
LQMTSLRSEDTAM YYCARMRLDY  YAMDYWGQGTSV TVSS (SEQ ID NO: 10)
                 CDR3
```

FIG. 4

TIG1 VL

```
          1          2          3
123456789 0123456789 0123456789 0123456789
DVQITQSPS YLAASPGETI TINCRASKSI SKYLAWYQEK
                          CDR1

4         5          6          7
0123456789 0123456789 0123456789 0123456789
PGKTNKLLIY SGSTLQSGIP SRFSGSGSGT DFTLTISSLE
           CDR2

1
8          9          0
0123456789 0123456789 01234567
PEDFAMYYCQ QHNEYPWTFG GGTKLEIK (SEQ ID NO: 14)
           CDR3
```

FIG. 5

TIG2 VH

```
         1          2          3
123456789 0123456789 0123456789 0123456789
EVQLQQSGP ELVKPGASVK ISCKTSGYTF TEYTMHWVKQ
                                     CDR1

4          5           6          7
0123456789 01223456789 0123456789 0123456789
                a
SHGKNLEWIG GINPNNGGTSY NQKFKGRATL TVDKSSTAY
                CDR2

1          1
8            9           0          1
0122223456789 0123456789 000123456789 0123
    abc                     ab
MELRSLTSDDSAV YYCARPGWYN YAMDYWGQGTSV TVSS (SEQ ID NO: 18)
                    CDR3
```

FIG. 6

TIG2 VL

```
         1          2          3
123456789 0123456789 0123456789 0123456789
DIVMTQSHK FMSTSVGDRV NITCKASQGV STAVAWYQQK
                              CDR1

4          5          6          7
0123456789 0123456789 0123456789 0123456789
PGQSPKLLIY SASYRYTGVP DRFTGSGSGT DFTFTISSVQ
              CDR2

1
8          9          0
0123456789 0123456789 01234567
AEDLAVYHCQ QHYITPWTFG GGTKLEIK  (SEQ ID NO: 22)
              CDR3
```

FIG. 7

TIG3 VH

```
              1          2          3
123456789  0123456789  0123456789  0123456789
EVQLVESGG  GLVKPGGSLK  LSCAASGFAF  SDYDMSWVRQ
                                    CDR1

4           5           6           7
0123456789  01223456789 0123456789  0123456789
             a
TPEKRLEWVA  YISDGGYNTYY PDTVKGRFTI  SRDNAKNTLY
             CDR2

1           1
8            9            0           1
0122223456789 0123456789 000123456789 0123
   abc                      ab
LQMSSLKSEDTAI YYCARQILLR YYFDYWGQGTTL TVSS (SEQ ID NO: 26)
               CDR3
```

FIG. 8

TIG3 VL

```
         1          2                3
123456789 0123456789 0123456777777789 0123456789
                         abcdef
DIVMSQSPS SLAVSVGEKV TMTCKSSQSLLYSSNQ KNYLAWYQQK
                         CDR1

4         5          6          7
0123456789 0123456789 0123456789 0123456789
PGQSPKLLIY WASTRESGVP DRFTGSGSGT DFTLTISSVK
             CDR2

1
8          9          0
0123456789 0123456789 01234567
AEDLAVYYCQ QYHSYPWTFG GGTKLEIK  (SEQ ID NO: 30)
             CDR3
```

FIG. 9A

HuTIG1 VH gene

```
ACTAGTACCACCATGGACTCCAGGCTCAATCTGGTTTTCCTTGTCCTTATTCTGAAAGGC
             M  D  S  R  L  N  L  V  F  L  V  L  I  L  K  G

GTCCAGTGTGAAGTGCAGCTGGTGGAGTCTGGGGGAGGCCTGGTGCAGCCTGGAGGGTCC
 V  Q  C  E  V  Q  L  V  E  S  G  G  G  L  V  Q  P  G  G  S

CTGAGACTCTCCTGTGCAGCCTCTGGATTCACTTTCAGTAACTTTGGAATGCACTGGGTT
 L  R  L  S  C  A  A  S  G  F  T  F  S  N  F  G  M  H  W  V

CGACAGGCTCCAGGGAAGGGGCTGGAGTGGGTCGCATTCATTAGTAGTGGCAGTAGTTCC
 R  Q  A  P  G  K  G  L  E  W  V  A  F  I  S  S  G  S  S  S

ATCTACTATGCAGACACAGTGAAGGGCCGATTCACCATCTCCAGAGACAATGCCAAGAAC
 I  Y  Y  A  D  T  V  K  G  R  F  T  I  S  R  D  N  A  K  N

AGCCTGTACCTGCAAATGAACAGTCTGAGGGCTGAGGACACTGCCGTGTATTACTGTGCA
 S  L  Y  L  Q  M  N  S  L  R  A  E  D  T  A  V  Y  Y  C  A

AGAATGAGACTGGATTACTATGCTATGGACTACTGGGGTCAAGGAACCATGGTCACCGTC
 R  M  R  L  D  Y  Y  A  M  D  Y  W  G  Q  G  T  M  V  T  V

TCCTCAGGTAAGTATGGCCTCTAAGCTT (SEQ ID NO:38)
 S  S (SEQ ID NO:34)
```

FIG. 9B

HuTIG1 VL gene

GCTAGCACCACCATGAGGTTCCAGGTTCAGGTTCTGGGGCTCCTTCTGCTCTGGATCTCA
          M  R  F  Q  V  Q  V  L  G  L  L  L  L  W  I  S

GGAGCCCAGTGTGATATCCAGATGACCCAGTCTCCATCTTCTCTTTCTGCATCTGTTGGA
 G  A  Q  C  D  I  Q  M  T  Q  S  P  S  S  L  S  A  S  V  G

GATAGAGTCACTATTACTTGCAGGGCAAGTAAGAGCATTAGCAAATATCTGGCCTGGTAT
 D  R  V  T  I  T  C  R  A  S  K  S  I  S  K  Y  L  A  W  Y

CAACAGAAACCTGGGAAAGCTCCTAAGCTGCTTATCTACTCTGGGTCCACTTTGCAATCT
 Q  Q  K  P  G  K  A  P  K  L  L  I  Y  S  G  S  T  L  Q  S

GGAGTTCCATCAAGATTCAGTGGCAGTGGATCTGGTACAGATTTCACTCTCACCATCAGT
 G  V  P  S  R  F  S  G  S  G  S  G  T  D  F  T  L  T  I  S

AGCCTGCAGCCTGAAGATTTTGCAACCTATTACTGTCAACAGCATAATGAATACCCCTGG
 S  L  Q  P  E  D  F  A  T  Y  Y  C  Q  Q  H  N  E  Y  P  W

ACCTTCGGCGGAGGCACCAAAGTCGAAATCAAACGTAAGTAGAATCCAAAGAATTC (SEQ ID NO:39)
 T  F  G  G  G  T  K  V  E  I  K  (SEQ ID NO:36)

FIG. 14A

HuTIG3 VH gene

```
ACTAGTACCACCATGAACTTTGGGCTCAGATTGATTTTCCTTGTCCTTACTCTGAAAGGC
          M  N  F  G  L  R  L  I  F  L  V  L  T  L  K  G

GTGAACTGTGAAGTCCAGCTCGTGGAGTCTGGGGGAGGCCTTGTGCAGCCTGGAGGGTCC
 V  N  C  E  V  Q  L  V  E  S  G  G  G  L  V  Q  P  G  G  S

CTGAGACTCTCCTGTGCAGCCTCTGGATTCGCTTTCAGTGACTATGACATGTCTTGGGTT
  L  R  L  S  C  A  A  S  G  F  A  F  S  D  Y  D  M  S  W  V

CGCCAGGCTCCTGGCAAGGGGCTGGAGTGGGTCGCATACATTAGTGATGGCGGTTATAAC
  R  Q  A  P  G  K  G  L  E  W  V  A  Y  I  S  D  G  G  Y  N

ACCTACTATCCAGACACTGTGAAGGGCCGATTCACCATCTCCAGAGACAATGCCAAGAAC
  T  Y  Y  P  D  T  V  K  G  R  F  T  I  S  R  D  N  A  K  N

TCCCTGTACCTGCAAATGAACAGTCTGAGGGCTGAGGACACAGCCGTCTATTACTGTGCA
  S  L  Y  L  Q  M  N  S  L  R  A  E  D  T  A  V  Y  Y  C  A

AGACAAATTCTGCTGCGGTACTACTTTGACTACTGGGGCCAAGGCACCACTGTCACAGTC
  R  Q  I  L  L  R  Y  Y  F  D  Y  W  G  Q  G  T  T  V  T  V

TCCTCAGGTGAGTCCTTAAAACAAGCTT (SEQ ID NO:46)
  S  S  (SEQ ID NO:42)
```

FIG. 14B

HuTIG3 VL gene

```
GCTAGCACCACCATGGATTCACAGGCCCAGGTTCTTATGCTGCTGCTGCTCTGGGTTTCT
          M   D   S   Q   A   Q   V   L   M   L   L   L   W   V   S

GGAACCTGTGGGGACATTCAGATGACACAGTCTCCATCCTCCCTGTCTGCCTCAGTTGGA
  G   T   C   G   D   I   Q   M   T   Q   S   P   S   S   L   S   A   S   V   G

GACAGGGTTACTATCACCTGCAAGTCCAGTCAGAGTCTTCTGTATAGTAGCAATCAAAAG
  D   R   V   T   I   T   C   K   S   S   Q   S   L   L   Y   S   S   N   Q   K

AACTACTTGGCCTGGTACCAGCAGAAACCAGGGAAGGCTCCTAAACTGCTGATTTACTGG
  N   Y   L   A   W   Y   Q   Q   K   P   G   K   A   P   K   L   L   I   Y   W

GCATCCACTAGGGAATCTGGGGTCCCTAGTCGCTTCTCAGGCAGTGGATCTGGGACAGAT
  A   S   T   R   E   S   G   V   P   S   R   F   S   G   S   G   S   G   T   D

TTCACTCTCACCATCAGCAGTCTGCAGCCTGAAGACTTCGCAGTTTATTACTGTCAGCAA
  F   T   L   T   I   S   S   L   Q   P   E   D   F   A   V   Y   Y   C   Q   Q

TATCATAGCTATCCCTGGACCTTCGGCGGAGGCACCAAGGTGGAAATCAAACGTAAGTAG
  Y   H   S   Y   P   W   T   F   G   G   G   T   K   V   E   I   K  (SEQ ID NO:44)

AATCCAAAGAATTC  (SEQ ID NO:47)
```

Increased CD4+ & CD8+ T cell proliferation by TIG1 to Antigen-Specific Recall Stimulation.

FIG. 18
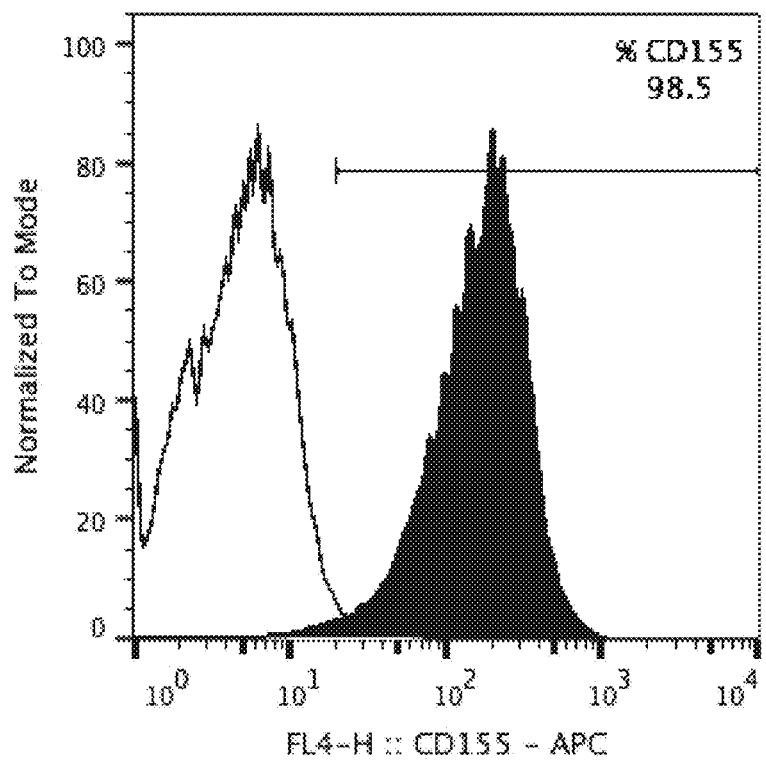
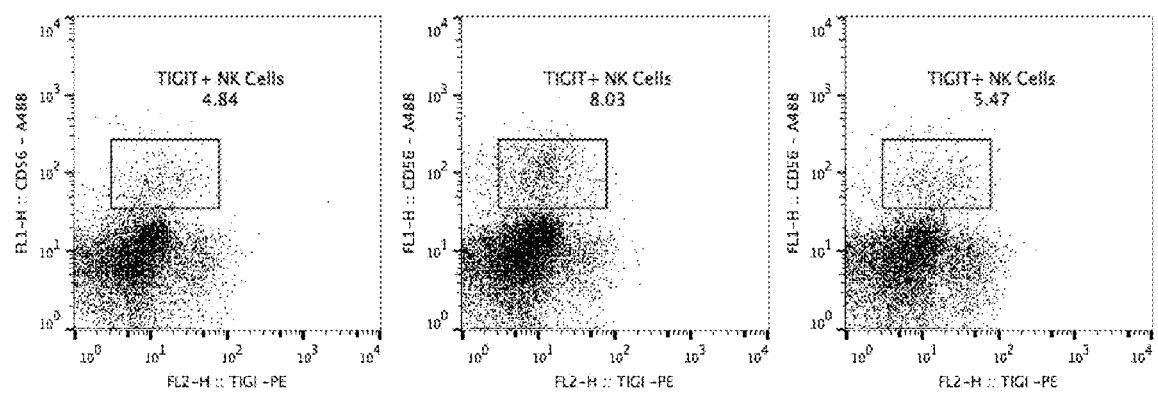

Enhanced NK cell mediated cytotoxicity by TIG1 on K562 Target Cells.

HuTIG1-IgG1.AA Potentiates Cytokine Effector Responses.

HuTIG1-IgG1.AA & HuTIG3-IgG1.AA do not elicit CDC Activity.

*In vitro* T-cell Antagonistic Activity Assay for Anti-human TIGIT Antibodies.

Expression
Level

| | | Cell Surface Markers | HuTIG1 |
|---|---|---|---|
| Melanoma | T cells | TCRβ⁺ CD4⁺ CD25⁻ | +/- |
| | | TCRβ⁺ CD4⁺ CD25⁺ | ++++ |
| | | TCRβ⁺ CD8⁺ | ++++ |
| | Antigen Presenting Cells | CD11b⁺ CD14⁺ HLA-DR⁺ | |
| | | CD11b⁻ CD14⁻ HLA-DR⁺ | |
| Colorectal Cancer | T cells | TCRβ⁺ CD4⁺ CD25⁻ | +/- |
| | | TCRβ⁺ CD4⁺ CD25⁺ | ++++ |
| | | TCRβ⁺ CD8⁺ | ++++ |
| | Antigen Presenting Cells | CD11b⁻ CD14⁺ HLA-DR⁺ | |
| | | CD11b⁻ CD14⁻ HLA-DR⁺ | |
| Non Small Cell Lung Carcinoma | T cells | TCRβ⁺ CD4⁺ CD25⁻ | +/- |
| | | TCRβ⁺ CD4⁺ CD25⁺ | ++++ |
| | | TCRβ⁺ CD8⁺ | ++++ |
| | Antigen Presenting Cells | CD11b⁺ CD14⁺ HLA-DR⁺ | |
| | | CD11b⁻ CD14⁻ HLA-DR⁺ | |
| Renal Clear Cell Carcinoma | T cells | TCRβ⁺ CD4⁺ CD25⁻ | +/- |
| | | TCRβ⁺ CD4⁺ CD25⁺ | ++++ |
| | | TCRβ⁺ CD8⁺ | ++++ |
| | Antigen Presenting Cells | CD11b⁻ CD14⁺ HLA-DR⁺ | |
| | | CD11b⁻ CD14⁻ HLA-DR⁺ | |

FIG. 32B

Expression Level

— 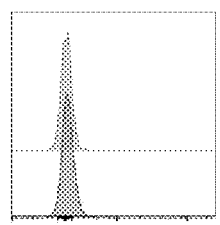

+/- 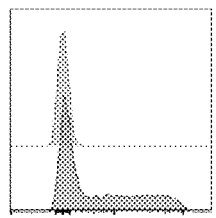

++++ 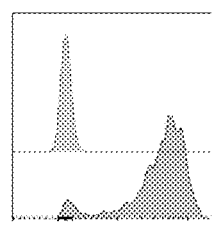

SEQUENCE LISTING

<160> NUMBER OF SEQ ID NOS: 65

<210> SEQ ID NO 1
<211> LENGTH: 223
<212> TYPE: PRT
<213> ORGANISM: Homo sapiens

<400> SEQUENCE: 1

Met Met Thr Gly Thr Ile Glu Thr Thr Gly Asn Ile Ser Ala Glu Lys
1               5                   10                  15

Gly Gly Ser Ile Ile Leu Gln Cys His Leu Ser Ser Thr Thr Ala Gln
            20                  25                  30

Val Thr Gln Val Asn Trp Glu Gln Gln Asp Gln Leu Leu Ala Ile Cys
        35                  40                  45

Asn Ala Asp Leu Gly Trp His Ile Ser Pro Ser Phe Lys Asp Arg Val
    50                  55                  60

Ala Pro Gly Pro Gly Leu Gly Leu Thr Leu Gln Ser Leu Thr Val Asn
65                  70                  75                  80

-continued

```
Asp Thr Gly Glu Tyr Phe Cys Ile Tyr His Thr Tyr Pro Asp Gly Thr
                 85                  90                  95

Tyr Thr Gly Arg Ile Phe Leu Glu Val Leu Glu Ser Ser Val Ala Glu
            100                 105                 110

His Gly Ala Arg Phe Gln Ile Pro Leu Leu Gly Ala Met Ala Ala Thr
            115                 120                 125

Leu Val Val Ile Cys Thr Ala Val Ile Val Val Ala Leu Thr Arg
130                 135                 140

Lys Lys Lys Ala Leu Arg Ile His Ser Val Glu Gly Asp Leu Arg Arg
145                 150                 155                 160

Lys Ser Ala Gly Gln Glu Glu Trp Ser Pro Ser Ala Pro Ser Pro Pro
                165                 170                 175

Gly Ser Cys Val Gln Ala Glu Ala Ala Pro Ala Gly Leu Cys Gly Glu
            180                 185                 190

Gln Arg Gly Glu Asp Cys Ala Glu Leu His Asp Tyr Phe Asn Val Leu
            195                 200                 205

Ser Tyr Arg Ser Leu Gly Asn Cys Ser Phe Phe Thr Glu Thr Gly
    210                 215                 220
```

<210> SEQ ID NO 2
<211> LENGTH: 19
<212> TYPE: PRT
<213> ORGANISM: Homo sapiens

<400> SEQUENCE: 2

```
Met Gly Trp Ser Trp Ile Phe Phe Leu Leu Ser Gly Thr Ala Ser
1               5                   10                  15

Val Leu Ser
```

<210> SEQ ID NO 3
<211> LENGTH: 122
<212> TYPE: PRT
<213> ORGANISM: Homo sapiens

<400> SEQUENCE: 3

```
Met Met Thr Gly Thr Ile Glu Thr Thr Gly Asn Ile Ser Ala Glu Lys
1               5                   10                  15

Gly Gly Ser Ile Ile Leu Gln Cys His Leu Ser Ser Thr Thr Ala Gln
            20                  25                  30

Val Thr Gln Val Asn Trp Glu Gln Gln Asp Gln Leu Leu Ala Ile Cys
        35                  40                  45

Asn Ala Asp Leu Gly Trp His Ile Ser Pro Ser Phe Lys Asp Arg Val
50                  55                  60

Ala Pro Gly Pro Gly Leu Gly Leu Thr Leu Gln Ser Leu Thr Val Asn
65                  70                  75                  80

Asp Thr Gly Glu Tyr Phe Cys Ile Tyr His Thr Tyr Pro Asp Gly Thr
                85                  90                  95

Tyr Thr Gly Arg Ile Phe Leu Glu Val Leu Glu Ser Ser Val Ala Glu
            100                 105                 110

His Gly Ala Arg Phe Gln Ile Pro Thr Gly
            115                 120
```

<210> SEQ ID NO 4
<211> LENGTH: 4
<212> TYPE: PRT
<213> ORGANISM: Artificial sequence
<220> FEATURE:
<223> OTHER INFORMATION: Synthetic construct

<400> SEQUENCE: 4

Thr Gly Gly Gly
1

<210> SEQ ID NO 5
<211> LENGTH: 232
<212> TYPE: PRT
<213> ORGANISM: Homo sapiens

<400> SEQUENCE: 5

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 6
<211> LENGTH: 317
<212> TYPE: PRT
<213> ORGANISM: Homo sapiens

<400> SEQUENCE: 6

Asp Val Val Gln Ala Pro Thr Gln Val Pro Gly Phe Leu Gly Asp
1               5                   10                  15

Ser Val Thr Leu Pro Cys Tyr Leu Gln Val Pro Asn Met Glu Val Thr
            20                  25                  30

His Val Ser Gln Leu Thr Trp Ala Arg His Gly Glu Ser Gly Ser Met
        35                  40                  45

Ala Val Phe His Gln Thr Gln Gly Pro Ser Tyr Ser Glu Ser Lys Arg
    50                  55                  60

-continued

```
Leu Glu Phe Val Ala Ala Arg Leu Gly Ala Glu Leu Arg Asn Ala Ser
 65                  70                  75                  80

Leu Arg Met Phe Gly Leu Arg Val Glu Asp Glu Gly Asn Tyr Thr Cys
                 85                  90                  95

Leu Phe Val Thr Phe Pro Gln Gly Ser Arg Ser Val Asp Ile Trp Leu
            100                 105                 110

Arg Val Leu Ala Lys Pro Gln Asn Thr Ala Glu Val Gln Lys Val Gln
        115                 120                 125

Leu Thr Gly Glu Pro Val Pro Met Ala Arg Cys Val Ser Thr Gly Gly
    130                 135                 140

Arg Pro Pro Ala Gln Ile Thr Trp His Ser Asp Leu Gly Gly Met Pro
145                 150                 155                 160

Asn Thr Ser Gln Val Pro Gly Phe Leu Ser Gly Thr Val Thr Val Thr
                165                 170                 175

Ser Leu Trp Ile Leu Val Pro Ser Ser Gln Val Asp Gly Lys Asn Val
            180                 185                 190

Thr Cys Lys Val Glu His Glu Ser Phe Glu Lys Pro Gln Leu Leu Thr
        195                 200                 205

Val Asn Leu Thr Val Tyr Tyr Pro Pro Glu Val Ser Ile Ser Gly Tyr
    210                 215                 220

Asp Asn Asn Trp Tyr Leu Gly Gln Asn Glu Ala Thr Leu Thr Cys Asp
225                 230                 235                 240

Ala Arg Ser Asn Pro Glu Pro Thr Gly Tyr Asn Trp Ser Thr Thr Met
                245                 250                 255

Gly Pro Leu Pro Pro Phe Ala Val Ala Gln Gly Ala Gln Leu Leu Ile
            260                 265                 270

Arg Pro Val Asp Lys Pro Ile Asn Thr Thr Leu Ile Cys Asn Val Thr
        275                 280                 285

Asn Ala Leu Gly Ala Arg Gln Ala Glu Leu Thr Val Gln Val Lys Glu
    290                 295                 300

Gly Pro Pro Ser Glu His Ser Gly Met Ser Arg Asn Ala
305                 310                 315

<210> SEQ ID NO 7
<211> LENGTH: 553
<212> TYPE: PRT
<213> ORGANISM: Homo sapiens

<400> SEQUENCE: 7

Asp Val Val Gln Ala Pro Thr Gln Val Pro Gly Phe Leu Gly Asp
 1                   5                  10                  15

Ser Val Thr Leu Pro Cys Tyr Leu Gln Val Pro Asn Met Glu Val Thr
                 20                  25                  30

His Val Ser Gln Leu Thr Trp Ala Arg His Gly Glu Ser Gly Ser Met
            35                  40                  45

Ala Val Phe His Gln Thr Gln Gly Pro Ser Tyr Ser Glu Ser Lys Arg
        50                  55                  60

Leu Glu Phe Val Ala Ala Arg Leu Gly Ala Glu Leu Arg Asn Ala Ser
 65                  70                  75                  80

Leu Arg Met Phe Gly Leu Arg Val Glu Asp Glu Gly Asn Tyr Thr Cys
                 85                  90                  95

Leu Phe Val Thr Phe Pro Gln Gly Ser Arg Ser Val Asp Ile Trp Leu
            100                 105                 110

Arg Val Leu Ala Lys Pro Gln Asn Thr Ala Glu Val Gln Lys Val Gln
        115                 120                 125
```

-continued

```
Leu Thr Gly Glu Pro Val Pro Met Ala Arg Cys Val Ser Thr Gly Gly
    130                 135                 140

Arg Pro Pro Ala Gln Ile Thr Trp His Ser Asp Leu Gly Gly Met Pro
145                 150                 155                 160

Asn Thr Ser Gln Val Pro Gly Phe Leu Ser Gly Thr Val Thr Val Thr
                165                 170                 175

Ser Leu Trp Ile Leu Val Pro Ser Ser Gln Val Asp Gly Lys Asn Val
            180                 185                 190

Thr Cys Lys Val Glu His Glu Ser Phe Glu Lys Pro Gln Leu Leu Thr
        195                 200                 205

Val Asn Leu Thr Val Tyr Tyr Pro Pro Glu Val Ser Ile Ser Gly Tyr
    210                 215                 220

Asp Asn Asn Trp Tyr Leu Gly Gln Asn Glu Ala Thr Leu Thr Cys Asp
225                 230                 235                 240

Ala Arg Ser Asn Pro Glu Pro Thr Gly Tyr Asn Trp Ser Thr Thr Met
                245                 250                 255

Gly Pro Leu Pro Pro Phe Ala Val Ala Gln Gly Ala Gln Leu Leu Ile
            260                 265                 270

Arg Pro Val Asp Lys Pro Ile Asn Thr Thr Leu Ile Cys Asn Val Thr
        275                 280                 285

Asn Ala Leu Gly Ala Arg Gln Ala Glu Leu Thr Val Gln Val Lys Glu
    290                 295                 300

Gly Pro Pro Ser Glu His Ser Gly Met Ser Arg Asn Ala Thr Gly Gly
305                 310                 315                 320

Gly Glu Pro Lys Ser Cys Asp Lys Thr His Thr Cys Pro Pro Cys Pro
                325                 330                 335

Ala Pro Glu Leu Leu Gly Gly Pro Ser Val Phe Leu Phe Pro Pro Lys
            340                 345                 350

Pro Lys Asp Thr Leu Met Ile Ser Arg Thr Pro Glu Val Thr Cys Val
        355                 360                 365

Val Val Asp Val Ser His Glu Asp Pro Glu Val Lys Phe Asn Trp Tyr
    370                 375                 380

Val Asp Gly Val Glu Val His Asn Ala Lys Thr Lys Pro Arg Glu Glu
385                 390                 395                 400

Gln Tyr Asn Ser Thr Tyr Arg Val Val Ser Val Leu Thr Val Leu His
                405                 410                 415

Gln Asp Trp Leu Asn Gly Lys Glu Tyr Lys Cys Lys Val Ser Asn Lys
            420                 425                 430

Ala Leu Pro Ala Pro Ile Glu Lys Thr Ile Ser Lys Ala Lys Gly Gln
        435                 440                 445

Pro Arg Glu Pro Gln Val Tyr Thr Leu Pro Pro Ser Arg Asp Glu Leu
    450                 455                 460

Thr Lys Asn Gln Val Ser Leu Thr Cys Leu Val Lys Gly Phe Tyr Pro
465                 470                 475                 480

Ser Asp Ile Ala Val Glu Trp Glu Ser Asn Gly Gln Pro Glu Asn Asn
                485                 490                 495

Tyr Lys Thr Thr Pro Pro Val Leu Asp Ser Asp Gly Ser Phe Phe Leu
            500                 505                 510

Tyr Ser Lys Leu Thr Val Asp Lys Ser Arg Trp Gln Gln Gly Asn Val
        515                 520                 525
```

```
Phe Ser Cys Ser Val Met His Glu Ala Leu His Asn His Tyr Thr Gln
            530                 535                 540
Lys Ser Leu Ser Leu Ser Pro Gly Lys
545                 550
```

<210> SEQ ID NO 8
<211> LENGTH: 8
<212> TYPE: PRT
<213> ORGANISM: Artificial sequence
<220> FEATURE:
<223> OTHER INFORMATION: Synthetic construct

<400> SEQUENCE: 8

```
Asp Tyr Lys Asp Asp Asp Asp Lys
1               5
```

<210> SEQ ID NO 9
<211> LENGTH: 37
<212> TYPE: PRT
<213> ORGANISM: Homo sapiens

<400> SEQUENCE: 9

```
Pro Asn Lys Gly Ser Gly Thr Thr Ser Gly Thr Thr Arg Leu Leu Ser
1               5                   10                  15
Gly His Thr Cys Phe Thr Leu Thr Gly Leu Leu Gly Thr Leu Val Thr
                20                  25                  30
Met Gly Leu Leu Thr
            35
```

<210> SEQ ID NO 10
<211> LENGTH: 119
<212> TYPE: PRT
<213> ORGANISM: Artificial sequence
<220> FEATURE:
<223> OTHER INFORMATION: Synthetic construct

<400> SEQUENCE: 10

```
Asp Val Gln Leu Val Glu Ser Gly Gly Gly Leu Val Gln Pro Gly Gly
1               5                   10                  15
Ser Arg Lys Leu Ser Cys Ala Ala Ser Gly Phe Thr Phe Ser Asn Phe
                20                  25                  30
Gly Met His Trp Val Arg Gln Ala Pro Glu Lys Gly Leu Glu Trp Val
            35                  40                  45
Ala Phe Ile Ser Ser Gly Ser Ser Ile Tyr Tyr Ala Asp Thr Val
    50                  55                  60
Lys Gly Arg Phe Thr Ile Ser Arg Asp Asn Pro Lys Asn Thr Leu Phe
65                  70                  75                  80
Leu Gln Met Thr Ser Leu Arg Ser Glu Asp Thr Ala Met Tyr Tyr Cys
                85                  90                  95
Ala Arg Met Arg Leu Asp Tyr Tyr Ala Met Asp Tyr Trp Gly Gln Gly
                100                 105                 110
Thr Ser Val Thr Val Ser Ser
        115
```

<210> SEQ ID NO 11
<211> LENGTH: 5
<212> TYPE: PRT
<213> ORGANISM: Artificial sequence
<220> FEATURE:
<223> OTHER INFORMATION: Synthetic construct

```
<400> SEQUENCE: 11

Asn Phe Gly Met His
1               5

<210> SEQ ID NO 12
<211> LENGTH: 17
<212> TYPE: PRT
<213> ORGANISM: Artificial sequence
<220> FEATURE:
<223> OTHER INFORMATION: Synthetic construct

<400> SEQUENCE: 12

Phe Ile Ser Ser Gly Ser Ser Ser Ile Tyr Tyr Ala Asp Thr Val Lys
1               5                   10                  15

Gly

<210> SEQ ID NO 13
<211> LENGTH: 10
<212> TYPE: PRT
<213> ORGANISM: Artificial sequence
<220> FEATURE:
<223> OTHER INFORMATION: Synthetic construct

<400> SEQUENCE: 13

Met Arg Leu Asp Tyr Tyr Ala Met Asp Tyr
1               5                   10

<210> SEQ ID NO 14
<211> LENGTH: 107
<212> TYPE: PRT
<213> ORGANISM: Artificial sequence
<220> FEATURE:
<223> OTHER INFORMATION: Synthetic construct

<400> SEQUENCE: 14

Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
                20                  25                  30

Leu Ala Trp Tyr Gln Glu Lys Pro Gly Lys Thr Asn Lys Leu Leu Ile
            35                  40                  45

Tyr Ser Gly Ser Thr Leu Gln Ser Gly Ile Pro Ser Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Trp
                85                  90                  95

Thr Phe Gly Gly Gly Thr Lys Leu Glu Ile Lys
            100                 105

<210> SEQ ID NO 15
<211> LENGTH: 11
<212> TYPE: PRT
<213> ORGANISM: Artificial sequence
<220> FEATURE:
<223> OTHER INFORMATION: Synthetic construct

<400> SEQUENCE: 15

Arg Ala Ser Lys Ser Ile Ser Lys Tyr Leu Ala
1               5                   10
```

```
<210> SEQ ID NO 16
<211> LENGTH: 7
<212> TYPE: PRT
<213> ORGANISM: Artificial sequence
<220> FEATURE:
<223> OTHER INFORMATION: Synthetic construct

<400> SEQUENCE: 16

Ser Gly Ser Thr Leu Gln Ser
1               5

<210> SEQ ID NO 17
<211> LENGTH: 9
<212> TYPE: PRT
<213> ORGANISM: Artificial sequence
<220> FEATURE:
<223> OTHER INFORMATION: Synthetic construct

<400> SEQUENCE: 17

Gln Gln His Asn Glu Tyr Pro Trp Thr
1               5

<210> SEQ ID NO 18
<211> LENGTH: 119
<212> TYPE: PRT
<213> ORGANISM: Artificial sequence
<220> FEATURE:
<223> OTHER INFORMATION: Synthetic construct

<400> SEQUENCE: 18

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
                20                  25                  30

Thr Met His Trp Val Lys Gln Ser His Gly Lys Asn Leu Glu Trp Ile
            35                  40                  45

Gly Gly Ile Asn Pro Asn Asn Gly Gly Thr Ser Tyr Asn Gln Lys Phe
        50                  55                  60

Lys Gly Arg Ala Thr Leu Thr Val Asp Lys Ser Ser Ser Thr Ala Tyr
65                  70                  75                  80

Met Glu Leu Arg Ser Leu Thr Ser Asp Asp Ser Ala Val Tyr Tyr Cys
                85                  90                  95

Ala Arg Pro Gly Trp Tyr Asn Tyr Ala Met Asp Tyr Trp Gly Gln Gly
            100                 105                 110

Thr Ser Val Thr Val Ser Ser
        115

<210> SEQ ID NO 19
<211> LENGTH: 5
<212> TYPE: PRT
<213> ORGANISM: Artificial sequence
<220> FEATURE:
<223> OTHER INFORMATION: Synthetic construct

<400> SEQUENCE: 19

Glu Tyr Thr Met His
1               5

<210> SEQ ID NO 20
<211> LENGTH: 17
<212> TYPE: PRT
<213> ORGANISM: Artificial sequence
<220> FEATURE:
<223> OTHER INFORMATION: Synthetic construct
```

```
<400> SEQUENCE: 20

Gly Ile Asn Pro Asn Asn Gly Gly Thr Ser Tyr Asn Gln Lys Phe Lys
1               5                   10                  15

Gly

<210> SEQ ID NO 21
<211> LENGTH: 10
<212> TYPE: PRT
<213> ORGANISM: Artificial sequence
<220> FEATURE:
<223> OTHER INFORMATION: Synthetic construct

<400> SEQUENCE: 21

Pro Gly Trp Tyr Asn Tyr Ala Met Asp Tyr
1               5                   10

<210> SEQ ID NO 22
<211> LENGTH: 107
<212> TYPE: PRT
<213> ORGANISM: Artificial sequence
<220> FEATURE:
<223> OTHER INFORMATION: Synthetic construct

<400> SEQUENCE: 22

Asp Ile Val Met Thr Gln Ser His Lys Phe Met Ser Thr Ser Val Gly
1               5                   10                  15

Asp Arg Val Asn Ile Thr Cys Lys Ala Ser Gln Gly Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr His Cys Gln Gln His Tyr Ile Thr Pro Trp
                85                  90                  95

Thr Phe Gly Gly Gly Thr Lys Leu Glu Ile Lys
            100                 105

<210> SEQ ID NO 23
<211> LENGTH: 11
<212> TYPE: PRT
<213> ORGANISM: Artificial sequence
<220> FEATURE:
<223> OTHER INFORMATION: Synthetic construct

<400> SEQUENCE: 23

Lys Ala Ser Gln Gly Val Ser Thr Ala Val Ala
1               5                   10

<210> SEQ ID NO 24
<211> LENGTH: 7
<212> TYPE: PRT
<213> ORGANISM: Artificial sequence
<220> FEATURE:
<223> OTHER INFORMATION: Synthetic construct

<400> SEQUENCE: 24

Ser Ala Ser Tyr Arg Tyr Thr
1               5
```

```
<210> SEQ ID NO 25
<211> LENGTH: 9
<212> TYPE: PRT
<213> ORGANISM: Artificial sequence
<220> FEATURE:
<223> OTHER INFORMATION: Synthetic construct

<400> SEQUENCE: 25

Gln Gln His Tyr Ile Thr Pro Trp Thr
1               5

<210> SEQ ID NO 26
<211> LENGTH: 119
<212> TYPE: PRT
<213> ORGANISM: Artificial sequence
<220> FEATURE:
<223> OTHER INFORMATION: Synthetic construct

<400> SEQUENCE: 26

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Ala Phe Ser Asp Tyr
                20                  25                  30

Asp Met Ser Trp Val Arg Gln Thr Pro Glu Lys Arg Leu Glu Trp Val
            35                  40                  45

Ala Tyr Ile Ser Asp Gly Gly Tyr Asn Thr Tyr Tyr Pro Asp Thr Val
        50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Ile Tyr Tyr Cys
                85                  90                  95

Ala Arg Gln Ile Leu Leu Arg Tyr Tyr Phe Asp Tyr Trp Gly Gln Gly
            100                 105                 110

Thr Thr Leu Thr Val Ser Ser
        115

<210> SEQ ID NO 27
<211> LENGTH: 5
<212> TYPE: PRT
<213> ORGANISM: Artificial sequence
<220> FEATURE:
<223> OTHER INFORMATION: Synthetic construct

<400> SEQUENCE: 27

Asp Tyr Asp Met Ser
1               5

<210> SEQ ID NO 28
<211> LENGTH: 17
<212> TYPE: PRT
<213> ORGANISM: Artificial sequence
<220> FEATURE:
<223> OTHER INFORMATION: Synthetic construct

<400> SEQUENCE: 28

Tyr Ile Ser Asp Gly Gly Tyr Asn Thr Tyr Tyr Pro Asp Thr Val Lys
1               5                   10                  15

Gly

<210> SEQ ID NO 29
<211> LENGTH: 10
<212> TYPE: PRT
<213> ORGANISM: Artificial sequence
```

```
<220> FEATURE:
<223> OTHER INFORMATION: Synthetic construct

<400> SEQUENCE: 29

Gln Ile Leu Leu Arg Tyr Tyr Phe Asp Tyr
1               5                   10

<210> SEQ ID NO 30
<211> LENGTH: 113
<212> TYPE: PRT
<213> ORGANISM: Artificial sequence
<220> FEATURE:
<223> OTHER INFORMATION: Synthetic construct

<400> SEQUENCE: 30

Asp Ile Val Met Ser Gln Ser Pro Ser Ser Leu Ala Val Ser Val Gly
1               5                   10                  15

Glu Lys Val Thr Met Thr Cys Lys Ser Ser Gln Ser Leu Leu Tyr Ser
                20                  25                  30

Ser Asn Gln Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr His Ser Tyr Pro Trp Thr Phe Gly Gly Gly Thr Lys Leu Glu Ile
            100                 105                 110

Lys

<210> SEQ ID NO 31
<211> LENGTH: 17
<212> TYPE: PRT
<213> ORGANISM: Artificial sequence
<220> FEATURE:
<223> OTHER INFORMATION: Synthetic construct

<400> SEQUENCE: 31

Lys Ser Ser Gln Ser Leu Leu Tyr Ser Ser Asn Gln Lys Asn Tyr Leu
1               5                   10                  15

Ala

<210> SEQ ID NO 32
<211> LENGTH: 7
<212> TYPE: PRT
<213> ORGANISM: Artificial sequence
<220> FEATURE:
<223> OTHER INFORMATION: Synthetic construct

<400> SEQUENCE: 32

Trp Ala Ser Thr Arg Glu Ser
1               5

<210> SEQ ID NO 33
<211> LENGTH: 9
<212> TYPE: PRT
<213> ORGANISM: Artificial sequence
<220> FEATURE:
<223> OTHER INFORMATION: Synthetic construct
```

```
<400> SEQUENCE: 33

Gln Gln Tyr His Ser Tyr Pro Trp Thr
1               5

<210> SEQ ID NO 34
<211> LENGTH: 138
<212> TYPE: PRT
<213> ORGANISM: Homo sapiens

<400> SEQUENCE: 34

Met Asp Ser Arg Leu Asn Leu Val Phe Leu Val Leu Ile Leu Lys Gly
1               5                   10                  15

Val Gln Cys Glu Val Gln Leu Val Glu Ser Gly Gly Gly Leu Val Gln
                20                  25                  30

Pro Gly Gly Ser Leu Arg Leu Ser Cys Ala Ala Ser Gly Phe Thr Phe
            35                  40                  45

Ser Asn Phe Gly Met His Trp Val Arg Gln Ala Pro Gly Lys Gly Leu
    50                  55                  60

Glu Trp Val Ala Phe Ile Ser Ser Gly Ser Ser Ser Ile Tyr Tyr Ala
65                  70                  75                  80

Asp Thr Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Arg Met Arg Leu Asp Tyr Tyr Ala Met Asp Tyr Trp
        115                 120                 125

Gly Gln Gly Thr Met Val Thr Val Ser Ser
        130                 135

<210> SEQ ID NO 35
<211> LENGTH: 119
<212> TYPE: PRT
<213> ORGANISM: Artificial sequence
<220> FEATURE:
<223> OTHER INFORMATION: Synthetic construct

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Phe
                20                  25                  30

Gly Met His Trp Val Arg Gln Ala Pro Gly Lys Gly Leu Glu Trp Val
            35                  40                  45

Ala Phe Ile Ser Ser Gly Ser Ser Ser Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Met Arg Leu Asp Tyr Tyr Ala Met Asp Tyr Trp Gly Gln Gly
            100                 105                 110

Thr Met Val Thr Val Ser Ser
        115

<210> SEQ ID NO 36
<211> LENGTH: 127
<212> TYPE: PRT
<213> ORGANISM: Homo sapiens
```

<400> SEQUENCE: 36

Met Arg Phe Gln Val Gln Val Leu Gly Leu Leu Leu Leu Trp Ile Ser
1               5                   10                  15

Gly Ala Gln Cys Asp Ile Gln Met Thr Gln Ser Pro Ser Ser Leu Ser
            20                  25                  30

Ala Ser Val Gly Asp Arg Val Thr Ile Thr Cys Arg Ala Ser Lys Ser
        35                  40                  45

Ile Ser Lys Tyr Leu Ala Trp Tyr Gln Gln Lys Pro Gly Lys Ala Pro
    50                  55                  60

Lys Leu Leu Ile Tyr Ser Gly Ser Thr Leu Gln Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln His Asn
            100                 105                 110

Glu Tyr Pro Trp Thr Phe Gly Gly Gly Thr Lys Val Glu Ile Lys
        115                 120                 125

<210> SEQ ID NO 37
<211> LENGTH: 107
<212> TYPE: PRT
<213> ORGANISM: Artificial sequence
<220> FEATURE:
<223> OTHER INFORMATION: Synthetic construct

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Tyr Gln Gln Lys Pro Gly Lys Ala Pro Lys Leu Leu Ile
        35                  40                  45

Tyr Ser Gly Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Asn Glu Tyr Pro Trp
                85                  90                  95

Thr Phe Gly Gly Gly Thr Lys Val Glu Ile Lys
            100                 105

<210> SEQ ID NO 38
<211> LENGTH: 448
<212> TYPE: DNA
<213> ORGANISM: Artificial sequence
<220> FEATURE:
<223> OTHER INFORMATION: Synthetic construct

<400> SEQUENCE: 38
actagtacca ccatggactc caggctcaat ctggttttcc ttgtccttat tctgaaaggc      60
gtccagtgtg aagtgcagct ggtggagtct gggggaggcc tggtgcagcc tggagggtcc    120
ctgagactct cctgtgcagc ctctggattc actttcagta actttggaat gcactgggtt    180
cgacaggctc cagggaaggg gctggagtgg gtcgcattca ttagtagtgg cagtagttcc    240
atctactatg cagacacagt gaagggccga ttcaccatct ccagagacaa tgccaagaac    300
agcctgtacc tgcaaatgaa cagtctgagg gctgaggaca ctgccgtgta ttactgtgca    360

```
agaatgagac tggattacta tgctatggac tactggggtc aaggaaccat ggtcaccgtc    420
tcctcaggta agtatggcct ctaagctt                                       448
```

<210> SEQ ID NO 39
<211> LENGTH: 416
<212> TYPE: DNA
<213> ORGANISM: Artificial sequence
<220> FEATURE:
<223> OTHER INFORMATION: Synthetic construct

<400> SEQUENCE: 39

```
gctagcacca ccatgaggtt ccaggttcag gttctggggc tccttctgct ctggatctca     60
ggagcccagt gtgatatcca gatgacccag tctccatctt ctctttctgc atctgttgga    120
gatagagtca ctattacttg cagggcaagt aagagcatta gcaaatatct ggcctggtat    180
caacagaaac tgggaaagc tcctaagctg cttatctact ctgggtccac tttgcaatct    240
ggagttccat caagattcag tggcagtgga tctggtacag atttcactct caccatcagt    300
agcctgcagc ctgaagattt tgcaacctat tactgtcaac agcataatga ataccctgg    360 accttcggcg gaggcaccaa agtcgaaatc aaacgtaagt agaatccaaa gaattc        416
```

<210> SEQ ID NO 40
<211> LENGTH: 449
<212> TYPE: PRT
<213> ORGANISM: Artificial sequence
<220> FEATURE:
<223> OTHER INFORMATION: Synthetic construct

<400> SEQUENCE: 40

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Phe
            20                  25                  30

Gly Met His Trp Val Arg Gln Ala Pro Gly Lys Gly Leu Glu Trp Val
        35                  40                  45

Ala Phe Ile Ser Ser Gly Ser Ser Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Met Arg Leu Asp Tyr Tyr Ala Met Asp Tyr Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220
```

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
    275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
        340                 345                 350

Leu Pro Pro Ser Arg Asp Glu Leu Thr Lys Asn Gln Val Ser Leu Thr
    355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
    435                 440                 445

Lys

<210> SEQ ID NO 41
<211> LENGTH: 214
<212> TYPE: PRT
<213> ORGANISM: Artificial sequence
<220> FEATURE:
<223> OTHER INFORMATION: Synthetic construct

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Tyr Gln Gln Lys Pro Gly Lys Ala Pro Lys Leu Leu Ile
        35                  40                  45

Tyr Ser Gly Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Asn Glu Tyr Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 42
<211> LENGTH: 138
<212> TYPE: PRT
<213> ORGANISM: Homo sapiens

<400> SEQUENCE: 42

Met Asn Phe Gly Leu Arg Leu Ile Phe Leu Val Leu Thr Leu Lys Gly
1               5                   10                  15

Val Asn Cys Glu Val Gln Leu Val Glu Ser Gly Gly Gly Leu Val Gln
                20                  25                  30

Pro Gly Gly Ser Leu Arg Leu Ser Cys Ala Ala Ser Gly Phe Ala Phe
            35                  40                  45

Ser Asp Tyr Asp Met Ser Trp Val Arg Gln Ala Pro Gly Lys Gly Leu
    50                  55                  60

Glu Trp Val Ala Tyr Ile Ser Asp Gly Gly Tyr Asn Thr Tyr Tyr Pro
65                  70                  75                  80

Asp Thr Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Arg Gln Ile Leu Leu Arg Tyr Tyr Phe Asp Tyr Trp
        115                 120                 125

Gly Gln Gly Thr Thr Val Thr Val Ser Ser
        130                 135

<210> SEQ ID NO 43
<211> LENGTH: 119
<212> TYPE: PRT
<213> ORGANISM: Artificial sequence
<220> FEATURE:
<223> OTHER INFORMATION: Synthetic construct

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Asp Tyr
                20                  25                  30

Asp Met Ser Trp Val Arg Gln Ala Pro Gly Lys Gly Leu Glu Trp Val
            35                  40                  45

Ala Tyr Ile Ser Asp Gly Gly Tyr Asn Thr Tyr Tyr Pro Asp Thr Val
    50                  55                  60

Lys Gly Arg Phe Thr Ile Ser Arg Asp Asn Ala Lys Asn Ser Leu Tyr
65                  70                  75                  80
```

```
Leu Gln Met Asn Ser Leu Arg Ala Glu Asp Thr Ala Val Tyr Tyr Cys
                85                  90                  95

Ala Arg Gln Ile Leu Leu Arg Tyr Tyr Phe Asp Tyr Trp Gly Gln Gly
            100                 105                 110

Thr Thr Val Thr Val Ser Ser
        115

<210> SEQ ID NO 44
<211> LENGTH: 133
<212> TYPE: PRT
<213> ORGANISM: Homo sapiens

<400> SEQUENCE: 44

Met Asp Ser Gln Ala Gln Val Leu Met Leu Leu Leu Leu Trp Val Ser
1               5                   10                  15

Gly Thr Cys Gly Asp Ile Gln Met Thr Gln Ser Pro Ser Ser Leu Ser
            20                  25                  30

Ala Ser Val Gly Asp Arg Val Thr Ile Thr Cys Lys Ser Ser Gln Ser
            35                  40                  45

Leu Leu Tyr Ser Ser Asn Gln Lys Asn Tyr Leu Ala Trp Tyr Gln Gln
        50                  55                  60

Lys Pro Gly Lys Ala Pro Lys Leu Leu Ile Tyr Trp Ala Ser Thr Arg
65                  70                  75                  80

Glu Ser Gly Val Pro Ser Arg Phe Ser Gly Ser Gly Ser Gly Thr Asp
                85                  90                  95

Phe Thr Leu Thr Ile Ser Ser Leu Gln Pro Glu Asp Phe Ala Val Tyr
            100                 105                 110

Tyr Cys Gln Gln Tyr His Ser Tyr Pro Trp Thr Phe Gly Gly Gly Thr
            115                 120                 125

Lys Val Glu Ile Lys
    130

<210> SEQ ID NO 45
<211> LENGTH: 113
<212> TYPE: PRT
<213> ORGANISM: Artificial sequence
<220> FEATURE:
<223> OTHER INFORMATION: Synthetic construct

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Tyr Ser
            20                  25                  30

Ser Asn Gln Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Val Tyr Tyr Cys Gln Gln
                85                  90                  95

Tyr His Ser Tyr Pro Trp Thr Phe Gly Gly Gly Thr Lys Val Glu Ile
            100                 105                 110

Lys
```

-continued

<210> SEQ ID NO 46
<211> LENGTH: 448
<212> TYPE: DNA
<213> ORGANISM: Artificial sequence
<220> FEATURE:
<223> OTHER INFORMATION: Synthetic construct

<400> SEQUENCE: 46

```
actagtacca ccatgaactt tgggctcaga ttgattttcc ttgtccttac tctgaaaggc      60
gtgaactgtg aagtccagct cgtggagtct gggggaggcc ttgtgcagcc tggagggtcc     120
ctgagactct cctgtgcagc ctctggattc gctttcagtg actatgacat gtcttgggtt     180
cgccaggctc ctggcaaggg gctggagtgg gtcgcataca ttagtgatgg cggttataac     240
acctactatc cagacactgt gaagggccga ttcaccatct ccagagacaa tgccaagaac     300
tccctgtacc tgcaaatgaa cagtctgagg gctgaggaca cagccgtcta ttactgtgca     360
agacaaattc tgctgcggta ctactttgac tactggggcc aaggcaccac tgtcacagtc     420
tcctcaggtg agtccttaaa acaagctt                                        448
```

<210> SEQ ID NO 47
<211> LENGTH: 434
<212> TYPE: DNA
<213> ORGANISM: Artificial sequence
<220> FEATURE:
<223> OTHER INFORMATION: Synthetic construct

<400> SEQUENCE: 47

```
gctagcacca ccatggattc acaggcccag gttcttatgc tgctgctgct ctgggtttct      60
ggaacctgtg gggacattca gatgacacag tctccatcct ccctgtctgc ctcagttgga     120
gacagggtta ctatcacctg caagtccagt cagagtcttc tgtatagtag caatcaaaag     180
aactacttgg cctggtacca gcagaaacca gggaaggctc taaactgct gatttactgg      240
gcatccacta gggaatctgg ggtccctagt cgcttctcag gcagtggatc tgggacagat     300
ttcactctca ccatcagcag tctgcagcct gaagacttcg cagtttatta ctgtcagcaa     360
tatcatagct atccctggac cttcggcgga ggcaccaagg tggaaatcaa acgtaagtag     420
aatccaaaga attc                                                       434
```

<210> SEQ ID NO 48
<211> LENGTH: 449
<212> TYPE: PRT
<213> ORGANISM: Artificial sequence
<220> FEATURE:
<223> OTHER INFORMATION: Synthetic construct

<400> SEQUENCE: 48

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Ala Phe Ser Asp Tyr
             20                  25                  30

Asp Met Ser Trp Val Arg Gln Ala Pro Gly Lys Gly Leu Glu Trp Val
         35                  40                  45

Ala Tyr Ile Ser Asp Gly Gly Tyr Asn Thr Tyr Tyr Pro Asp Thr Val
     50                  55                  60

Lys Gly Arg Phe Thr Ile Ser Arg Asp Asn Ala Lys Asn Ser Leu Tyr
 65                  70                  75                  80
```

Leu Gln Met Asn Ser Leu Arg Ala Glu Asp Thr Ala Val Tyr Tyr Cys
                    85                  90                  95

Ala Arg Gln Ile Leu Leu Arg Tyr Tyr Phe Asp Tyr Trp Gly Gln Gly
                100                 105                 110

Thr Thr Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 49
<211> LENGTH: 220
<212> TYPE: PRT
<213> ORGANISM: Artificial sequence
<220> FEATURE:
<223> OTHER INFORMATION: Synthetic construct

<400> SEQUENCE: 49

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Tyr Ser
            20                  25                  30

Ser Asn Gln Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Val Tyr Tyr Cys Gln Gln
                85                  90                  95

Tyr His Ser Tyr Pro Trp Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 50
<211> LENGTH: 122
<212> TYPE: PRT
<213> ORGANISM: Homo sapiens

<400> SEQUENCE: 50

Met Met Thr Gly Thr Ile Glu Thr Thr Gly Asn Ile Ser Ala Glu Lys
1               5                   10                  15

Gly Gly Ser Ile Ile Leu Gln Cys His Leu Ser Ser Thr Thr Ala Gln
            20                  25                  30

Val Thr Ala Val Asn Trp Glu Gln Gln Asp Gln Leu Leu Ala Ile Cys
        35                  40                  45

Asn Ala Asp Leu Gly Trp His Ile Ser Pro Ser Phe Lys Asp Arg Val
    50                  55                  60

Ala Pro Gly Pro Gly Leu Gly Leu Thr Leu Gln Ser Leu Thr Val Asn
65                  70                  75                  80

Asp Thr Gly Glu Tyr Phe Cys Ile Tyr His Thr Tyr Pro Asp Gly Thr
                85                  90                  95

Tyr Thr Gly Arg Ile Phe Leu Glu Val Leu Glu Ser Ser Val Ala Glu
            100                 105                 110

His Gly Ala Arg Phe Gln Ile Pro Thr Gly
        115                 120

```
<210> SEQ ID NO 51
<211> LENGTH: 122
<212> TYPE: PRT
<213> ORGANISM: Homo sapiens

<400> SEQUENCE: 51

Met Met Thr Gly Thr Ile Glu Thr Thr Gly Asn Ile Ser Ala Glu Lys
1               5                   10                  15

Gly Gly Ser Ile Ile Leu Gln Cys His Leu Ser Ser Thr Thr Ala Gln
            20                  25                  30

Val Thr Gln Val Ala Trp Glu Gln Gln Asp Gln Leu Leu Ala Ile Cys
        35                  40                  45

Asn Ala Asp Leu Gly Trp His Ile Ser Pro Ser Phe Lys Asp Arg Val
50                  55                  60

Ala Pro Gly Pro Gly Leu Gly Leu Thr Leu Gln Ser Leu Thr Val Asn
65                  70                  75                  80

Asp Thr Gly Glu Tyr Phe Cys Ile Tyr His Thr Tyr Pro Asp Gly Thr
                85                  90                  95

Tyr Thr Gly Arg Ile Phe Leu Glu Val Leu Glu Ser Ser Val Ala Glu
            100                 105                 110

His Gly Ala Arg Phe Gln Ile Pro Thr Gly
        115                 120

<210> SEQ ID NO 52
<211> LENGTH: 122
<212> TYPE: PRT
<213> ORGANISM: Homo sapiens

<400> SEQUENCE: 52

Met Met Thr Gly Thr Ile Glu Thr Thr Gly Asn Ile Ser Ala Glu Lys
1               5                   10                  15

Gly Gly Ser Ile Ile Leu Gln Cys His Leu Ser Ser Thr Thr Ala Gln
            20                  25                  30

Val Thr Gln Val Asn Trp Ala Gln Gln Asp Gln Leu Leu Ala Ile Cys
        35                  40                  45

Asn Ala Asp Leu Gly Trp His Ile Ser Pro Ser Phe Lys Asp Arg Val
50                  55                  60

Ala Pro Gly Pro Gly Leu Gly Leu Thr Leu Gln Ser Leu Thr Val Asn
65                  70                  75                  80

Asp Thr Gly Glu Tyr Phe Cys Ile Tyr His Thr Tyr Pro Asp Gly Thr
                85                  90                  95

Tyr Thr Gly Arg Ile Phe Leu Glu Val Leu Glu Ser Ser Val Ala Glu
            100                 105                 110

His Gly Ala Arg Phe Gln Ile Pro Thr Gly
        115                 120

<210> SEQ ID NO 53
<211> LENGTH: 122
<212> TYPE: PRT
<213> ORGANISM: Homo sapiens

<400> SEQUENCE: 53

Met Met Thr Gly Thr Ile Glu Thr Thr Gly Asn Ile Ser Ala Glu Lys
1               5                   10                  15

Gly Gly Ser Ile Ile Leu Gln Cys His Leu Ser Ser Thr Thr Ala Gln
            20                  25                  30

Val Thr Gln Val Asn Trp Glu Gln Gln Asp Gln Leu Leu Ala Ile Cys
        35                  40                  45
```

Ala Ala Asp Leu Gly Trp His Ile Ser Pro Ser Phe Lys Asp Arg Val
    50                  55                  60

Ala Pro Gly Pro Gly Leu Gly Leu Thr Leu Gln Ser Leu Thr Val Asn
65                  70                  75                  80

Asp Thr Gly Glu Tyr Phe Cys Ile Tyr His Thr Tyr Pro Asp Gly Thr
                85                  90                  95

Tyr Thr Gly Arg Ile Phe Leu Glu Val Leu Glu Ser Ser Val Ala Glu
                100                 105                 110

His Gly Ala Arg Phe Gln Ile Pro Thr Gly
            115                 120

<210> SEQ ID NO 54
<211> LENGTH: 122
<212> TYPE: PRT
<213> ORGANISM: Homo sapiens

<400> SEQUENCE: 54

Met Met Thr Gly Thr Ile Glu Thr Thr Gly Asn Ile Ser Ala Glu Lys
1               5                   10                  15

Gly Gly Ser Ile Ile Leu Gln Cys His Leu Ser Ser Thr Thr Ala Gln
                20                  25                  30

Val Thr Gln Val Asn Trp Glu Gln Gln Asp Gln Leu Leu Ala Ile Cys
            35                  40                  45

Asn Ala Ala Leu Gly Trp His Ile Ser Pro Ser Phe Lys Asp Arg Val
    50                  55                  60

Ala Pro Gly Pro Gly Leu Gly Leu Thr Leu Gln Ser Leu Thr Val Asn
65                  70                  75                  80

Asp Thr Gly Glu Tyr Phe Cys Ile Tyr His Thr Tyr Pro Asp Gly Thr
                85                  90                  95

Tyr Thr Gly Arg Ile Phe Leu Glu Val Leu Glu Ser Ser Val Ala Glu
                100                 105                 110

His Gly Ala Arg Phe Gln Ile Pro Thr Gly
            115                 120

<210> SEQ ID NO 55
<211> LENGTH: 122
<212> TYPE: PRT
<213> ORGANISM: Homo sapiens

<400> SEQUENCE: 55

Met Met Thr Gly Thr Ile Glu Thr Thr Gly Asn Ile Ser Ala Glu Lys
1               5                   10                  15

Gly Gly Ser Ile Ile Leu Gln Cys His Leu Ser Ser Thr Thr Ala Gln
                20                  25                  30

Val Thr Gln Val Asn Trp Glu Gln Gln Asp Gln Leu Leu Ala Ile Cys
            35                  40                  45

Asn Ala Asp Leu Gly Trp His Ile Ser Pro Ser Phe Lys Asp Arg Val
    50                  55                  60

Ala Pro Gly Pro Gly Leu Gly Leu Thr Leu Gln Ser Leu Thr Val Asn
65                  70                  75                  80

Asp Thr Gly Glu Tyr Ala Cys Ile Tyr His Thr Tyr Pro Asp Gly Thr
                85                  90                  95

Tyr Thr Gly Arg Ile Phe Leu Glu Val Leu Glu Ser Ser Val Ala Glu
                100                 105                 110

His Gly Ala Arg Phe Gln Ile Pro Thr Gly
            115                 120

```
<210> SEQ ID NO 56
<211> LENGTH: 447
<212> TYPE: PRT
<213> ORGANISM: Homo sapiens

<400> SEQUENCE: 56

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ala Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380
```

```
Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly
            435                 440                 445
```

<210> SEQ ID NO 57
<211> LENGTH: 214
<212> TYPE: PRT
<213> ORGANISM: Homo sapiens

<400> SEQUENCE: 57

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Phe Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 58
<211> LENGTH: 263
<212> TYPE: PRT
<213> ORGANISM: Homo sapiens

<400> SEQUENCE: 58

```
Met Arg Trp Cys Leu Leu Leu Ile Trp Ala Gln Gly Leu Arg Gln Ala
1               5                   10                  15

Pro Leu Ala Ser Gly Tyr Pro Tyr Asp Val Pro Asp Tyr Ala Gly Gly
            20                  25                  30

Gly Gly Ser Gly Gly Gly Gly Ser Met Met Thr Gly Thr Ile Glu Thr
        35                  40                  45
```

-continued

```
Thr Gly Asn Ile Ser Ala Glu Lys Gly Gly Ser Ile Ile Leu Gln Cys
 50                  55                  60

His Leu Ser Ser Thr Thr Ala Gln Val Thr Gln Val Asn Trp Glu Gln
 65                  70                  75                  80

Gln Asp Gln Leu Leu Ala Ile Cys Asn Ala Asp Leu Gly Trp His Ile
                 85                  90                  95

Ser Pro Ser Phe Lys Asp Arg Val Ala Pro Gly Pro Gly Leu Gly Leu
                100                 105                 110

Thr Leu Gln Ser Leu Thr Val Asn Asp Thr Gly Glu Tyr Phe Cys Ile
                115                 120                 125

Tyr His Thr Tyr Pro Asp Gly Thr Tyr Thr Gly Arg Ile Phe Leu Glu
130                 135                 140

Val Leu Glu Ser Ser Val Ala Glu His Gly Ala Arg Phe Gln Ile Pro
145                 150                 155                 160

Leu Leu Gly Ala Met Ala Ala Thr Leu Val Val Ile Cys Thr Ala Val
                165                 170                 175

Ile Val Val Val Ala Leu Thr Arg Lys Lys Lys Ala Leu Arg Ile His
                180                 185                 190

Ser Val Glu Gly Asp Leu Arg Arg Lys Ser Ala Gly Gln Glu Glu Trp
            195                 200                 205

Ser Pro Ser Ala Pro Ser Pro Gly Ser Cys Val Gln Ala Glu Ala
            210                 215                 220

Ala Pro Ala Gly Leu Cys Gly Glu Gln Arg Gly Glu Asp Cys Ala Glu
225                 230                 235                 240

Leu His Asp Tyr Phe Asn Val Leu Ser Tyr Arg Ser Leu Gly Asn Cys
                245                 250                 255

Ser Phe Phe Thr Glu Thr Gly
                260
```

<210> SEQ ID NO 59
<211> LENGTH: 358
<212> TYPE: PRT
<213> ORGANISM: Homo sapiens

<400> SEQUENCE: 59

```
Met Met Thr Gly Thr Ile Glu Thr Thr Gly Asn Ile Ser Ala Glu Lys
  1               5                  10                  15

Gly Gly Ser Ile Ile Leu Gln Cys His Leu Ser Ser Thr Thr Ala Gln
                 20                  25                  30

Val Thr Gln Val Asn Trp Glu Gln Gln Asp Gln Leu Leu Ala Ile Cys
             35                  40                  45

Asn Ala Asp Leu Gly Trp His Ile Ser Pro Ser Phe Lys Asp Arg Val
 50                  55                  60

Ala Pro Gly Pro Gly Leu Gly Leu Thr Leu Gln Ser Leu Thr Val Asn
 65                  70                  75                  80

Asp Thr Gly Glu Tyr Phe Cys Ile Tyr His Thr Tyr Pro Asp Gly Thr
                 85                  90                  95

Tyr Thr Gly Arg Ile Phe Leu Glu Val Leu Glu Ser Ser Val Ala Glu
                100                 105                 110

His Gly Ala Arg Phe Gln Ile Pro Thr Gly Thr Gly Gly Glu Pro
            115                 120                 125

Lys Ser Cys Asp Lys Thr His Thr Cys Pro Pro Cys Pro Ala Pro Glu
130                 135                 140

Leu Leu Gly Gly Pro Ser Val Phe Leu Phe Pro Pro Lys Pro Lys Asp
145                 150                 155                 160
```

```
Thr Leu Met Ile Ser Arg Thr Pro Glu Val Thr Cys Val Val Val Asp
            165                 170                 175

Val Ser His Glu Asp Pro Glu Val Lys Phe Asn Trp Tyr Val Asp Gly
        180                 185                 190

Val Glu Val His Asn Ala Lys Thr Lys Pro Arg Glu Glu Gln Tyr Asn
    195                 200                 205

Ser Thr Tyr Arg Val Val Ser Val Leu Thr Val Leu His Gln Asp Trp
210                 215                 220

Leu Asn Gly Lys Glu Tyr Lys Cys Lys Val Ser Asn Lys Ala Leu Pro
225                 230                 235                 240

Ala Pro Ile Glu Lys Thr Ile Ser Lys Ala Lys Gly Gln Pro Arg Glu
            245                 250                 255

Pro Gln Val Tyr Thr Leu Pro Pro Ser Arg Asp Glu Leu Thr Lys Asn
        260                 265                 270

Gln Val Ser Leu Thr Cys Leu Val Lys Gly Phe Tyr Pro Ser Asp Ile
    275                 280                 285

Ala Val Glu Trp Glu Ser Asn Gly Gln Pro Glu Asn Asn Tyr Lys Thr
290                 295                 300

Thr Pro Pro Val Leu Asp Ser Asp Gly Ser Phe Phe Leu Tyr Ser Lys
305                 310                 315                 320

Leu Thr Val Asp Lys Ser Arg Trp Gln Gln Gly Asn Val Phe Ser Cys
            325                 330                 335

Ser Val Met His Glu Ala Leu His Asn His Tyr Thr Gln Lys Ser Leu
        340                 345                 350

Ser Leu Ser Pro Gly Lys
        355

<210> SEQ ID NO 60
<211> LENGTH: 449
<212> TYPE: PRT
<213> ORGANISM: Artificial sequence
<220> FEATURE:
<223> OTHER INFORMATION: Synthetic construct

<400> SEQUENCE: 60

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Phe
            20                  25                  30

Gly Met His Trp Val Arg Gln Ala Pro Gly Lys Gly Leu Glu Trp Val
        35                  40                  45

Ala Phe Ile Ser Ser Gly Ser Ser Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Met Arg Leu Asp Tyr Tyr Ala Met Asp Tyr Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160
```

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gln Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 61
<211> LENGTH: 446
<212> TYPE: PRT
<213> ORGANISM: Artificial sequence
<220> FEATURE:
<223> OTHER INFORMATION: Synthetic construct

<400> SEQUENCE: 61

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Phe
            20                  25                  30

Gly Met His Trp Val Arg Gln Ala Pro Gly Lys Gly Leu Glu Trp Val
        35                  40                  45

Ala Phe Ile Ser Ser Gly Ser Ser Ile Tyr Tyr Ala Asp Thr Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
             85                  90                  95

Ala Arg Met Arg Leu Asp Tyr Tyr Ala Met Asp Tyr Trp Gly Gln Gly
         100                 105                 110

Thr Met Val Thr Val Ser Ser Ala Ser Thr Lys Gly Pro Ser Val Phe
     115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445

<210> SEQ ID NO 62
<211> LENGTH: 449
<212> TYPE: PRT
<213> ORGANISM: Artificial sequence
<220> FEATURE:
<223> OTHER INFORMATION: Synthetic construct

```
<400> SEQUENCE: 62

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Ala Phe Ser Asp Tyr
             20                  25                  30

Asp Met Ser Trp Val Arg Gln Ala Pro Gly Lys Gly Leu Glu Trp Val
         35                  40                  45

Ala Tyr Ile Ser Asp Gly Gly Tyr Asn Thr Tyr Tyr Pro Asp Thr Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gln Ile Leu Leu Arg Tyr Tyr Phe Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gln Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415
```

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 63
<211> LENGTH: 446
<212> TYPE: PRT
<213> ORGANISM: Artificial sequence
<220> FEATURE:
<223> OTHER INFORMATION: Synthetic construct

<400> SEQUENCE: 63

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Asp Tyr
            20                  25                  30

Asp Met Ser Trp Val Arg Gln Ala Pro Gly Lys Gly Leu Glu Trp Val
            35                  40                  45

Ala Tyr Ile Ser Asp Gly Gly Tyr Asn Thr Tyr Tyr Pro Asp Thr Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Gln Ile Leu Leu Arg Tyr Tyr Phe Asp Tyr Trp Gly Gln Gly
            100                 105                 110

Thr Thr Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
            195                 200                 205

Ser Asn Thr Lys Val Asp Lys Arg Val Glu Ser Lys Tyr Gly Pro Pro
        210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Tyr Arg Val Val Ser Val
        290                 295                 300

```
Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445

<210> SEQ ID NO 64
<211> LENGTH: 214
<212> TYPE: PRT
<213> ORGANISM: Artificial sequence
<220> FEATURE:
<223> OTHER INFORMATION: Synthetic construct

<400> SEQUENCE: 64

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Tyr Gln Gln Lys Pro Gly Lys Ala Pro Lys Leu Leu Ile
        35                  40                  45

Tyr Ser Gly Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Asn Glu Tyr Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 65
<211> LENGTH: 220
<212> TYPE: PRT
<213> ORGANISM: Artificial sequence
<220> FEATURE:
<223> OTHER INFORMATION: Synthetic construct

<400> SEQUENCE: 65

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Tyr Ser
            20                  25                  30

Ser Asn Gln Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Val Tyr Tyr Cys Gln Gln
                85                  90                  95

Tyr His Ser Tyr Pro Trp Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

ANTIBODIES TO TIGIT

CROSS REFERENCE TO RELATED APPLICATIONS

This application claims priority to U.S. Provisional Patent Application No. 62/304,045, filed Mar. 4, 2016, and U.S. Provisional Patent Application No. 62/413,025, filed Oct. 26, 2016, the disclosures of each of which are incorporated by reference herein in their entireties.

INCORPORATION BY REFERENCE

The instant application contains a Sequence Listing which has been filed electronically in ASCII format and is hereby incorporated by reference in its entirety. Said ASCII copy, created on May 12, 2017, is named 50658-504001US_Sequence_Listing_052017.txt and is 85,614 bytes in size.

FIELD OF INVENTION

Provided herein, inter alia, are monoclonal antibodies that specifically bind to immune checkpoint molecules, thereby resulting in substantial activation of immune cells as well as uses of the same for the treatment of cancer and infectious disease, among other applications.

BACKGROUND

The antigen-specific immune response is a complex biological process that is controlled by multiple layers of positive and negative regulators. T cells are initially stimulated through the T cell receptor (TCR) by the recognition of their cognate peptide antigen presented by major histocompatibility complex (MHC) molecules on antigen-presenting cells. Optimal T cell activation requires a "second signal" provided by costimulatory molecules such as CD28. The immune response is further regulated positively by costimulatory molecules, such as OX40, GITR, and 4-1BB that belong to the TNF receptor super-family, and negatively regulated by checkpoint molecules such as PD-1 and CTLA-4. The function of checkpoint molecules is to prevent undesired overreaction of the immune system in the body; however, they also restrict the ability of the immune system to effectively fight against cancer and infectious disease. Blocking the function of PD-1 or CTLA-4 by an antagonistic monoclonal IgG antibody has been reported to be effective for immunotherapy of cancer in humans (for review, see Pardoll, *Nat. Rev. Cancer,* 12:252-264, 2012; Mahoney et al., *Nat. Rev. Drug Discov.* 14:561-584, 2015; Shin et al., *Curr. Opin. Immunol.* 33:23-35, 2015; Marquez-Rodas et al. *Ann. Transl. Med.* 3:267, 2015).

Other checkpoint molecules such as TIM-3, LAG-3, TIGIT, BTLA, and VISTA have been reported (Mercier et al., *Front. Immunol.* 6:418, 2015). TIGIT (T cell immunoreceptor with Ig and ITIM domains), a member of the immunoglobulin superfamily with an immunoreceptor tyrosine-based inhibitory motif (ITIM) in the cytoplasmic tail, is expressed on subsets of activated T cells and natural killer (NK) cells (Yu et al., *Nat. Immunol.* 10:48-57, 2009). TIGIT is known to interact with CD155 (also called PVR and necl-5), CD112 (also called PVRL2 and nectin-2), and possibly CD113 (also called PVRL3 and nectin-3) (Mercier et al., supra; Martinet et al., Nat. Rev. Immunol. 15:243-254, 2015). Binding of TIGIT with a high affinity ligand CD155, which are expressed on antigen-presenting cells, has been reported to suppress the function of T cells and NK cells (Mercier et al., supra; Joller et al., *J. Immunol.* 186: 1338-1342, 2011; Stanietsky et al., *Eur. J. Immunol.* 43:2138-2150, 2013; Li et al., J. Biol. Chem. 289:17647-17657, 2014; Zhang et al. *Cancer Immunol. Immunother.* Epub on Feb. 3, 2016). TIGIT has also been reported to inhibit T cells indirectly by modulating cytokine production by dendritic cells (Yu et al., supra).

Tumors constitute highly suppressive microenvironments where infiltrating T cells are exhausted and NK cells are silenced by checkpoint molecules such as PD-1 and TIGIT to evade from the immune responses (Johnston et al., Cancer Cell. 26:926-937, 2014; Chauvin et al., *J. Clin. Invest.* 125:2046-2058, 2015; Inozume et al., *J. Invest. Dermatol.* Epub on Oct. 12, 2015). A high-level expression of TIGIT on CD8+ T cells has been reported to correlate with poor clinical outcomes of AML subjects (Kong et al., *Clin. Cancer Res.* Epub on Jan. 13, 2016). The functional defects of exhausted TIGIT+CD8+ T cells from AML subjects were reported to be reversed by the siRNA-mediated knockdown of TIGIT expression (Kong et al., supra). It has also been reported that effector CD8+ T cells during HIV infection in blood and SIV infection in lymphoid tissue exhibit higher levels of TIGIT (Chew et al., *PLOS Pathogens,* 12:e1005349, 2016). In addition, an ex vivo antibody blockade of TIGIT was reported to restore viral-specific CD8+ T cell effector responses.

SUMMARY

The invention provides, inter alia, an antibody that competes with any of TIG1, TIG2 or TIG3 for binding to human TIGIT. Antibody TIG1 is characterized by a mature light chain variable region of SEQ ID NO:14 and mature heavy chain variable region of SEQ ID NO:10, antibody TIG2 is characterized by a mature light chain variable region of SEQ ID NO:22 and a mature heavy chain variable region of SEQ ID NO:18, and antibody TIG3 is characterized by a mature light chain variable region of SEQ ID NO:30 and a mature heavy chain variable region of SEQ ID NO:26, for specific binding to TIGIT. Some antibodies bind to the same epitope on human TIGIT as TIG1, TIG2, or TIG3. Some antibodies inhibit binding of human TIGIT to CD155. Some antibodies comprise three light chain CDRs and three heavy chain CDRs, substantially from the corresponding three light chain and three heavy chain CDRs from TIG1. Some antibodies comprise three light chain CDRs and three heavy chain CDRs of TIG1, TIG2, or TIG3. Some antibodies comprise three heavy chain CDRs as defined by Kabat and three light chain CDRs as defined by Kabat of any of TIG1 (SEQ ID NOs: 15-17 light chain and 11-13 heavy chain), TIG2 (SEQ ID NOs. 23-25 light chain, 19-21 heavy chain) or TIG3 (SEQ ID NOs: 31-33 light chain and 27-29 heavy chain).

Some monoclonal antibodies bind to an epitope of human TIGIT comprising residues 35 and 37 of SEQ NO:1 and/or residues 49 and 51 of SEQ ID NO:1. Some monoclonal antibodies bind to an epitope of human TIGIT comprising residues 35, 37, 49 and 51 of SEQ ID NO:1. Some monoclonal antibodies bind to a peptide consisting of residues 35-51 of SEQ ID NO:1 and no more than five flanking amino acids from SEQ ID NO:1 on either side. Some monoclonal antibodies bind to a peptide consisting of residues 35-51 of SEQ ID NO:1. Some such monoclonal antibodies bind to an epitope consisting of 3 to 20 contiguous residues of SEQ ID NO:1.

Some antibodies are chimeric, humanized, veneered or human. Some antibodies have human IgG1 kappa isotype.

Some antibodies have human IgG4 kappa isotype. An antibody can be an intact antibody or a single-chain antibody, Fab or F(ab')₂ fragment.

The invention further provides a pharmaceutical composition comprising any of the above antibodies and a pharmaceutically acceptable carrier.

The invention further provides methods of treating or effecting prophylaxis of cancer in a subject, comprising administering to a subject having or at risk of cancer an effective regime of any of the above antibodies. In some methods, the subject has acute myeloid leukemia or adult T-cell leukemia.

In other embodiments, the present invention contemplates the use of the antibodies described herein in combination with immune checkpoint inhibitors. The blockade of immune checkpoints, which results in the amplification of antigen-specific T cell responses, has been shown to be a promising approach in human cancer therapeutics. Examples of immune checkpoints (ligands and receptors), some of which are selectively upregulated in various types of tumor cells, that are candidates for blockade include PD-1 (programmed cell death protein 1); PD-L1 (programmed death ligand-1); BTLA (B and T lymphocyte attenuator); CTLA-4 (cytotoxic T-lymphocyte associated antigen 4); TIM-3 (T-cell membrane protein 3); LAG-3 (lymphocyte activation gene 3); V-domain immunoglobulin suppressor of T cell activation (VISTA); CD96; A2aR (adenosine A2a receptor); A2bR (adenosine A2b receptor); CD73 (ecto-5'-nucleotidase); CD39 (ENTPD1, NTPDase1); Arginase; indoleamine-pyrrole 2,3-dioxygenase (IDO); tryptophan 2,3-dioxygenase (TDO); and Killer Inhibitory Receptors Immune checkpoint inhibitors, and combination therapy therewith, are discussed in detail elsewhere herein.

The invention further provides methods of treating a subject infected with a pathogen comprising administering to the subject an effective regime of an effective regime of any of the above antibodies. In some methods, the pathogen is HIV or SIV. In other methods, the pathogen is a virus, bacteria, fungus, or protozoan.

In additional aspects, provided herein is an anti-TIGIT antibody that binds to a TIGIT polypeptide on one or more amino acid residues comprising D51, wherein the TIGIT polypeptide has an amino acid sequence corresponding to SEQ ID NO:1. In some embodiments, the antibody is a monoclonal antibody. In some embodiments of any of the embodiments disclosed herein, the antibody is chimeric, humanized, or veneered. In some embodiments, the antibody is a human antibody. In some embodiments of any of the embodiments disclosed herein, the antibody does not bind to one or more amino acid residues comprising L44, I47, or H55. In some embodiments of any of the embodiments disclosed herein, the antibody comprises a mature light chain variable region of SEQ ID NO:14 and mature heavy chain variable region of SEQ ID NO:10. In some embodiments of any of the embodiments disclosed herein, the antibody binds to the same epitope as TIG1 on the amino acid sequence corresponding to SEQ ID NO:1. In some embodiments of any of the embodiments disclosed herein, the antibody comprises three light chain CDRs comprising SEQ ID NOs: 15-17 and three heavy chain CDRs comprising SEQ ID NOs: 11-13. In some embodiments of any of the embodiments disclosed herein, the antibody comprises a mature heavy chain variable region with at least 90% sequence identity to SEQ ID NO:35 and a mature light chain variable region with at least 90% sequence identity to SEQ ID NO:37. In some embodiments, the mature heavy chain variable region comprises the amino acid sequence of SEQ ID NO:35 and the mature light chain variable region comprises the amino acid sequence of SEQ ID NO:37. In some embodiments of any of the embodiments disclosed herein, the mature heavy chain variable region is linked to a heavy chain constant region comprising SEQ ID NO:40 provided that the C-terminal lysine may or may not be present, and the mature light chain variable region is linked to the light chain constant region comprising SEQ ID NO:41.

In further aspects, provided herein is a monoclonal antibody that competes with any of TIG1, TIG2 or TIG3 for binding to human TIGIT, wherein antibody TIG1 is characterized by a mature light chain variable region of SEQ ID NO:14 and mature heavy chain variable region of SEQ ID NO:10, antibody TIG2 is characterized by a mature light chain variable region of SEQ ID NO:22 and a mature heavy chain variable region of SEQ ID NO:18, and antibody TIG3 is characterized by a mature light chain variable region of SEQ ID NO:30 and a mature heavy chain variable region of SEQ ID NO:26, for specific binding to CD155. In some embodiments, the antibody binds to the same epitope on human TIGIT as any of TIG1, TIG2 or TIG3. In some embodiments of any of the embodiments disclosed herein, the antibody inhibits binding of CD155 to human TIGIT. In some embodiments, the antibody comprises three light chain CDRs and three heavy chain CDRs corresponding to three light chain and three heavy chain CDRs of any one of TIG1, TIG2 or TIG3. In some embodiments, the antibody comprises three heavy chain CDRs and three light chain CDRs of any one of TIG1, TIG2 or TIG3. In some embodiments, the antibody comprises three heavy chain CDRs as defined by Kabat and three light chain CDRs as defined by Kabat of any one of TIG1 (SEQ ID NOs: 15-17 light chain and 11-13 heavy chain), TIG2 (SEQ ID NOs. 23-25 light chain, 19-21 heavy chain) or TIG3 (SEQ ID NOs: 31-33 light chain and 27-29 heavy chain). In some embodiments of any of the embodiments disclosed herein, the antibody is chimeric, humanized, or veneered. In some embodiments, the antibody is a human antibody. In some embodiments of any of the embodiments disclosed herein, the antibody has human IgG1 kappa isotype. In some embodiments of any of the embodiments disclosed herein, the antibody is an intact antibody. In some embodiments of any of the embodiments disclosed herein, the antibody is a single-chain antibody, Fab or F(ab')2 fragment. In some embodiments of any of the embodiments disclosed herein, the antibody comprises a mature heavy chain variable region with at least 90% sequence identity to SEQ ID NO:35 and a mature light chain variable region with at least 90% sequence identity to SEQ ID NO:37. In some embodiments, the mature heavy chain variable region has at least 95 or 99% sequence identity to SEQ ID NO:35 and the mature light chain variable region has at least 95 or 99% sequence identity to SEQ ID NO:37. In some embodiments, the mature heavy chain variable region has the amino acid sequence of SEQ ID NO:35 and the mature light chain variable region has the amino acid sequence of SEQ ID NO:37. In some embodiments, the mature heavy chain variable region is linked to a heavy chain constant region comprising SEQ ID NO:40 provided that the C-terminal lysine may or may not be present, and the mature light chain variable region is linked to a light chain constant region comprising SEQ ID NO:41. In some embodiments, the mature heavy chain variable region is linked to a heavy chain constant region comprising SEQ ID NO:60 provided that the C-terminal lysine may or may not be present, and the mature light chain variable region is linked to a light chain constant region comprising SEQ ID NO:64. In some embodiments, the mature heavy chain variable region is linked to a heavy chain constant region comprising SEQ ID NO:61 provided that the C-terminal lysine may or may not be present, and the mature light chain variable region is linked to a light chain constant region comprising SEQ ID NO:64. In some embodiments of any of the embodiments disclosed herein, the antibody comprises a mature heavy chain variable region with at least 90% sequence identity to SEQ ID NO:43 and a mature light chain variable region with at least 90% sequence identity to SEQ ID NO:45. In some embodiments, the mature heavy chain variable region has at least 95 or 99% sequence identity to SEQ ID NO:43 and the mature light chain variable region has at least 95 or 99% sequence identity to SEQ ID NO:45. In some embodiments, the mature heavy chain variable region has the amino acid sequence of SEQ ID NO:43 and the mature light chain variable region has the amino acid sequence of SEQ ID NO:45. In some embodiments, the mature heavy chain variable region is linked to a heavy chain constant region comprising SEQ ID NO:48 provided that the C-terminal lysine may or may not be present, and the mature light chain variable region is linked to a light chain constant region comprising SEQ ID NO:49. In some embodiments, the mature heavy chain variable region is linked to a heavy chain constant region comprising SEQ ID NO:62 provided that the C-terminal lysine may or may not be present, and the mature light chain variable region is linked to a light chain constant region comprising SEQ ID NO:65. In some embodiments, the mature heavy chain variable region is linked to a heavy chain constant region comprising SEQ ID NO:63 provided that the C-terminal lysine may or may not be present, and the mature light chain variable region is linked to a light chain constant region comprising SEQ ID NO:65. In yet other aspects, provided herein is a monoclonal antibody that binds to an epitope comprising residues 35 and 37 of SEQ NO:1 and/or residues 49 and 51 of SEQ ID NO:1. In some embodiments, the antibody binds to an epitope comprising residues 35, 37, 49 and 51 of SEQ ID NO:1. In some embodiments, the antibody binds to a peptide consisting of residues 35-51 of SEQ ID NO:1 and no more than five flanking amino acids from SEQ ID NO:1 on either side. In some embodiments, the antibody binds to a peptide consisting of residues 35-51 of SEQ ID NO:1. In some embodiments, the epitope consists of 3 to 20 contiguous residues of SEQ ID NO:1. In some embodiments of any of the embodiments disclosed herein, the antibody has one or more of the following properties: (a) inhibiting binding of TIGIT to CD155, optionally with an IC50 of 15-100 ng/ml, (b) increases intrinsic T-cell activation in the presence of antigen presenting cells expressing CD155 as measured by IL-2 production, optionally 1.5-3 fold, (c) increases antigen-specific T-cell activation as measured by IL-12 production, optionally 1.5-3 fold, (d) increases natural killer cell activation as measured by production of any of IL-2, IL-6, TNFα or IFNγ, optionally by 1.5-3 fold, (e) increases T-cell production of at least one pro-inflammatory cytokine, optionally by 1.5-3 fold, and (f) reduces T-cell production of a least one anti-inflammatory cytokine, optionally by 1.5-3 fold.

In another aspect, provided herein are pharmaceutical compositions comprising any of the antibodies described herein and a pharmaceutically acceptable carrier.

In further aspects, provided herein are methods for treating or effecting prophylaxis of cancer comprising administering to a subject having or at risk of cancer an effective regime or a therapeutically effective amount of any of the antibodies disclosed herein. In some embodiments, the cancer is acute myeloid leukemia or adult T-cell leukemia. In some embodiments of any of the embodiments disclosed herein, the subject is administered tumor infiltrating T-cells which are activated by the antibody. In some embodiments of any of the embodiments disclosed herein, the subject is administered a vaccine inducing an immune response against the cancer, which is enhanced by the antibody. In some embodiments, the vaccine comprises an antigen or a fragment thereof expressed on the surface of cancer cells. In some embodiments of any of the embodiments disclosed herein, the subject is administered natural killer cells whose cytotoxicity against the cancer is enhanced by the antibody. In some embodiments of any of the embodiments disclosed herein, the subject is further administered a second antibody against an antigen expressed on the surface of cells of cancer, whereby an effector mediated cytotoxicity of the second antibody against the cancer is enhanced by the antibody. In some embodiments of any of the embodiments disclosed herein, the subject is further administered a second antibody against an antigen expressed on the surface of an immune cell. In some embodiments, the immune cell is a T-cell or a natural killer cell. In some embodiments of any of the embodiments disclosed herein, the antigen is CTLA-4, PD-1 or PD-L1. In some embodiments of any of the embodiments disclosed herein, the subject is further administered one or more therapies selected from the group consisting of chemotherapy, radiation, cell-based therapy, and surgery. In some embodiments of any of the embodiments disclosed herein, the subject is further administered an inhibitor of one or more immune-checkpoint receptors or ligands. In some embodiments, the inhibitor is selected from the group consisting of ipilimumab, nivolumab, pembrolizumab (lambrolizumab) and atezolizumab.

In additional aspects, provided herein are methods for treating a subject infected with a pathogen comprising administering to the subject an effective regime or a therapeutically effective amount of any of the antibodies disclosed herein. In some embodiments, the pathogen is a virus, bacteria, fungi, or protozoan. In some embodiments, the pathogen is HIV, SIV, hepatitis, herpes virus, adenovirus, influenza virus, flavivirus, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus, arboviral encephalitis virus, chlamydia, rickettsial bacteria, mycobacteria, staphylococci, treptocci, pneumonococci, meningococci, conococci, klebsiella, proteus, serratia, pseudomonas, legionella, diphtheria, salmonella, bacilli, cholera, tetanus, botulism, anthrax, plague, leptospirosis, and Lyme disease bacteria. In some embodiments of any of the embodiments disclosed herein, the subject is treated with a vaccine inducing an immune response against the pathogen which is enhanced by the antibody. In some embodiments, the vaccine comprises a protein of the pathogen or fragment thereof. In some embodiments of any of the embodiments disclosed herein, the subject is further administered a second antibody against the pathogen, wherein an effector mediated cytotoxicity of the second antibody against the pathogen is enhanced by the antibody. In some embodiments of any of the embodiments disclosed herein, the subject is further administered one or more of an antiviral agent, an antiparasitic agent, an antibacterial agent, or an antifungal agent.

In another aspect, provided herein are methods for aiding in the treatment of cancer comprising administering to a subject having cancer a therapeutically effective amount of any of the antibodies discloses herein. In some embodiments, the cancer is acute myeloid leukemia or adult T-cell leukemia. In some embodiments of any of the embodiments disclosed herein, the subject is administered tumor infiltrating T-cells which are activated by the antibody. In some embodiments of any of the embodiments disclosed herein, the subject is administered a vaccine inducing an immune response against the cancer, which is enhanced by the antibody. In some embodiments, the vaccine comprises an antigen expressed on the surface of cancer cells or a fragment thereof. In some embodiments of any of the embodiments disclosed herein, the subject is administered natural killer cells whose cytotoxicity against the cancer is enhanced by the antibody. In some embodiments of any of the embodiments disclosed herein, the subject is administered a second antibody against an antigen expressed on the surface of cells of cancer, whereby an effector mediated cytotoxicity of the second antibody against the cancer is enhanced by the antibody. In some embodiments of any of the embodiments disclosed herein, the subject is further administered a second antibody against an antigen expressed on the surface of an immune cell. In some embodiments, the immune cell is a T-cell or a natural killer cell. In some embodiments of any of the embodiments disclosed herein, the antigen is CTLA-4, PD-1 or PD-L1. In some embodiments of any of the embodiments disclosed herein, the subject is further administered one or more therapies selected from the group consisting of chemotherapy, radiation, cell-based therapy, and surgery. In some embodiments of any of the embodiments disclosed herein, the subject is further administered an inhibitor of one or more immune-checkpoint receptors or ligands. In some embodiments, the one or more immune-checkpoint receptors or ligands are selected from the group consisting of CTLA-4, PD-1 and PD-L1. In some embodiments, the inhibitor is selected from the group consisting of ipilimumab, nivolumab, pembrolizumab (lambrolizumab) and atezolizumab.

Each of the aspects and embodiments described herein are capable of being used together, unless excluded either explicitly or clearly from the context of the embodiment or aspect.

BRIEF DESCRIPTION OF THE DRAWINGS

FIG. 3 depicts the amino acid sequence of TIG1 VH.

FIG. 4 depicts the amino acid sequence of TIG1 VL.

FIG. 5 depicts the amino acid sequence of TIG2 VH.

FIG. 6 depicts the amino acid sequence of TIG2 VL.

FIG. 7 depicts the amino acid sequence of TIG3 VH.

FIG. 8 depicts the amino acid sequence of TIG3 VL.

FIG. 9A depicts the nucleotide sequence of the HuTIG1 VH gene and the encoded amino acid sequence while FIG. 9B depicts the nucleotide sequence of the HuTIG1 VL gene and the encoded amino acid sequence.

FIG. 14A depicts the nucleotide sequence of the HuTIG3 VH gene and the encoded amino acid sequence while FIG. 14B depicts the nucleotide sequence of the HuTIG3 VL gene and the encoded amino acid sequence.

FIG. 18 depicts expression of CD155 on K562 cells (top) and TIGIT on NK cells (bottom).

FIG. 32A depicts expression of TIGIT on tumor infiltrating lymphocytes from dissociated tumor samples. FIG. 32B depicts representative histograms of anti-TIGIT staining at various expression levels.

DETAILED DESCRIPTION

Figure 1:
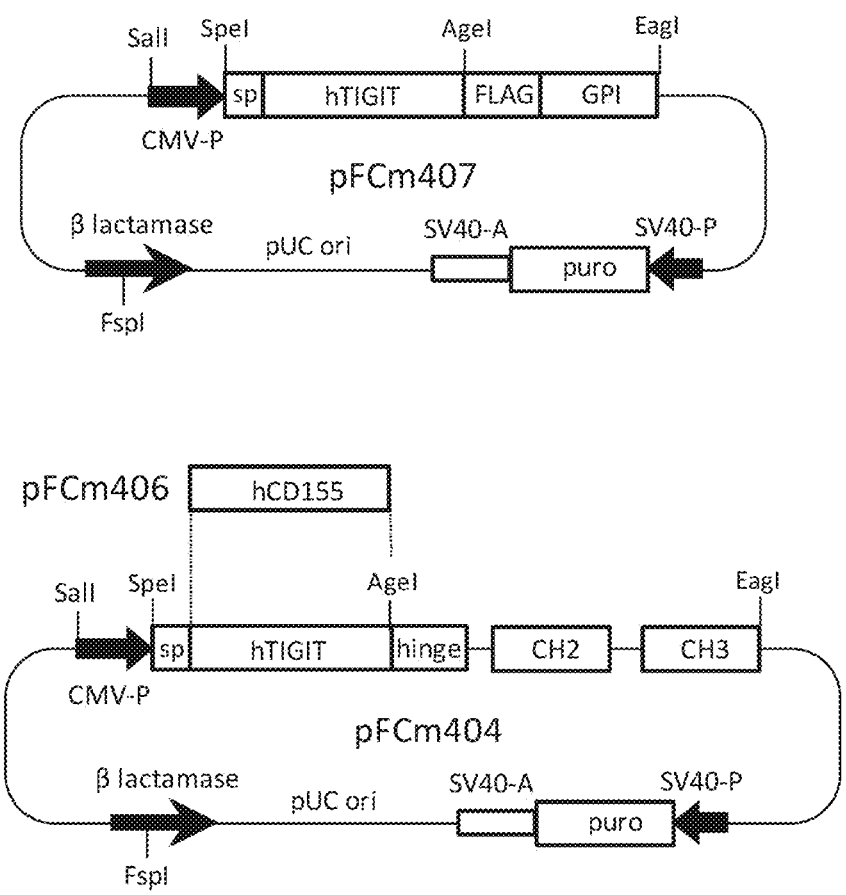
FIG. 1 is a schematic structure of expression vectors for recombinant TIGIT and CD155 proteins.

The invention provides, inter alia, monoclonal antibodies that specifically bind to the extracellular domain of TIGIT, which is a member of the immunoglobulin superfamily with an immunoreceptor tyrosine-based inhibitory motif (ITIM) in the cytoplasmic tail. The monoclonal antibodies inhibit binding of TIGIT to CD155 and can thereby activate T cells and/or NK cells. The monoclonal antibodies can be used for treatment of cancer and infectious disease, among other applications.

I. Definitions

Monoclonal antibodies or other biological entities, such as a fragment of TIGIT are typically provided in isolated form. This means that an antibody or other biologically entity is typically at least 50% w/w pure of interfering proteins and other contaminants arising from its production or purification but does not exclude the possibility that the monoclonal antibody is combined with an excess of pharmaceutical acceptable carrier(s) or other vehicle intended to facilitate its use. Sometimes monoclonal antibodies are at least 60, 70, 80, 90, 95 or 99% w/w pure of interfering proteins and contaminants from production or purification. Often an isolated monoclonal antibody or other biological entity agent is the predominant macromolecular species remaining after its purification.

Specific binding of a monoclonal antibody to its target antigen means an affinity (association constant or Ka) of at least $10^6$, $10^7$, $10^8$, $10^9$, or $10^{10}$ $M^{-1}$, determined by e.g., the assay of Example 15. Specific binding is detectably higher in magnitude and distinguishable from non-specific binding occurring to at least one unrelated target. Specific binding can be the result of formation of bonds between particular functional groups or particular spatial fit (e.g., lock and key type) whereas nonspecific binding is usually the result of van der Waals forces. Specific binding does not however necessarily imply that a monoclonal antibody binds one and only one target.

The basic antibody structural unit is a tetramer of subunits. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. This variable region is initially expressed linked to a cleavable signal peptide. The variable region without the signal peptide is sometimes referred to as a mature variable region. Thus, for example, a light chain mature variable region, means a light chain variable region without the light chain signal peptide. The carboxy-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 or more amino acids. (See generally, *Fundamental Immunology* (Paul, W., ed., 2nd ed. Raven Press, N.Y., 1989), Ch. 7) (incorporated by reference in its entirety for all purposes).

The mature variable regions of each light/heavy chain pair form the antibody binding site. Thus, an intact antibody has two binding sites. Except in bifunctional or bispecific antibodies, the two binding sites are the same. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, 1-R3, CDR3 and FR4. The assignment of amino acids to each domain is in accordance with the definitions of Kabat, *Sequences of Proteins of Immunological Interest* (National Institutes of Health, Bethesda, Md., 1987 and 1991), or Chothia & Lesk, *J. Mol. Biol.* 196:901-917 (1987); Chothia et al., *Nature* 342:878-883 (1989). Kabat also provides a widely used numbering convention (Kabat numbering) in which corresponding residues between different heavy chains or between different light chains are assigned the same number.

The term "antibody" includes intact antibodies and binding fragments thereof. Thus, any reference to an antibody should be understood to refer to the antibody in intact form or a binding fragment unless the context requires otherwise. Typically, fragments compete with the intact antibody from which they were derived for specific binding to the target including separate heavy chains, light chains Fab, Fab', F(ab')$_2$, F(ab)$_c$, Dabs, nanobodies, and scFv, diabodies, scFv-Fc, minibodies, IgNARs, V-NAR, hcIgG, bis-scFv, triabodies, and tetrabodies. Fragments can be produced by recombinant DNA techniques, or by enzymatic or chemical separation of intact immunoglobulins. The term "antibody" also includes a bispecific antibody. A bispecific or bifunctional antibody is an artificial hybrid antibody having two different heavy/light chain pairs and two different binding sites (see, e.g., Songsivilai and Lachmann, *Clin. Exp. Immunol.*, 79:315-321 (1990); Kostelny et al., *J. Immunol.*, 148: 1547-53 (1992)).

The term "epitope" refers to a site on an antigen to which an antibody binds. An epitope can be formed from contiguous amino acids or noncontiguous amino acids juxtaposed by tertiary folding of one or more proteins. Epitopes formed from contiguous amino acids (also known as linear epitopes) are typically retained on exposure to denaturing solvents whereas epitopes formed by tertiary folding (also known as conformational epitopes) are typically lost on treatment with denaturing solvents. An epitope typically includes at least 3, and more usually, at least 5 or 8-10 amino acids in a unique spatial conformation. Methods of determining spatial conformation of epitopes include, for example, X-ray crystallography and 2-dimensional nuclear magnetic resonance. See, e.g., Epitope Mapping Protocols, in *Methods in Molecular Biology*, Vol. 66, Glenn E. Morris, Ed. (1996).

Antibodies that recognize the same or overlapping epitopes can be identified in a simple immunoassay showing the ability of one antibody to compete with the binding of another antibody to a target antigen. The epitope of an antibody can also be defined by X-ray crystallography of the antibody bound to its antigen to identify contact residues. Alternatively, two antibodies have the same epitope if all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Competition between antibodies is determined by an assay in which an antibody under test conditions inhibits the specific binding of a reference antibody to a common antigen (see, e.g., Junghans et al., *Cancer Res.* 50:1495, 1990). A test antibody competes with a reference antibody if an excess of a test antibody (e.g., at least 2×, 3×, 4×, 5×, 6×, 7×, 8×, 9×, 10×, 15×, 20×, 25×, 30×, 35×, 40×, 45×, 50×, 60×, 70×, 80×, 90×, 100×, or more, inclusive of numbers falling in between these values) inhibits binding of the reference antibody by at least 50% but preferably 75%, 90%, or 99%. In other embodiments, a test antibody competes with a reference antibody if an excess of a test antibody inhibits binding of the reference antibody by any of at least about 55%, 60%, 65%, 70%, or preferably at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% as measured in a competitive binding assay. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Preferably competition is assessed as in Example 14.

The term "subject" includes human and other mammalian subjects. In some cases, the methods of the invention find use in experimental animals, in veterinary application, and in the development of animal models for disease, including, but not limited to, rodents including mice, rats, hamsters as well as primates, such as simians. In some embodiments, subjects receive or are candidates to receive either prophylactic or therapeutic treatment.

As used herein, an amino acid residue of an amino acid sequence of interest that "corresponds to" or is "corresponding to" or in "correspondence with" an amino acid residue of a reference amino acid sequence indicates that the amino acid residue of the sequence of interest is at a location homologous or equivalent to an enumerated residue in the reference amino acid sequence. One skilled in the art can determine whether a particular amino acid residue position in a polypeptide, such as a TIGIT polypeptide, corresponds to that of a homologous reference sequence. For example, the sequence of a TIGIT polypeptide may be aligned with that of a reference sequence using known techniques (e.g., basic local alignment search tool (BLAST), ClustalW2, Structure based sequences alignment program (STRAP), or the like). In addition, crystal structure coordinates of a reference sequence may be used as an aid in determining a homologous polypeptide residue's three dimensional structure (Stengel et al., *Proc Natl. Acad. Sci. USA*, 109:5399-5404, 2012. In another aspect, equivalent residues may be identified by determining homology at the level of tertiary structure. Using such methods, the amino acid residues of a TIGIT polypeptide variant may be numbered according to the corresponding amino acid residue position numbering of the reference sequence. For example, the amino acid sequence of SEQ ID NO: 1 may be used for determining amino acid residue position numbering of each amino acid residue of a TIGIT variant of interest or epitope. In some embodiments, one amino acid sequence corresponds to another amino acid sequence if it shares at least about 80%, 81%, 82%, 83%, 84%, 85%, 86%, 87%, 88%, 89%, 90%, 91%, 92%, 93%, 94%, 95%, 96%, 97%, 98%, 99%, or 100% sequence identity.

For purposes of classifying amino acids substitutions as conservative or nonconservative, amino acids are grouped as follows: Group I (hydrophobic side chains): met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Percentage sequence identities are determined with antibody sequences maximally aligned by the Kabat numbering convention. After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

Compositions or methods "comprising" one or more recited elements may include other elements not specifically recited. For example, a composition that comprises antibody may contain the antibody alone or in combination with other ingredients.

Unless otherwise apparent from the context, reference to a range includes all integers within the range and all subranges defined by such integers.

II. Target Molecules

Unless otherwise indicated TIGIT means human TIGIT. An exemplary human sequence is assigned Swiss-Prot accession number Q495A1. The complete human TIGIT sequence has 244 amino acids of which amino acids 1-21 are a signal peptide and 22-244 constitute the mature protein (SEQ ID NO:1). Approximately residues 22-141 constitute an extracellular domain (SEQ ID NO:3). Approximately residues 142-162 constitute a transmembrane domain, and approximately residues 163-244 constitute a cytoplasmic domain.

Unless otherwise indicated CD155 refers to the human form of this protein. An exemplary human sequence for human CD155 is designated Swiss-Prot P15151, which is a protein of 417 amino acids of which approximately residues 1-20 are a signal peptide, 21-343 are an extracellular domain (SEQ ID NO:6), 344-367 are a transmembrane domain, and 368-417 are a cytoplasmic domain.

Unless otherwise apparent from the context, reference to one of the above proteins means at least the extracellular domain of the protein and usually the complete protein other than a cleavable signal peptide.

III. Antibodies of the Invention

A. Binding Specificity and Functional Properties

The invention provides monoclonal antibodies binding to epitopes within the extracellular domain of TIGIT protein. Antibodies designated TIG1, TIG2, and TIG3 are three such exemplary mouse antibodies. The sequences of the heavy and light chain mature variable regions of these antibodies are designated SEQ ID NOs. 10 and 14, 18 and 22, and 26 and 30 respectively TIG1, TIG2, and TIG3 specifically bind to the extracellular domain of human TIGIT.

Some antibodies of the invention bind to the same or overlapping epitope as an antibody designated TIG1, TIG2, or TIG3. Other antibodies having such a binding specificity can be produced by immunizing mice with TIGIT or a portion thereof including the desired epitope, and screening resulting antibodies for binding to the extracellular domain of TIGIT, optionally in competition with TIG1, TIG2, or TIG3. Antibodies can also be screened against mutagenized forms of the TIGIT antigen to identify an antibody showing the same or similar binding profile to collection of mutational changes as TIG1, TIG2, or TIG3. The mutations can be systematic replacement substitution with alanine (or serine if an alanine is present already) one residue at a time, or more broadly spaced intervals, throughout the extracellular domain of TIGIT antibody or through a section thereof in which an epitope is known to reside.

Example 16 maps residues 35, 37, 49 and 51 of SEQ ID NO:1 as being residues forming the epitope of the TIG1 antibody. Alanine substitution at any one of these residues essentially abolishes binding of the antibody. The invention thus includes other antibodies binding to an epitope of human TIGIT comprising residues 35 and 37 of SEQ NO:1 and/or residues 49 and 51 of SEQ ID NO:1, and preferably an epitope including all of these residues. The epitope can be linear (e.g., 3-20, 3-17, or 5-10 contiguous residues) or conformational. Some such antibodies bind to a peptide consisting of residues 35-51 of SEQ ID NO:1 and no more than 1, 2, 3, 4 or 5 flanking amino acids from SEQ ID NO:1 on either side. Some such antibodies bind to a peptide consisting of residues 35-51 of SEQ ID NO:1. Some such antibodies can be generated by immunization with such peptides. Example 19 also reveals that residue 90 of SEQ ID NO:1 is critical for the binding of the humanized (Hu)TIG1 antibody to TIGIT, in addition to residues 35, 37, 49 and 51 of SEQ ID NO:1. In other embodiments, the antibody (such as a HuTIG1 antibody) binds to an epitope comprising one or more of residues corresponding to amino acid positions 35, 37, 49, 51, and/or 90 of SEQ ID NO:1. In further embodiments, the antibody (such as a HuTIG1 antibody) does not bind to one or more residues corresponding to amino acid positions 34, 39, 44, 47, 52, 55, 86, 88, 92, and/or 96 of SEQ ID NO:1.

Antibodies having the binding specificity of a selected murine antibody (e.g., TIG1, TIG2, or TIG3) can also be produced using a variant of the phage display method. See Winter, WO 92/20791. This method is particularly suitable for producing human antibodies. In this method, either the heavy or light chain variable region of the selected murine antibody is used as a starting material. If, for example, a light chain variable region is selected as the starting material, a phage library is constructed in which members display the same light chain variable region (i.e., the murine starting material) and a different heavy chain variable region. The heavy chain variable regions can for example be obtained from a library of rearranged human heavy chain variable regions. A phage showing strong specific binding for TIGIT (e.g., at least $10^8$ and preferably at least $10^9$ $M^{-1}$) is selected. The heavy chain variable region from this phage then serves as a starting material for constructing a further phage library. In this library, each phage displays the same heavy chain variable region (i.e., the region identified from the first display library) and a different light chain variable region. The light chain variable regions can be obtained for example from a library of rearranged human variable light chain regions. Again, phage showing strong specific binding for TIGIT are selected. The resulting antibodies usually have the same or similar epitope specificity as the murine starting material.

Some antibodies have a mature heavy chain variable region comprising CDRs H1, H2 and H3 and a mature light chain region comprising CDRs L1, L2 and L3 entirely or substantially from TIG1. Some antibodies have a mature heavy chain variable region comprising CDRs H1, H2 and H3 and a mature light chain region comprising CDRs L1, L2 and L3 entirely or substantially from TIG2. Some antibodies have a mature heavy chain variable region comprising CDRs H1, H2 and H3 and a mature light chain region comprising CDRs L1, L2 and L3 entirely or substantially from TIG3. CDRs can be defined by any conventional definition including Kabat, Chothia, Kabat and Chothia composite, AbM or Contact definition as shown in the table below:

Other antibodies can be obtained by mutagenesis of cDNA encoding the heavy and light chains of an exemplary antibody, such as TIG1, TIG2, or TIG3. Monoclonal antibodies that are at least any of about 80%, 81%, 82%, 83%, 84%, 85%, 86%, 87%, 88%, 89%, 90%, 91%, 92%, 93%, 94%, 95%, 96%, 97%, 98%, 99% or 100% identical to TIG1, TIG2, or TIG3 in amino acid sequence of the mature heavy and/or light chain variable regions and maintain its functional properties, and/or which differ from the respective antibody by a small number of functionally inconsequential amino acid substitutions (e.g., conservative substitutions), deletions, or insertions are also included in the invention Amino acids in the variable region frameworks likely important for binding can be identified as described in the sections on humanization below. Monoclonal antibodies having at least one and preferably all six CDR(s) as defined by Kabat that are any of about 80%, 81%, 82%, 83%, 84%, 85%, 86%, 87%, 88%, 89%, 90%, 91%, 92%, 93%, 94%, 95%, 96%, 97%, 98%, 99% or 100% identical to corresponding CDRs of TIG1, TIG2, or TIG3 are also included.

Antibodies preferably have one or more of the following characteristics (i) inhibiting binding of human TIGIT to human CD155, (ii) inhibiting binding of TIGIT to other ligands, such as CD112, and CD113, (iii) increasing antigen-specific T-cell responses, (iv) activating natural killer cells, (v) stimulating intrinsic T-cell activations, and (vi) stimulating production of one or more immunostimulatory cytokines and/or reducing production of one or more immunosuppressive cytokines by T-cells and other cells of the immune system. Exemplary assays for measuring these properties are provided in the examples.

Preferred antibodies completely or partially inhibit binding of TIGIT to CD155. Some antibodies can inhibit such interaction with an $IC_{50}$ of any of about 25-300 ng/ml, 25-75 ng/ml, 25-50 ng/ml, 40-75 ng/ml, 50-75 ng/ml, 50-90 ng/ml, 50-100 ng/ml, 75-100 ng/ml, 50-150 ng/ml, 75-175 ng/ml, 100-200 ng/ml, 125-225 ng/ml, 100-250 ng/ml, 150-300 ng/ml, 175-250 ng/ml, 200-300 ng/ml, 25-275 ng/ml, 250-300 ng/ml, 49+/−10% ng/ml, 65+/−10% ng/ml or 76+/−10% ng/ml, measured as in the Examples. In other embodiments, the antibodies can completely or partially inhibit binding of TIGIT to CD155 with an $IC_{50}$ of any of at least about 25 ng/ml, 50 ng/ml, 75 ng/ml, 100 ng/ml, 125 ng/ml, 150 ng/ml, 175 ng/ml, 200 ng/ml, 225 ng/ml, 250 ng/ml, 275 ng/ml, or 300 ng/ml, or more, inclusive of concentrations falling in between these values. Some antibodies can increase antigen-specific T-cell responses by 1.5-3 fold, such as any of about 1.5, 1.6, 1.7, 1.8, 1.9, 2, 2.1, 2.2, 2.3, 2.4, 2.5, 2.6, 2.7, 2.8, 2.9, or 3 fold or more, as measured in the Examples. Some antibodies can increase production of 1, 2, 3 or all of IL-2, IL-6, TNFα and IFNγ by NK cells by 1.5 to 3 fold, such as any of about 1.5, 1.6, 1.7, 1.8, 1.9, 2, 2.1, 2.2, 2.3, 2.4, 2.5, 2.6, 2.7, 2.8, 2.9, or 3 fold or more, as measured in the examples. Some antibodies can increase intrinsic T-cell

| Loop | Kabat | AbM | Chothia | Contact |
| --- | --- | --- | --- | --- |
| L1 | L-24 - - - L34 | L24 - - - 34 | L24 - - - L34 | L30 - - - L36 |
| L2 | L50 - - - L56 | L50 - - - l56 | L50 - - - L56 | L46 - - - L55 |
| L3 | L89 - - - L97 | L89 - - - 97 | L89 - - - L97 | L89 - - - L96 |
| H1 | H31 - - - H35B (Kabat Numbering) | H26 - - - H35b | H26 - - - H32 . . . 34 | H30 - - - H35B |
| H1 | H31-H35 (Chothia Numbering) | H26 - - - H35 | H26 - - - H32 | H30 - - - H35 |
| H2 | H50 - - - H65 | H50 - - - H58 | H52 - - - H56 | H47 - - - H58 |
| H3 | H95 - - - H102 | H95 - - - H102 | H95 - - - H102 | H93 - - - H10 | activation by 1.5-3 fold, such as any of about 1.5, 1.6, 1.7, 1.8, 1.9, 2, 2.1, 2.2, 2.3, 2.4, 2.5, 2.6, 2.7, 2.8, 2.9, or 3 fold or more, as measured in the examples. Some antibodies can inhibit a cancer or an infectious disease as shown in an animal model or clinical trial. Animal models of cancer in which human cancer cells are injected into an immunodeficient laboratory animal, such as a mouse or rat, are widely available.

Humanizing or chimerizing antibodies increases in vivo half-life relative to starting mouse antibodies. The resulting half-life can be 10-50 days for example in humans. Half-live can be measured by pharmacokinetic studies, such as described by Kim et al, *Eur J of Immunol* 24:542 (1994).

B. Non-Human Antibodies

The production of other non-human monoclonal antibodies, e.g., murine, guinea pig, primate, rabbit, chicken or rat, against TIGIT can be accomplished by, for example, immunizing the animal with TIGIT or a fragment thereof, or cells bearing TIGIT. See Harlow & Lane, *Antibodies, A Laboratory Manual* (CSHP NY, 1988) (incorporated by reference for all purposes). Such an immunogen can be obtained from a natural source, by peptide synthesis or by recombinant expression. Optionally, the immunogen can be administered fused or otherwise complexed with a carrier protein. Optionally, the immunogen can be administered with an adjuvant. Several types of adjuvant can be used as described below. Complete Freund's adjuvant followed by incomplete adjuvant is preferred for immunization of laboratory animals. Rabbits or guinea pigs are typically used for making polyclonal antibodies. Mice are typically used for making monoclonal antibodies. Antibodies are screened for specific binding to TIGIT. Optionally, antibodies are further screened for binding to a specific region of TIGIT. Such screening can be accomplished by determining binding of an antibody to a collection of deletion mutants of TIGIT and determining which deletion mutants bind to the antibody. Binding can be assessed, for example, by Western blot, FACS or ELISA.

C. Humanized Antibodies

Reduction or elimination of a HAMA (human anti-mouse (also applicable to human anti-rat or human anti-rabbit or human anti-hamster, etc.) antibody) response is a significant aspect of clinical development of suitable therapeutic agents. See, e.g., Khaxzaeli et al., *J. Natl. Cancer Inst.* (1988), 80:937; Jaffers et al., *Transplantation* (1986), 41:572; Shawler et al., *J. Immunol.* (1985), 135:1530; Sears et al., *J. Biol. Response Mod.* (1984), 3:138; Miller et al., *Blood* (1983), 62:988; Hakimi et al., *J. Immunol.* (1991), 147:1352; Reichmann et al., *Nature* (1988), 332:323; Junghans et al., *Cancer Res.* (1990), 50:1495. As described herein, the invention provides antibodies that are humanized such that a HAMA response is reduced or eliminated. Variants of these antibodies can further be obtained using routine methods known in the art, some of which are further described below.

A humanized antibody is a genetically engineered antibody in which the CDRs from a non-human "donor" antibody are grafted into human "acceptor" antibody sequences (see, e.g., Queen, U.S. Pat. Nos. 5,530,101 and 5,585,089; Winter, U.S. Pat. No. 5,225,539, Carter, U.S. Pat. No. 6,407,213, Adair, U.S. Pat. No. 5,859,205 6,881,557, Foote, U.S. Pat. No. 6,881,557). The acceptor antibody sequences can be, for example, a mature human antibody sequence, a composite of such sequences, a consensus sequence of human antibody sequences, or a germline region sequence. Thus, a humanized antibody is an antibody having some or all CDRs entirely or substantially from a donor antibody and variable region framework sequences and constant regions, if present, entirely or substantially from human antibody sequences. Similarly, a humanized heavy chain has at least one, two and usually all three CDRs entirely or substantially from a donor antibody heavy chain, and a heavy chain variable region framework sequence and heavy chain constant region, if present, substantially from human heavy chain variable region framework and constant region sequences. Similarly, a humanized light chain has at least one, two and usually all three CDRs entirely or substantially from a donor antibody light chain, and a light chain variable region framework sequence and light chain constant region, if present, substantially from human light chain variable region framework and constant region sequences. Other than nanobodies and dAbs, a humanized antibody comprises a humanized heavy chain and a humanized light chain. Here as elsewhere in the application, a CDR in a subject antibody is substantially from a corresponding CDR in a reference antibody when at least about 80%, 81%, 82%, 83%, 84%, 85%, 86%, 87%, 88%, 89%, 90%, 91%, 92%, 93%, 94%, 95%, 96%, 97%, 98%, 99% or 100% of corresponding residues (as defined by Kabat) are identical between the respective CDRs; however, a CDR H2 as defined by Kabat in a subject antibody is substantially from a corresponding CDR in a reference antibody when at least about 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% of corresponding residues (as defined by Kabat) are identical between the respective CDRs. The variable region framework sequences of an antibody chain or the constant region of an antibody chain are substantially from a human variable region framework sequence or human constant region respectively when at least about 80%, 81%, 82%, 83%, 84%, 85%, 86%, 87%, 88%, 89%, 90%, 91%, 92%, 93%, 94%, 95%, 96%, 97%, 98%, 99% or 100% of corresponding residues defined by Kabat are identical.

Although humanized antibodies often incorporate all six CDRs (preferably as defined by Kabat) from a non-human (e.g. mouse) antibody, they can also be made with less than all CDRs (e.g., at least 3, 4, or 5) CDRs from a non-human antibody (e.g., Pascalis et al., *J. Immunol.* 169:3076, 2002; Vajdos et al., *Journal of Molecular Biology,* 320: 415-428, 2002; Iwahashi et al., *Mol. Immunol.* 36:1079-1091, 1999; Tamura et al, *Journal of Immunology,* 164:1432-1441, 2000).

In some antibodies only part of the CDRs, namely the subset of CDR residues required for binding, termed the SDRs, are needed to retain binding in a humanized antibody. CDR residues not contacting antigen and not in the SDRs can be identified based on previous studies (for example residues H60-H65 in CDR H2 are often not required), from regions of Kabat CDRs lying outside Chothia hypervariable loops (Chothia, *J. Mol. Biol.* 196:901, 1987), by molecular modeling and/or empirically, or as described in Gonzales et al., *Mol. Immunol.* 41: 863, 2004. In such humanized antibodies at positions in which one or more donor CDR residues is absent or in which an entire donor CDR is omitted, the amino acid occupying the position can be an amino acid occupying the corresponding position (by Kabat numbering) in the acceptor antibody sequence. The number of such substitutions of acceptor for donor amino acids in the CDRs to include reflects a balance of competing considerations. Such substitutions are potentially advantageous in decreasing the number of mouse amino acids in a humanized antibody and consequently decreasing potential immunogenicity. However, substitutions can also cause changes of affinity, and significant reductions in affinity are preferably avoided. Positions for substitution within CDRs and amino acids to substitute can also be selected empirically.

While the acceptor may be identical in sequence to the human framework sequence selected, whether that is from a human immunoglobulin or a human consensus framework, the present invention contemplates that the acceptor sequence may comprise pre-existing amino acid substitutions relative to the human immunoglobulin sequence or human consensus framework sequence. These pre-existing substitutions are preferably minimal; usually four, three, two or one amino acid differences only relative to the human immunoglobulin sequence or consensus framework sequence.

The human acceptor antibody sequences can optionally be selected from among the many known human antibody sequences to provide a high degree of sequence identity (e.g., 65-85% identity) between a human acceptor sequence variable region frameworks and corresponding variable region frameworks of a donor antibody chain.

Certain amino acids from the human variable region framework residues can be selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

For example, when an amino acid differs between a non-human variable region framework residue and a selected human variable region framework residue, the human framework amino acid can be substituted by the equivalent framework amino acid from the non-human antibody when it is reasonably expected that the amino acid:
(1) noncovalently binds antigen directly,
(2) is adjacent to a CDR region,
(3) otherwise interacts with a CDR region (e.g. is within about 6 Å of a CDR region).

Other candidates for substitution are acceptor human framework amino acids that are unusual for a human immunoglobulin at that position. These amino acids can be substituted with amino acids from the equivalent position of the non-human donor antibody or from the equivalent positions of more typical human immunoglobulins. Other candidates for substitution are acceptor human framework amino acids that are unusual for a human immunoglobulin at that position.

A preferred humanized antibody has a mature heavy chain variable region at least about 80%, 81%, 82%, 83%, 84%, 85%, 86%, 87%, 88%, 89%, 90%, 91%, 92%, 93%, 94%, 95%, 96%, 97%, 98%, 99%, or less than 100% identical to SEQ ID NO:35 and a mature light chain variable region at least about 80%, 81%, 82%, 83%, 84%, 85%, 86%, 87%, 88%, 89%, 90%, 91%, 92%, 93%, 94%, 95%, 96%, 97%, 98%, 99%, or less than 100% identical to SEQ ID NO:37. Preferably any variation occurs at variable region framework residues other than those identified as likely important to binding. Preferably any variation is a conservative amino acid substitution. A preferred antibody comprises a mature heavy chain variable region with the sequence of SEQ ID NO:35 and a mature light chain variable region with the sequence of SEQ ID NO:37. For expression of a full length antibody, the mature heavy chain variable region is preferably linked to a heavy chain constant region consisting of or comprising SEQ ID NO:40 provided the C-terminal lysine may or may not be present and the mature light chain variable region is preferably linked to a light chain constant region consisting of or comprising SEQ ID NO:41.

Another preferred humanized antibody has a mature heavy chain variable region at least about 80%, 81%, 82%, 83%, 84%, 85%, 86%, 87%, 88%, 89%, 90%, 91%, 92%, 93%, 94%, 95%, 96%, 97%, 98%, 99%, or less than 100% identical to SEQ ID NO:43 and a mature light chain variable region at least about 80%, 81%, 82%, 83%, 84%, 85%, 86%, 87%, 88%, 89%, 90%, 91%, 92%, 93%, 94%, 95%, 96%, 97%, 98%, 99%, or less than 100% identical to SEQ ID NO:45. Preferably any variation occurs at variable region framework residues other than those identified as likely important to binding (see the Examples). Preferably any variation is a conservative amino acid substitution. A preferred antibody comprises a mature heavy chain variable region having the sequence of SEQ ID NO:43 and a mature light chain variable region having the sequence of SEQ ID NO:45. For expression of a full length antibody, the mature heavy chain variable region is preferably linked to a heavy chain constant region consisting of or comprising SEQ ID NO:48 provided the C-terminal lysine may or may not be present and the mature light chain variable region is preferably linked to a light chain constant region consisting of or comprising SEQ ID NO:49.

D. Chimeric and Veneered Antibodies

The invention further provides chimeric and veneered forms of non-human antibodies, particularly the TIG1, TIG2, and TIG3 antibodies of the examples.

A chimeric antibody is an antibody in which the mature variable regions of light and heavy chains of a non-human antibody (e.g., a mouse) are combined with human light and heavy chain constant regions. Such antibodies substantially or entirely retain the binding specificity of the non-human antibody, and are about two-thirds human sequence.

A veneered antibody is a type of humanized antibody that retains some and usually all of the CDRs and some of the non-human variable region framework residues of a non-human antibody but replaces other variable region framework residues that may contribute to B- or T-cell epitopes, for example exposed residues (Padlan, *Mol. Immunol.* 28:489, 1991) with residues from the corresponding positions of a human antibody sequence. The result is an antibody in which the CDRs are entirely or substantially from a non-human antibody and the variable region frameworks of the non-human antibody are made more human-like by the substitutions. Veneered forms of the TIG1, TIG2, or TIG3 antibody are included in the invention.

E. Human Antibodies

Human antibodies against TIGIT are provided by a variety of techniques described below. Some human antibodies are selected by competitive binding experiments, by the phage display method of Winter, above, or otherwise, to have the same epitope specificity as a particular mouse antibody, such as one of the mouse monoclonal antibodies described in the examples. Human antibodies can also be screened for a particular epitope specificity by using only a fragment of TIGIT as the target antigen, and/or by screening antibodies against a collection of deletion mutants of TIGIT.

Methods for producing human antibodies include the trioma method of Oestberg et al., *Hybridoma* 2:361-367 (1983); Oestberg, U.S. Pat. No. 4,634,664; and Engleman et al., U.S. Pat. No. 4,634,666, use of transgenic mice including human immunoglobulin genes (see, e.g., Lonberg et al., WO93/12227 (1993); U.S. Pat. Nos. 5,877,397, 5,874,299, 5,814,318, 5,789,650, 5,770,429, 5,661,016, 5,633,425, 5,625,126, 5,569,825, 5,545,806, *Nature* 148, 1547-1553 (1994), *Nature Biotechnology* 14, 826 (1996), Kucherlapati, WO 91/10741 (1991) and phage display methods (see, e.g., Dower et al., WO 91/17271 and McCafferty et al., WO 92/01047, U.S. Pat. Nos. 5,877,218, 5,871,907, 5,858,657, 5,837,242, 5,733,743 and 5,565,332).

F. Selection of Constant Region

The heavy and light chain variable regions of chimeric, humanized (including veneered), or human antibodies can be linked to at least a portion of a human constant region. The choice of constant region depends, in part, whether antibody-dependent complement and/or cellular mediated cytotoxicity is desired. For example, human isotopes IgG1 and IgG3 have complement-mediated cytotoxicity and human isotypes IgG2 and IgG4 do not. Light chain constant regions can be lambda or kappa. For immunotherapy against cancer or a pathogen not expressing TIGIT, human IgG2 or IgG4 or an attenuated form of human IgG1 with reduced effector function is often preferred. For human IgG4, inclusion of an S228P (Eu numbering) engineered mutation on the heavy chain to prevent Fab-arm exchange is often preferred. However, for elimination of cancer cells expressing TIGIT (e.g., tumors of T-cells or NK cells) or for immunosuppression, human IgG1 or IgG3 is often preferred.

Human constant regions show allotypic variation and isoallotypic variation between different individuals, that is, the constant regions can differ in different individuals at one or more polymorphic positions. Isoallotypes differ from allotypes in that sera recognizing an isoallotype bind to a non-polymorphic region of a one or more other isotypes. Reference to a human constant region includes a constant region with any natural allotype or any permutation of residues occupying polymorphic positions in natural allotypes.

One or several amino acids at the amino or carboxy terminus of the light and/or heavy chain, such as the C-terminal lysine of the heavy chain, may be missing or derivatized in a proportion or all of the molecules. Substitutions can be made in the constant regions to reduce or increase effector function such as complement-mediated cytotoxicity or ADCC (see, e.g., Winter et al., U.S. Pat. No. 5,624,821; Tso et al., U.S. Pat. No. 5,834,597; and Lazar et al., *Proc. Natl. Acad. Sci. USA*, 103:4005, 2006), or to prolong half-life in humans (see, e.g., Hinton et al., *J. Biol. Chem.* 279:6213, 2004). Exemplary substitutions include a Gln at position 250 and/or a Leu at position 428 (Eu numbering) for increasing the half-life of an antibody.

Some antibodies of the invention are engineered by introduction of constant region mutation(s) to have reduced effector functions, such as CDC and ADCC or ADCP compared with the same antibody without the mutation(s). Preferably, each or all of these effector functions are reduced at least 50%, 75%, 90% or 95% compared with antibodies without the mutation. The present examples show how to measure CDC. Other assays are described by Shields et al, 2001 J. Biol. Chem., Vol. 276, p 6591-6604; Chappel et al, 1993 *J. Biol. Chem.*, Vol 268, p 25124-25131; Lazar et al, 2006 PNAS, 103; 4005-4010.

Substitution of any or all of positions 234, 235, 236 and/or 237 reduces affinity for Fcγ receptors, particularly FcγRI receptor (see, e.g., U.S. Pat. No. 6,624,821). Alanine is a preferred residue for substitution and L234A/L235A is a preferred dual mutation to reduce effector function. Other combinations of mutations with reduced effector functions include L234A/L235A/G237A, E233P/L234V/L235A/G236, A327G/A330S/P331S, K322A, L234A and L235A, L234F/L235E/P331S. Optionally, positions 234, 236 and/or 237 in human IgG2 are substituted with alanine and position 235 with glutamine. (see, e.g., U.S. Pat. No. 5,624,821.) Two amino acid substitutions in the complement C1q binding site at EU index positions 330 and 331 reduce complement fixation (see Tao et al., J. Exp. Med. 178:661 (1993) and Canfield and Morrison, *J. Exp. Med.* 173:1483 (1991)). Substitution into human IgG1 of IgG2 residues at positions 233-236 and IgG4 residues at positions 327, 330 and 331 greatly reduces ADCC and CDC (see, for example, Armour K L. et al., 1999 *Eur J Immunol*. 29(8):2613-24; and Shields R L. et al., 2001. *J Biol Chem.* 276(9):6591-604). N297A, N297Q, or N297G (Eu numbering) mutations reduce glycosylation and thereby effector functions.

G. Expression of Recombinant Antibodies

Chimeric, humanized (including veneered) and human antibodies are typically produced by recombinant expression. Recombinant polynucleotide constructs typically include an expression control sequence operably linked to the coding sequences of antibody chains, including naturally-associated or heterologous promoter regions. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the recombinant antibodies.

Mammalian cells are a preferred host for expressing nucleotide segments encoding immunoglobulins or fragments thereof. See Winnacker, From Genes to Clones, (VCH Publishers, N Y, 1987). A number of suitable host cell lines capable of secreting intact heterologous proteins have been developed in the art, and include CHO cell lines, various COS cell lines, HeLa cells, HEK293 cells, L cells, and non-antibody-producing myelomas including Sp2/0 and NS0. Preferably, the cells are nonhuman. Expression vectors for these cells can include expression control sequences, such as an origin of replication, a promoter, an enhancer (Queen et al., *Immunol. Rev.* 89:49 (1986)), and necessary processing information sites, such as ribosome binding sites, RNA splice sites, polyadenylation sites, and transcriptional terminator sequences. Preferred expression control sequences are promoters derived from endogenous genes, cytomegalovirus, SV40, adenovirus, bovine papillomavirus, and the like. See Co et al., *J. Immunol.* 148:1149 (1992).

Once expressed, antibodies can be purified according to standard procedures of the art, including HPLC purification, column chromatography, gel electrophoresis and the like (see generally, Scopes, Protein Purification (Springer-Verlag, NY, 1982)).

IV. Therapeutic Applications

The antibodies can be used for enhancing immune responses in the treatment of cancer and infectious diseases. Disorders treatable by antibodies of the invention include, without limitation, cancers, including hematological malignancies and solid tumors. Such cancers may or may not express TIGIT or CD155. Antibodies to TIGIT are effective against cancers not expressing TIGIT because inhibition of TIGIT interaction with CD155 stimulates an immune response against such cancers. Examples of hematological malignancies include leukemias, lymphomas and myelomas, including acute myeloid leukemia, adult T-cell leukemia, T-cell large granula lymphocyte leukemia, acute lymphoblastic leukemia, chronic lymphocytic leukemia, chronic myelogenous leukemia, acute monocytic leukemia, Hodgkin's and Non-Hodgkin's lymphoma and multiple myeloma. Examples of solid tumors include, without limitation, ovarian cancer, endometrial cancer, breast cancer, lung cancer (small cell or non-small cell), colon cancer, prostate cancer, cervical cancer, pancreatic cancer, gastric cancer, esophageal cancer, hepatocellular carcinoma (liver cancer), renal cell carcinoma (kidney cancer), head-and-neck tumors, mesothelioma, melanoma, sarcomas, and brain tumors (e.g., gliomas, such as glioblastomas).

The methods of the invention may be practiced in an adjuvant setting. "Adjuvant setting" refers to a clinical setting in which a subject has a history of a proliferative disease, particularly cancer, and generally (but not necessarily) has been responsive to therapy, which includes, but is not limited to, surgery, radiotherapy, and/or chemotherapy. However, because of a history of the proliferative disease, these subjects are considered at risk of developing that disease. Treatment or administration in the "adjuvant setting" refers to a subsequent mode of treatment. In some embodiments, provided herein is a method for treating or effecting prophylaxis of cancer comprising administering to a subject having or at risk of cancer a therapeutically effective amount of any of the antibodies disclosed herein in an adjuvant setting.

The methods provided herein may also be practiced in a "neoadjuvant setting," that is, the method may be carried out before the primary/definitive therapy. In some aspects, the subject has previously been treated. In other aspects, the subject has not previously been treated. In some aspects, the treatment is a first line therapy. In some embodiments, provided herein is a method for treating or effecting prophylaxis of cancer comprising administering to a subject having or at risk of cancer a therapeutically effective amount of any of the antibodies disclosed herein in a neoadjuvant setting.

Other disorders treatable by antibodies of the invention include infectious diseases, of viruses, bacteria, fungi, protozoans, and other pathogens (e.g., hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus, HIV, SIV, and arboviral encephalitis virus, chlamydia, rickettsial bacteria, mycobacteria, staphylococci, treptocci, pneumonococci, meningococci and conococci, klebsiella, proteus, serratia, pseudomonas, legionella, diphtheria, salmonella, bacilli, cholera, tetanus, botulism, anthrax, plague, leptospirosis, and Lymes disease bacteria.

A. Administration of Antibodies

The antibodies described herein are administered in an effective regime meaning a dosage, route of administration and frequency of administration that delays the onset, reduces the severity, inhibits further deterioration, and/or ameliorates at least one sign or symptom of a disorder. If a subject is already suffering from a disorder, the regime can be referred to as a therapeutically effective regime. If the subject is at elevated risk of the disorder relative to the general population but is not yet experiencing symptoms, the regime can be referred to as a prophylactically effective regime. In some instances, therapeutic or prophylactic efficacy can be observed in an individual subject relative to historical controls or past experience in the same subject. In other instances, therapeutic or prophylactic efficacy can be demonstrated in a preclinical or clinical trial in a population of treated subjects relative to a control population of untreated subjects.

In some aspects, any of the methods described herein include the administration of a therapeutically effective amount of one or more of the antibodies described herein to subjects in need thereof. As used herein, a "therapeutically effective amount" or "therapeutically effective dosage" of an anticancer therapy (such as any of the anti-TIGIT antibodies described herein) is an amount sufficient to effect beneficial or desired results. For therapeutic use, beneficial or desired results include clinical results such as decreasing one or more symptoms resulting from cancer, increasing the quality of life of subjects suffering from cancer, decreasing the dose of other medications required to treat the cancer, enhancing the effect of another medication such as via targeting, delaying the progression of the disease, and/or prolonging survival. An effective dosage can be administered in one or more administrations. For purposes of this invention, an effective dosage of an anti-cancer therapy is an amount sufficient to accomplish therapeutic or prophylactic treatment either directly or indirectly. As is understood in the clinical context, a therapeutically effective dosage of an anti-cancer therapy may or may not be achieved in conjunction with another anti-cancer therapy.

Exemplary dosages for any of the antibodies described herein are about 0.1-20 mg/kg or 0.5-5 mg/kg body weight (e.g., about 0.5 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, or 20 mg/kg) or 10-1500 mg (such as any of less than 10 mg, 20 mg, 30 mg, 40 mg, 50 mg, 60 mg, 70 mg, 80 mg, 90 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1100 mg, 1200 mg, 1300 mg, 1400 mg, or 1500 mg or greater, inclusive of values in between these numbers), as a fixed dosage. The dosage depends on the condition of the subject and response to prior treatment, if any, whether the treatment is prophylactic or therapeutic and whether the disorder is acute or chronic, among other factors.

Administration can be parenteral, intravenous, oral, subcutaneous, intra-arterial, intracranial, intrathecal, intraperitoneal, intratumoral, topical, intranasal or intramuscular. Administration into the systemic circulation by intravenous or subcutaneous administration is preferred. Intravenous administration can be, for example, by infusion over a period such as 30-90 min.

The frequency of administration depends on the half-life of the antibody in the circulation, the condition of the subject and the route of administration among other factors. The frequency can be daily, weekly, monthly, quarterly, or at irregular intervals in response to changes in the subject's condition or progression of the disorder being treated. An exemplary frequency for intravenous administration is between weekly and quarterly over a continuous cause of treatment, although more or less frequent dosing is also possible. For subcutaneous administration, an exemplary dosing frequency is daily to monthly, although more or less frequent dosing is also possible.

The number of dosages administered depends on whether the disorder is acute or chronic and the response of the disorder to the treatment. For acute disorders or acute exacerbations of chronic disorders between 1 and 10 doses are often sufficient. Sometimes a single bolus dose, optionally in divided form, is sufficient for an acute disorder or acute exacerbation of a chronic disorder. Treatment can be repeated for recurrence of an acute disorder or acute exacerbation. For chronic disorders, an antibody can be administered at regular intervals, e.g., weekly, fortnightly, monthly, quarterly, every six months for at least 1, 5 or 10 years, or the life of the subject.

Treatment including an anti-TIGIT antibody may alleviate a disease by increasing the median progression-free survival or overall survival time of subjects with cancer by at least about 30%, 31%, 32%, 33%, 34%, 35%, 36%, 37%, 38%, 39%, 40%, 41%, 42%, 43%, 44%, 45%, 46%, 47%, 48%, 49%, but preferably by at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 100%, compared to control subjects, or increase either of these times by 2 weeks, 1, 2 or 3 months, or preferably by 4 or 6 months or even 9 months or a year. In addition or alternatively, treatment including the anti-TIGIT antibody can increase the complete response rate, partial response rate, or objective response rate (complete+partial) of subjects by at least about 30%, 31%, 32%, 33%, 34%, 35%, 36%, 37%, 38%, 39%, 40%, 41%, 42%, 43%, 44%, 45%, 46%, 47%, 48%, 49%, but preferably by at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 100% compared to the control subjects. Control subjects receive the same treatment as subjects receiving the anti-TIGIT antibody except for the anti-TIGIT antibody. Thus, control subjects may receive placebo alone or a combination of placebo and some chemotherapeutic agent other than the anti-TIGIT antibody if such is also received by the subjects receiving the anti-TIGIT antibody.

The anti-TIGIT antibodies disclosed herein can enhance NK cell-mediated cytotoxicity of CD155-expressing cells (such as, but not limited to, K562 cells), by any of about 10%, 11%, 12%, 13%, 14%, 15%, 16%, 17%, 18%, 19%, 20%, 21%, 22%, 23%, 24%, 25% 26% 27%, 28%, 29%, 30%, 31%, 32%, 33%, 34%, 35% or more relative to the amount of NK cell-mediated cytotoxicity of CD155-expressing cells in the absence of one of the anti-TIGIT antibodies disclosed herein.

Typically, in a clinical trial (e.g., a phase II, phase II/III or phase III trial), increases in median progression-free survival and/or response rate of the subjects treated with the anti-TIGIT antibody, relative to the control group of subjects are statistically significant, for example at the p=0.05 or 0.01 or even 0.001 level. The complete and partial response rates are determined by objective criteria commonly used in clinical trials for cancer, e.g., as listed or accepted by the National Cancer Institute and/or Food and Drug Administration and may include for example, tumor volume, number of tumors, metastasis, survival time, and quality of life measures, among others.

Pharmaceutical compositions for parenteral administration are preferably sterile and substantially isotonic and manufactured under GMP conditions. Pharmaceutical compositions can be provided in unit dosage form (i.e., the dosage for a single administration). Pharmaceutical compositions can be formulated using one or more physiologically acceptable carriers, diluents, excipients or auxiliaries. The formulation depends on the route of administration chosen. For injection, antibodies can be formulated in aqueous solutions, preferably in physiologically compatible buffers such as Hank's solution, Ringer's solution, or physiological saline or acetate buffer (to reduce discomfort at the site of injection). The solution can contain formulatory agents such as suspending, stabilizing and/or dispersing agents. Alternatively antibodies can be in lyophilized form for constitution with a suitable vehicle, e.g., sterile pyrogen-free water, before use. The concentration of antibody in liquid formulations can vary from e.g., about 10-150 mg/ml. In some formulations the concentration is about 25-50 mg/ml.

B. Combination Therapies

The present invention contemplates the use of anti-TIGIT antibodies in combination with one or more active therapeutic agents (e.g., chemotherapeutic agents) or other prophylactic or therapeutic modalities (e.g., radiation). In such combination therapy, the various active agents frequently have different, complementary mechanisms of action. Such combination therapy may be especially advantageous by allowing a dose reduction of one or more of the agents, thereby reducing or eliminating the adverse effects associated with one or more of the agents. Furthermore, such combination therapy may have a synergistic therapeutic or prophylactic effect on the underlying disease, disorder, or condition.

As used herein, "combination" is meant to include therapies that can be administered separately, for example, formulated separately for separate administration (e.g., as may be provided in a kit), and therapies that can be administered together in a single formulation (i.e., a "co-formulation").

In certain embodiments, any of the anti-TIGIT antibodies disclosed herein are administered or applied sequentially, e.g., where one agent is administered prior to one or more other agents. In other embodiments, the antibodies are administered simultaneously, e.g., where two or more agents are administered at or about the same time; the two or more agents may be present in two or more separate formulations or combined into a single formulation (i.e., a co-formulation). Regardless of whether the two or more agents are administered sequentially or simultaneously, they are considered to be administered in combination for purposes of the present invention.

The antibodies of the present invention may be used in combination with at least one other (active) agent in any manner appropriate under the circumstances. In one embodiment, treatment with the at least one active agent and at least one anti-TIGIT antibody of the present invention is maintained over a period of time. In another embodiment, treatment with the at least one active agent is reduced or discontinued (e.g., when the subject is stable), while treatment with an anti-TIGIT antibody of the present invention is maintained at a constant dosing regimen. In a further embodiment, treatment with the at least one active agent is reduced or discontinued (e.g., when the subject is stable), while treatment with an anti-TIGIT antibody of the present invention is reduced (e.g., lower dose, less frequent dosing or shorter treatment regimen). In yet another embodiment, treatment with the at least one active agent is reduced or discontinued (e.g., when the subject is stable), and treatment with the anti-TIGIT antibody of the present invention is increased (e.g., higher dose, more frequent dosing or longer treatment regimen). In yet another embodiment, treatment with the at least one active agent is maintained and treatment with the anti-TIGIT antibody of the present invention is reduced or discontinued (e.g., lower dose, less frequent dosing or shorter treatment regimen). In yet another embodiment, treatment with the at least one active agent and treatment with the anti-TIGIT antibodies of the present invention are reduced or discontinued (e.g., lower dose, less frequent dosing or shorter treatment regimen).

Treatment with antibodies of the invention can be combined with other treatments effective against the disorder being treated. When used in treating a proliferative condition, cancer, tumor, or precancerous disease, disorder or condition, the antibodies of the invention can be combined with chemotherapy, radiation (e.g., localized radiation therapy or total body radiation therapy), stem cell treatment, surgery or treatment with other biologics.

In certain embodiments, the present invention provides methods for tumor suppression of tumor growth comprising administration of the anti-TIGIT antibodies disclosed herein in combination with a signal transduction inhibitor (STI) to achieve additive or synergistic suppression of tumor growth. As used herein, the term "signal transduction inhibitor" refers to an agent that selectively inhibits one or more steps in a signaling pathway. Signal transduction inhibitors (STIs) of the present invention include: (i) BCR-Abl kinase inhibitors (e.g., imatinib mesylate (GLEEVEC)); (ii) epidermal growth factor (EGF) receptor inhibitors, including kinase inhibitors and antibodies; (iii) HER-2/neu receptor inhibitors (e.g., HERCEPTIN® (trastuzumab)); (iv) inhibitors of Akt family kinases or the Akt pathway (e.g., rapamycin); (v) cell cycle kinase inhibitors (e.g., flavopiridol); and (vi) phosphatidyl inositol kinase inhibitors. Agents involved in in immunomodulation can also be used in combination with the anti-TIGIT antibodies disclosed herein for the suppression of tumor growth in cancer patients.

Examples of chemotherapeutic agents include, but are not limited to, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chiorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); cyclophosphamide; thiotepa; toxoids (i.e. taxanes), e.g., paclitaxel, taxol, and doxetaxel; chlorambucil; gemcitabine; 6-thioguanine; mercaptopurine; methotrexate; platinum and platinum coordination complexes such as cisplatin and carboplatin; vinblastine; etoposide (VP-16); ifosfamide; mitomycin C; mitoxantrone; vincristine; vinorelbine; navelbine; novantrone; teniposide; daunomycin; aminopterin; XELODA® (capecitabine); ibandronate; CPT11; topoisomerase inhibitors; camptothecins, difluoromethylornithine (DMFO); retinoic acid; esperamicins; capecitabine;), antimetabolites (e.g., azathioprine); anthracyclines; plant alkaloids (including, e.g. vinca alkaloids); and pharmaceutically acceptable salts, acids or derivatives of any of the above.

Chemotherapeutic agents also include anti-hormonal agents that act to regulate or inhibit hormonal action on tumors such as anti-estrogens, including for example tamoxifen, raloxifene, aromatase inhibiting 4(5)-imidazoles, 4-hydroxytamoxifen, trioxifene, keoxifene, onapristone, and toremifene; and antiandrogens such as flutamide, nilutamide, bicalutamide, leuprolide, and goserelin; and pharmaceutically acceptable salts, acids or derivatives of any of the above. In certain embodiments, combination therapy comprises administration of a hormone or related hormonal agent.

Additional treatment modalities that may be used in combination with the anti-TIGIT antibodies disclosed herein include radiotherapy, a monoclonal antibody against a tumor antigen, a complex of a monoclonal antibody and toxin, a T-cell adjuvant, bone marrow transplant, or antigen presenting cells (e.g., dendritic cell therapy) or cell-cell based therapies. The term "cell based therapy" as used herein refers to any therapy which involves the introduction of cells for purposes of achieving a desired therapeutic effect, such as, to repair damaged or repleted adult cell populations or tissues or to enhance an immune response against a pathogen or a proliferative cell (such as a cancer cell). In other embodiments, cell based therapy includes the introduction of a non-differentiated cell (such as a stem cell or other multi- or totipotent cell) capable of differentiating into a specific cell type required to achieve a desired therapeutic effect, such as, to repair damaged or repleted adult cell populations or tissues or to enhance an immune response against a pathogen or a proliferative cell (such as a cancer cell). In some embodiments, the antibodies of the invention can also be administered with tumor infiltrating T-cells or with natural killer cells, which have optionally been expanded or selected for honing to the tumor ex vivo. The antibody of the invention contributes to activation of these cells.

A preferred combination is an antibody of the invention with a second antibody directed at a surface antigen preferentially expressed on the cancer cells relative to control normal tissue. Some examples of antibodies that can be administered in combination therapy with antibodies of the invention for treatment of cancer include HERCEPTIN® (trastuzumab) against the HER2 antigen, AVASTIN® (bevacizumab) against VEGF, or antibodies to the EGF receptor, such as (ERBITUX®, cetuximab), and VECTIBIX® (panitumumab). Other agents that can be administered include antibodies or other inhibitors of any of PD-1, PD-L1, CTLA-4, 4-1BB, BTLA, VISTA, TIM-3 and LAG-3; or other downstream signaling inhibitors, e.g., mTOR and GSK3β inhibitors; and cytokines, e.g., interferon-γ, IL-2, and IL-15. Some specific examples of additional agents include: ipilimumab, pazopanib, sunitinib, dasatinib, pembrolizumab, INCR024360, dabrafenib, trametinib, atezolizumab (MPDL3280A), TARCEVA® (erlotinib), cobimetinib, and nivolumab. The choice of a second antibody or other agent for combination therapy depends on the cancer being treated. Optionally, the cancer is tested for expression or preferential expression of an antigen to guide selection of an appropriate antibody. The isotype of the second antibody is preferably human IgG1 to promote effector functions, such as ADCC, CDC and phagocytosis.

Antibodies of the invention can also be administered with vaccines eliciting an immune response against a cancer. Such immune response is enhanced by the antibody of the invention. The vaccine can include an antigen expressed on the surface of the cancer of a fragment thereof effective to induce an immune response, optionally linked to a carrier molecule.

The present invention contemplates use of the anti-TIGIT antibodies described herein in combination with immune checkpoint inhibitors.

The tremendous number of genetic and epigenetic alterations that are characteristic of all cancers provides a diverse set of antigens that the immune system can use to distinguish tumor cells from their normal counterparts. In the case of T cells, the ultimate amplitude (e.g., levels of cytokine production or proliferation) and quality (e.g., the type of immune response generated, such as the pattern of cytokine production) of the response, which is initiated through antigen recognition by the T-cell receptor (TCR), is regulated by a balance between co-stimulatory and inhibitory signals (immune checkpoints). Under normal physiological conditions, immune checkpoints are crucial for the prevention of autoimmunity (i.e., the maintenance of self-tolerance) and also for the protection of tissues from damage when the immune system is responding to pathogenic infection. The expression of immune checkpoint proteins can be dysregulated by tumors as an important immune resistance mechanism.

Examples of immune checkpoints (ligands and receptors), some of which are selectively upregulated in various types of tumor cells, that are candidates for blockade include PD-1 (programmed cell death protein 1); PD-L1 (programmed death ligand-1); BTLA (B and T lymphocyte attenuator); CTLA-4 (cytotoxic T-lymphocyte associated antigen 4); TIM-3 (T-cell membrane protein 3); LAG-3 (lymphocyte activation gene 3); V-domain immunoglobulin suppressor of T cell activation (VISTA); CD96; A2aR (adenosine A2a receptor); A2bR (adenosine A2b receptor); CD73 (ecto-5'-nucleotidase); CD39 (ENTPD1, NTPDase1); Arginase; indoleamine-pyrrole 2,3-dioxygenase (IDO); tryptophan 2,3-dioxygenase (TDO); and Killer Inhibitory Receptors, which can be divided into two classes based on their structural features: i) killer cell immunoglobulin-like receptors (KIRs), and ii) C-type lectin receptors (members of the type II transmembrane receptor family) Other less well-defined immune checkpoints have been described in the literature, including both receptors (e.g., the 2B4 (also known as CD244) receptor) and ligands (e.g., certain B7 family inhibitory ligands such B7-H3 (also known as CD276) and B7-H4 (also known as B7-S1, B7x and VCTN1)). See Pardoll, (April 2012) Nature Rev. Cancer 12:252-64.

The present invention contemplates the use any of the anti-TIGIT antibodies disclosed herein in combination with inhibitors of the aforementioned immune-checkpoint receptors and ligands, as well as yet-to-be-described immune-checkpoint receptors and ligands. Certain modulators of immune checkpoints are currently available, whereas others are in late-stage development. To illustrate, when it was approved for the treatment of melanoma in 2011, the fully humanized CTLA-4 monoclonal antibody ipilimumab (YERVOY; Bristol-Myers Squibb) became the first immune checkpoint inhibitor to receive regulatory approval in the US. Fusion proteins comprising CTLA-4 and an antibody (CTLA-4-Ig; abatacept (ORENCIA; Bristol-Myers Squibb)) have been used for the treatment of rheumatoid arthritis, and other fusion proteins have been shown to be effective in renal transplantation patients that are sensitized to Epstein Barr Virus. Anti-PD-1 antibodies are under development (e.g., nivolumab (Bristol-Myers Squibb) and pembrolizumab (lambrolizumab) (Merck)), and anti-PD-L1 antibodies are also being evaluated (e.g., MPDL3280A (Roche)). Nivolumab and pembrolizumab have shown promise in patients with melanoma, lung and kidney cancer.

Similar combination therapies can be used in treating or preventing infectious disease, such as viral, bacterial, fungal and parasitic diseases, disorders and conditions, as well as disorders associated therewith. For example, an antibody of the invention can be combined with an antibody directed against the pathogen or a vaccine against the pathogen, such as palivizumab against rous sarcoma virus. The vaccine can be a protein of the pathogen or fragment thereof effective to induce an immune response. The antibody of the invention enhances the immune response of the antibody or vaccine directed against the pathogen. An antibody of the invention can also be administered with T-cells or natural killer cells expanded ex vivo.

Such combination therapy includes anti-viral agents targeting various viral life-cycle stages and having different mechanisms of action, including, but not limiting to, the following: inhibitors of viral uncoating (e.g., amantadine and rimantidine); reverse transcriptase inhibitors (e.g., acyclovir, zidovudine, and lamivudine); agents that target integrase; agents that block attachment of transcription factors to viral DNA; agents (e.g., antisense molecules) that impact translation (e.g., fomivirsen); agents that modulate translation/ribozyme function; protease inhibitors; viral assembly modulators (e.g., rifampicin); antiretrovirals such as, for example, nucleoside analogue reverse transcriptase inhibitors (e.g., azidothymidine (AZT), ddI, ddC, 3TC, d4T); non-nucleoside reverse transcriptase inhibitors (e.g., efavirenz, nevirapine); nucleotide analogue reverse transcriptase inhibitors; and agents that prevent release of viral particles (e.g., zanamivir and oseltamivir). Treatment and/or prevention of certain viral infections (e.g., HIV) frequently entail a group ("cocktail") of antiviral agents.

Other antiviral agents contemplated for use in combination with any of the anti-TIGIT antibodies disclosed herein include, but are not limited to, the following: abacavir, adefovir, amantadine, amprenavir, ampligen, arbidol, atazanavir, atripla, boceprevirertet, cidofovir, combivir, darunavir, delavirdine, didanosine, docosanol, edoxudine, emtricitabine, enfuvirtide, entecavir, famciclovir, fosamprenavir, foscarnet, fosfonet, ganciclovir, ibacitabine, imunovir, idoxuridine, imiquimod, indinavir, inosine, various interferons (e.g., peginterferon alfa-2a), lopinavir, loviride, maraviroc, moroxydine, methisazone, nelfinavir, nexavir, penciclovir, peramivir, pleconaril, podophyllotoxin, raltegravir, ribavirin, ritonavir, pyramidine, saquinavir, stavudine, telaprevir, tenofovir, tipranavir, trifluridine, trizivir, tromantadine, truvada, valaciclovir, valganciclovir, vicriviroc, vidarabine, viramidine, and zalcitabine.

The present invention contemplates the use of any of the anti-TIGIT antibodies disclosed herein in combination with antiparasitic agents. Such agents include, but are not limited to, thiabendazole, pyrantel pamoate, mebendazole, praziquantel, niclosamide, bithionol, oxamniquine, metrifonate, ivermectin, albendazole, eflornithine, melarsoprol, pentamidine, benznidazole, nifurtimox, and nitroimidazole. The skilled artisan is aware of other agents that may find utility for the treatment of parasitic disorders.

Embodiments of the present invention contemplate the use of any of the anti-TIGIT antibodies disclosed herein in combination with agents useful in the treatment or prevention of bacterial disorders. Antibacterial agents can be classified in various manners, including based on mechanism of action, based on chemical structure, and based on spectrum of activity. Examples of antibacterial agents include those that target the bacterial cell wall (e.g., cephalosporins and penicillins) or the cell membrane (e.g., polymyxins), or interfere with essential bacterial enzymes (e.g., sulfonamides, rifamycins, and quinolines). Most antibacterial agents that target protein synthesis (e.g., tetracyclines and macrolides) are bacteriostatic, whereas agents such as the aminoglycoside are bactericidal. Another means of categorizing antibacterial agents is based on their target specificity; "narrow-spectrum" agents target specific types of bacteria (e.g., Gram-positive bacteria such as *Streptococcus*), while "broad-spectrum" agents have activity against a broader range of bacteria. The skilled artisan is aware of types of anti-bacterial agents that are appropriate for use in specific bacterial infections.

Embodiments of the present invention contemplate the use of any of the anti-TIGIT antibodies disclosed herein in combination with agents useful in the treatment or prevention of fungal disorders. Antifungal agents include polyenes (e.g., amphotericin, nystatin, and pimaricin); azoles (e.g., fluconazole, itraconazole, and ketoconazole); allylamines (e.g., naftifine, and terbinafine) and morpholines (e.g., amorolfine); and antimetabolies (e.g., 5-fluorocytosine).

The present invention encompasses pharmaceutically acceptable salts, acids or derivatives of the agents (and members of the classes of agents) set forth above.

Antibodies against TIGIT can be combined with any of the second antibodies or agents described for use in co-therapies as components of a pharmaceutical composition. In a pharmaceutical composition, the agents can be combined with one or more pharmaceutically acceptable carriers as described.

V. Other Applications

The anti-TIGIT antibodies can be used for detecting TIGIT in the context of clinical diagnosis or treatment or in research. For example, the antibodies can be used to detect presence of TIGIT on T cells, natural killer cells and cancer cells as an indication a subject is suffering from a cancer or infectious disease amenable to treatment. Expression of TIGIT on T cells, natural killer cells and/or cancer cells of a subject suffering from cancer or infectious disease also provides an indication that the cancer or infectious disease is amenable to treatment with the antibodies of the present invention. The antibodies can also be sold as research reagents for laboratory research in detecting T cells, natural killer cells and cancer cells, and their response to various stimuli. In such uses, monoclonal antibodies can be labeled with fluorescent molecules, spin-labeled molecules, enzymes or radioisotopes, and can be provided in the form of kit with all the necessary reagents to perform the assay for TIGIT. The antibodies can also be used to purify TIGIT, e.g., by affinity chromatography.

VI. Kits

Antibodies against TIGIT can be combined with any of the second antibodies or agents described for use in co-therapies as components of a kit. The invention disclosed herein provides one or more kits containing one or more of the antibodies disclosed herein as well as one or more pharmaceutically acceptable excipients or carriers (such as, without limitation, phosphate buffered saline solutions, water, sterile water, polyethylene glycol, polyvinyl pyrrolidone, lecithin, arachis oil, sesame oil, emulsions such as oil/water emulsions or water/oil emulsions, microemulsions, nanocarriers and various types of wetting agents). Additives such as alcohols, oils, glycols, preservatives, flavoring agents, coloring agents, suspending agents, and the like may also be included in the kits of the present invention along with the carrier, diluent, or excipient. In one embodiment, a pharmaceutically acceptable carrier appropriate for use in the antibody compositions disclosed herein is sterile, pathogen free, and/or otherwise safe for administration to a subject without risk of associated infection and other undue adverse side effects. In a kit, the respective agents can be provided in separate vials with instructions for combination followed by administration or instructions for separate administration. The kit can also include written instructions for proper handling and storage of any of the anti-TIGIT antibodies disclosed herein.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise.

Although the present invention has been described in some detail by way of illustration and example for purposes of clarity and understanding, it will be apparent that certain changes and modifications may be practiced within the scope of the appended claims.

EXAMPLES

The following examples discuss the production, characterization, and humanization of monoclonal antibodies against human TIGIT and also provide exemplary methods by which binding characteristics by which the antibodies described in this application can be determined.

Example 1: Expression of Recombinant Human TIGIT Proteins

Gene cloning, mutagenesis and plasmid construction in this work was carried out with standard molecular biology techniques such as those described in Sambrook and Russel (*Molecular Cloning, A Laboratory Manual*, 3rd ed., 2001, Cold Spring Harbor Laboratory Press, Cold Spring Harbor, N.Y.), Kostelny et al. (*Int. J. Cancer* 93:556-565, 2001) and Cole et al. (*J. Immunol.* 159:3613-3621, 1997).

The mammalian expression vector pFCm404 (FIG. 1) for production of the extracellular region of human TIGIT fused to the Fc region of human immunoglobulin γ1 chain (hTIGIT-Fc; SEQ ID NO:59) contains the following genetic components. Proceeding clockwise from the SalI site of pFCm404 in FIG. 1, the plasmid contains the transcription unit for hTIGIT-Fc starting with the human cytomegalovirus (CMV) major immediate early promoter and enhancer (CMV-P in FIG. 1). The CMV promoter is followed by the coding regions of a signal peptide (sp; SEQ ID NO:2), the extracellular region of human TIGIT (hTIGIT; SEQ ID NO:3), a polypeptide linker (SEQ ID NO:4) and the human γ1 Fc region (SEQ ID NO:5), and then by the polyadenylation site of the human γ1 heavy chain gene. The hTIGIT-Fc gene is followed by the SV40 early promoter (SV40-P), the puromycin N-acetyl-transferase gene (puro) for resistance to puromycin, and a segment containing the SV40 polyadenylation site (SV40-A). Finally, pFCm404 contains a part of the plasmid pUC19, comprising the bacterial origin of replication (pUC ori) and the β lactamase gene (β lactamase). Arrows in the figure indicate the orientation of transcription. Relevant restriction enzyme sites are indicated in the figures.

The coding region of the extracellular region of human TIGIT in pFCm404 was replaced with a DNA fragment encoding the extracellular region of human CD155 (hCD155; SEQ ID NO:6), resulting in generation of a new expression vector pFCm406 (FIG. 1). The extracellular region of human CD155 fused to the human γ1 Fc region (hCD155-Fc; SEQ ID NO:7) is expressed from pFCm406.

The coding region of the γ1 Fc region between the AgeI and EagI sites in pFCm404 was replaced with a DNA fragment encoding the FLAG® peptide (FLAG®; SEQ ID NO:8) followed by the glycosylphosphatidylinositol linkage signal of human CD55 (GPI; SEQ ID NO:9), resulting in the generation of a new expression vector pFCm407 (FIG. 1). The extracellular region of human TIGIT fused to FLAG® and GPI (hTIGIT-GPI) encoded pFCm406 is expressed on the cell surface.

To obtain cell lines stably producing hTIGIT-Fc and hCD155-Fc in culture supernatants, the expression vectors pFCm404 and pFCm406, respectively, were introduced into the chromosome of a mouse myeloma cell line NS0 (European Collection of Animal Cell Cultures, Salisbury, Wiltshire, UK). NS0 cells were grown in DME medium containing 10% fetal bovine serum (FBS) at 37° C. in a 7.5% CO2 incubator. Stable transfection into NS0 was carried out by electroporation as described in Bebbington et al. (*Bio/Technology* 10: 169-175, 1992). Before transfection, the expression vectors were linearized using FspI. Approximately $10^7$ cells were transfected with 10 μg of linearized plasmid, suspended in DME medium containing 10% FBS, and plated into several 96-well plates. After 24 hrs, selection media (DME medium containing 10% FBS and 3 μg/ml puromycin) was applied. Approximately 10 days after the initiation of selection, culture supernatants were assayed for production of Fc fusion proteins by ELISA using goat anti-human gamma chain antibody for coating and HRP-conjugated goat anti-human gamma chain for detection of Fc fusion proteins.

NS0 stable transfectants producing of a high level of Fc fusion proteins were adapted to and expanded in Hybridoma-SFM media (Thermo Fisher Scientific, Waltham, Mass.), and grown to exhaustion in roller bottles. After centrifugation and filtration, culture supernatant was loaded onto a protein A SEPHAROSE® column (GE Healthcare, Piscataway, N.J.). The column was washed with phosphate-buffered saline (PBS) before Fc fusion proteins were eluted with 0.1 M glycine-HCl (pH 3.0). After neutralization with 1 M Tris-HCl (pH 8), the buffer of eluted Fc fusion proteins was changed to PBS by dialysis.

To obtain cell lines expressing hTIGIT-GPI on the surface, the expression vector pFCm407 was stably transfected into NS0 cells. Expression of hTIGIT-GPI on the cell surface was monitored by flow cytometry using rat anti-FLAG® monoclonal antibody and PE-labeled goat anti-rat IgG, Fc-specific antibody. NS0 cell lines expressing a high level of hTIGIT-GPI on the cell surface (NS0-hTIGIT) was used for screening of anti-TIGIT antibodies.

Example 2: Generation and Characterization of Anti-TIGIT Monoclonal Antibodies

Mouse hybridomas producing anti-human TIGIT monoclonal antibodies were generated at JN Biosciences (Mountain View, Calif.) following standard hybridoma techniques such as the GenomONE CF EX Cell Fusion Reagent (Cosmo Bio, Carlsbad, Calif.). As immunogens, human TIGIT-Fc fusion proteins and NS0-hTIGIT cells were used.

Mouse antibodies secreted in culture supernatants of hybridoma cells were subjected to a series of screening to identify the antibodies with the following properties: (1) binding to purified hTIGIT-Fc fusion protein, (2) binding to NS0-hTIGIT cells, (3) non-binding to NS0 cells, (4) binding to CD3+ T cells derived from phytohemagglutinin-treated human peripheral blood mononuclear cells and (5) blocking of the binding of hCD155-Fc fusion protein to NS0-hTIGIT cells. The first property to bind to hTIGIT-Fc was tested by ELISA using HRP-conjugated goat antibodies against mouse kappa and lambda light chains (SouthernBiotech, Birmingham, Ala.) for identification of mouse anti-TIGIT antibodies. The second, third and fourth properties were examined by flow cytometry using PE-labeled goat anti-mouse gamma chain antibody (SouthernBiotech) for detection of cell-bound mouse antibodies. The fifth property was analyzed by flow cytometry as described below. Three mouse monoclonal antibodies (TIG1, TIG2 and TIG3) were found to possess all of these five properties. TIG1, TIG2 and TIG3 monoclonal antibodies were purified from culture supernatant of hybridoma cells by protein A column chromatography as described above. The isotypes of TIG1, TIG2 and TIG3 are mouse IgG2b/kappa, IgG2a/kappa and IgG2a/kappa, respectively.

Figure 2:
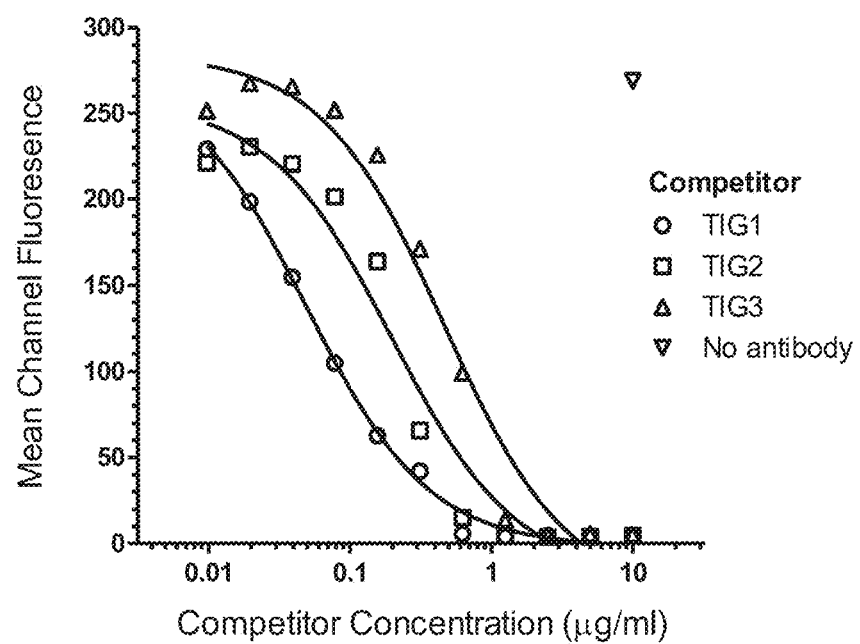
FIG. 2 depicts the inhibition of the TIGIT-CD155 interaction by anti-TIGIT antibodies.

The activity of TIG1, TIG2 and TIG3 to block the interaction between TIGIT and CD155 was analyzed by flow cytometry. NS0-hTIGIT cells were incubated with a sub-saturating concentration of hCD155-Fc in the presence (or absence) of various concentrations of an anti-TIGIT monoclonal antibody as a competitor. Detection of hCD155-Fc bound to NS0-hTIGIT cells was performed with DYLIGHT®488-labeled goat anti-human IgG, Fc-specific antibody (Jackson ImmunoResearch, West Grove, Pa.). As shown in FIG. 2, TIG1, TIG2 and TIG3 inhibited the binding of hCD155-Fc to NS0-hTIGIT cells in a dose-dependent manner. The half maximal inhibitory concentration ($IC_{50}$) for blocking of the interaction between hCD155-Fc and NS0-hTIGIT cells was 49 ng/ml for TIG1, 197 ng/ml for TIG2, and 460 ng/ml for TIG3. The antibody concentration needed to block more than 95% of the binding of CD155 to TIGIT was 0.63 µg/ml for TIG1, 1.25 µg/ml for TIG2, and 2.5 µg/ml of TIG3.

Example 3: V Gene Sequencing of Anti-TIGIT Monoclonal Antibodies

Determination of heavy and light chain variable region (VH and VL, respectively) sequences of mouse anti-TIGIT antibodies was carried out following the procedures described in Tsurushita et al (Methods 36:69-83, 2005). Total RNA was extracted from approximately $10^7$ cells using TRIzol reagent (Invitrogen, Carlsbad, Calif.) according to the supplier's protocol. Oligo dT-primed cDNA for 5'-RACE was synthesized using the SMARTer RACE cDNA Amplification Kit (Clontech, Mountain View, Calif.) following the supplier's protocol. The VH and VL cDNAs were amplified by polymerase chain reaction (PCR) with Phusion DNA polymerase (Thermo Fisher Scientific, Waltham, Mass.) using 3' primers that anneal specifically to the mouse heavy or light chain constant regions (Tsurushita et al., supra), respectively, and the 5' primer provided in the SMARTer RACE cDNA Amplification Kit Amplified VH and VL genes were cloned using the CloneJet PCR Cloning Kit (Thermo Fisher Scientific) and subjected to sequencing with primers provided in the CloneJet PCR Cloning Kit. Several VH and VL clones were sequenced and unique sequences homologous to typical mouse heavy and light chain variable regions were identified.

The amino acid sequence of the mature VH of TIG1 (SEQ ID NO: 10) is shown in FIG. 3. The CDR1, 2 and 3 amino acid sequences of TIG1 VH are NFGMH (SEQ ID NO:11), FISSGSSSIYYADTVKG (SEQ ID NO:12) and MRLDYYAMDY (SEQ ID NO:13), respectively.

The amino acid sequence of the mature VL of TIG1 (SEQ ID NO:14) is shown in FIG. 4. The CDR1, 2 and 3 amino acid sequences of TIG1 VL are RASKSISKYLA (SEQ ID NO:15), SGSTLQS (SEQ ID NO:16) and QQHNEYPWT (SEQ ID NO:17), respectively.

The amino acid sequence of the mature TIG2 VH (SEQ ID NO: 18) is shown in FIG. 5. The CDR1, 2 and 3 amino acid sequences of TIG2 VH are EYTMH (SEQ ID NO:19), GINPNNGGTSYNQKFKG (SEQ ID NO:20) and PGWYNYAMDY (SEQ ID NO:21), respectively.

The amino acid sequence of the mature TIG2 VL (SEQ ID NO:22) is shown in FIG. 6. The CDR1, 2 and 3 amino acid sequences of TIG2 VL are KASQGVSTAVA (SEQ ID NO:23), SASYRYT (SEQ ID NO:24) and QQHYITPWT (SEQ ID NO:25), respectively.

The amino acid sequence of the mature TIG3 VH (SEQ ID NO: 26) is shown in FIG. 7. The CDR1, 2 and 3 amino acid sequences of TIG3 VH are DYDMS (SEQ ID NO:27), YISDGGYNTYYPDTVKG (SEQ ID NO:28) and QILLRYYFDY (SEQ ID NO:29), respectively.

The amino acid sequence of the mature TIG3 VL (SEQ ID NO:30) is shown in FIG. 8. The CDR1, 2 and 3 amino acid sequences of TIG3 VL are KSSQSLLYSSNQKNYLA (SEQ ID NO:31), WASTRES (SEQ ID NO:32) and QQYHSYPWT (SEQ ID NO:33), respectively.

Assignment of CDR sequences and numbering of amino acid positions in FIGS. 3 to 8 are according to Kabat et al. (1991). CDR1, CDR2 and CDR3 sequences are underlined in the figures.

Example 4: Construction and Expression of Humanized TIG1 Antibody

Humanization of TIG1 VH and VL was carried out as described by Queen et al. (*Proc. Natl. Acad. Sci. USA.* 86:10029-10033, 1989) following the procedures of Tsurushita et al. (*Methods* 36:69-83, 2005). In brief, a three-dimensional molecular model of the variable regions of TIG1 was first constructed using JN Biosciences' proprietary algorithm. Next, the framework amino acid residues important for the formation of the structure of the complementarity determining regions (CDRs) of TIG1 were identified using the molecular model. In parallel, cDNA-derived human VH and VL amino acid sequences with high homology to TIG1 VH and VL, respectively, were selected. Finally, CDR sequences together with framework amino acid residues important for maintaining the CDR structure were grafted from TIG1 VH and VL into the corresponding selected human framework sequences.

The amino acid sequence of the designed humanized TIG1 VH (HuTIG1 VH) is MDSRLNLVFLVLILK-GVQCEVQLVESGGGLVQPGGSRLSCAASGFTFSNF-GMHWV RQAPGKGLEWVAFISSGSSSIYYADTVKGR-FTISRDNAKNSLYLQMNSLRAEDTAVY YCARMRLDYYAMDYWGQGTMVTVSS (SEQ ID NO: 34). The mature HuTIG1 VH amino acid sequence, EVQLVESGGGLVQPGGSLRLSCAASGFTFSNFGMH-WVRQAPGKGLEWVAFISSGSSS IYYADTVKGR-FTISRDNAKNSLYLQMNSLRAEDTAVYYCARM-RLDYYAMDYWGQ GTMVTVSS (SEQ ID NO:35), starts at position 20 in SEQ ID NO:34.

The amino acid sequence of the designed humanized TIG1 VL (HuTIG1 VL) is MRFQVQVLGLLLLWIS-GAQCDIQMTQSPSSLSASVGDRVTITCRASKSISKY-LAWYQ QKPGKAPKLLIYSGSTLQSGVPSRFSGSGS-GTDFTLTISSLQPEDFATYYCQQHNEYP WTFGGGTKVEIK (SEQ ID NO:36). The mature HuTIG1 VL amino acid sequence, DIQMTQSPSSLSAS-VGDRVTITCRASKSISKYLAWYQQKPGKAPKLLI-YSGSTLQSGV PSRFSGSGSGTDFTLTISSLQPEDFA-TYYCQQHNEYPWTFGGGTKVEIK (SEQ ID NO:37), starts at position 21 in SEQ ID NO:36.

A gene encoding HuTIG1 VH was synthesized as an exon including a splice donor signal at the 3' end of the coding region, a SpeI site at the 5' end of the fragment, and a HindIII site at the 3' end of the fragment. The nucleotide sequence of the synthetic HuTIG1 VH gene flanked by the SpeI and HindIII sites (SEQ ID NO:38) is shown alongside the deduced amino acid sequence (SEQ ID NO:34) in FIG. 9A.

A gene encoding HuTIG1 VL was synthesized as an exon including a splice donor signal at the 3' end of the coding region, a NheI site at the 5' end of the fragment, and an EcoRI site at the 3' end of the fragment. The nucleotide sequence of the synthetic HuTIG1 VL gene flanked by the NheI and EcoRI sites (SEQ ID NO:39) is shown alongside the deduced amino acid sequence (SEQ ID NO:36) in FIG. 9B.

Figure 10:
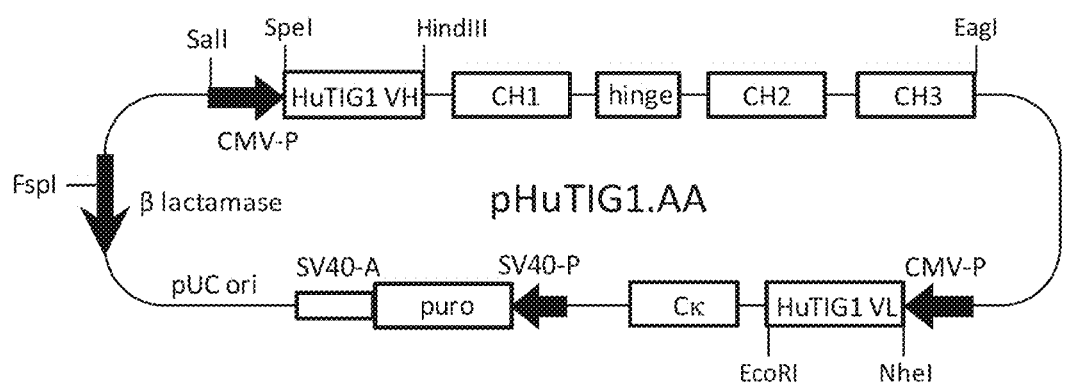
FIG. 10 shows the schematic structure of the expression vector pHuTIG1.AA.

The mammalian expression vector pHuTIG1.AA (FIG. 10) for production of the humanized IgG1/kappa form of the mouse anti-human TIGIT monoclonal antibody TIG1 (HuTIG1-IgG1.AA) was constructed to contain the following genetic components. Proceeding clockwise from the SalI site in FIG. 10, the vector contains the heavy chain transcription unit starting with the human cytomegalovirus (CMV) major immediate early promoter and enhancer (CMV-P in the figure) to initiate transcription of the antibody heavy chain gene. The CMV promoter is followed by an exon encoding the heavy chain variable region of the humanized form of TIG1 flanked by the SpeI and HindIII sites (HuTIG1 VH), a genomic sequence containing the human γ1 heavy chain constant regions including the CH1, hinge, CH2 and CH3 exons with the intervening introns, and the polyadenylation site of the human γ1 heavy chain gene. The CH2 region encoded in pHuTIG1.AA carries amino acid substitutions to alanine residues at positions 234 and 235 (Eu numbering) (L234A/L235A) for elimination of effector functions (Hezareh et al., *J. Virol.* 75:12161-12168, 2001). After the heavy chain gene sequence, the light chain transcription unit begins with the CMV promoter and enhancer (CMV-P), followed by an exon encoding the light chain variable region of the humanized form of TIG1 flanked by the NheI and EcoRI sites (HuTIG1 VL), a genomic sequence containing the human kappa chain constant region exon (CIO with part of the intron preceding it, and the polyadenylation site of the human kappa chain gene following the Cκ exon. The light chain gene is then followed by the SV40 early promoter (SV40-P), the puromycin N-acetyl-transferase gene (puro) for resistance to puromycin, and a segment containing the SV40 polyadenylation site (SV40-A). Finally, pHuTIG1.AA contains a part of the plasmid pUC19, comprising the bacterial origin of replication (pUC ori) and the β lactamase gene (β lactamase). Arrows in the figure indicate the orientation of transcription.

The amino acid sequence of the mature gamma heavy chain of HuTIG1-IgG1.AA encoded in pHuTIG1.AA is (SEQ ID NO: 40)
EVQLVESGGGLVQPGGSLRLSCAASGFTFSNFGMHWVRQAPGKGLEWVAF

ISSGSSSIYYADTVKGRFTISRDNAKNSLYLQMNSLRAEDTAVYYCARMR

LDYYAMDYWGQGTMVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPEAAGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPGK.

The C-terminal lysine may or may not be present.
The amino acid sequence of the mature kappa light chain of HuTIG1-IgG1.AA encoded in pHuTIG1.AA is (SEQ ID NO: 41)
DIQMTQSPSSLSASVGDRVTITCRASKSISKYLAWYQQKPGKAPKLLIYS

GSTLQSGVPSRFSGSGSGTDFTLTISSLQPEDFATYYCQQHNEYPWTFGG

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC.

The expression vector pHuTIG1.AA was introduced into the chromosomes of a Chinese hamster ovary cell line CHO-K1 (ATCC, Manassas, Va.) to obtain cell lines stably producing HuTIG1-IgG1.AA. CHO-K1 cells were grown in SFM4CHO media (GE Healthcare Life Sciences, Logan, Utah) at 37° C. in a 7.5% CO2 incubator. Stable transfection into CHO-K1 was carried out by electroporation. Before transfection, pHuTIG1.AA was linearized using FspI. In a typical experiment, approximately $10^7$ cells were transfected with 20 μg of linearized plasmid, suspended in SFM4CHO media, and plated at 100 μl/well in several 96-well plates after appropriate dilutions of cells. After 48 hr, SFM4CHO media containing 20 μg/ml of puromycin was added at 100 μl/well for isolation of stable transfectants. Approximately ten days after the initiation of selection, culture supernatants of transfectants were assayed for antibody production.

Expression of HuTIG1-IgG1.AA was measured by sandwich ELISA. In a typical experiment, an ELISA plate was coated with goat anti-human IgG Fc-specific polyclonal antibody, washed with Wash Buffer (PBS containing 0.05% TWEEN® 20 (polysorbate 20)), and blocked with ELISA Buffer (PBS containing 2% Skim Milk and 0.05% TWEEN® 20 (polysorbate 20)). After washing with Wash Buffer, test samples appropriately diluted in ELISA Buffer were applied to the ELISA plate. An appropriate humanized IgG1/κ antibody was used as a standard. After incubating the ELISA plate for 1 hr at room temperature and washing with Wash Buffer, bound antibodies were detected using HRP-conjugated goat anti-human kappa chain polyclonal antibody. After incubating the plate for 0.5 hr at room temperature and washing with Wash Buffer, color development was initiated by adding 100 μl/well of ABTS substrate (Sigma-Aldrich) and stopped with 100 μl/well of 2% oxalic acid. Absorbance was read at 405 nm.

CHO-K1 stable transfectants highly producing HuTIG1-IgG1.AA were expanded in SFM4CHO until the cell viability became less than 50%. After centrifugation and filtration, culture supernatants were loaded onto a Protein A column (HITRAP® MABSelect SuRe, GE Healthcare, Piscataway, N.J.). The column was washed with PBS before the antibody was eluted with 0.1 M glycine-HCl (pH 3.0). Buffer of eluted antibodies was neutralized with 1 M Tris-HCl (pH 8) and then changed to PBS by dialysis. Antibody concentration was determined by measuring absorbance at 280 nm (1 mg/ml=1.4 OD).

Example 5: Characterization of HuTIG1-IgG1.AA

Figure 11:
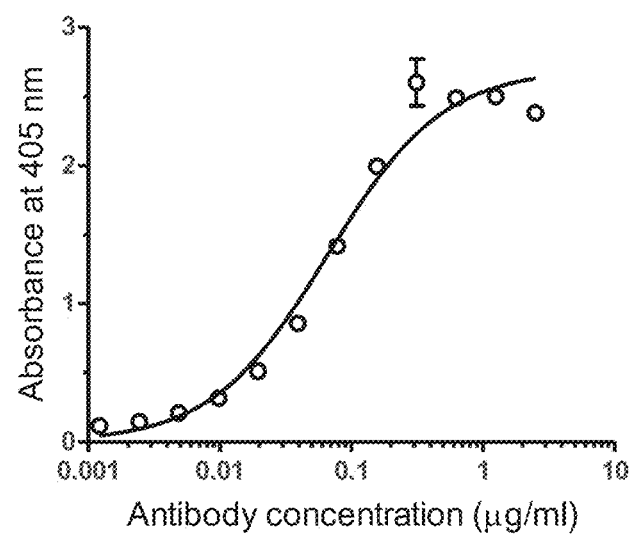
FIG. 11 shows the results of an ELISA analysis for binding of HuTIG1-IgG1.AA to human TIGIT.

Binding of HuTIG1-IgG1.AA to human TIGIT was examined by ELISA. An ELISA plate was coated with 5 μg/ml hTIGIT-Fc in PBS (100 μl/well) at 4° C. overnight, washed with Wash Buffer (PBS containing 0.05% TWEEN® 20 (polysorbate 20)), and blocked with 200 μl/well of Super-Block Blocking Buffer (Thermo Fisher Scientific). After washing wells with Wash Buffer, HuTIG1-IgG1.AA, starting at 2.5 μg/ml and serial 2-fold dilutions in SuperBlock Blocking Buffer, was added for binding to plate-bound human TIGIT. After incubating the ELISA plate for 1 hr at room temperature and washing with Wash Buffer, bound antibodies were detected with 100 μl/well of HRP-conjugated goat anti-human kappa chain polyclonal antibody (Southern Biotech), 1/2,000-diluted in ELISA Buffer. After incubating for 30 min at room temperature and washing with Wash Buffer, color development was initiated with 100 μl/well of ABTS substrate and stopped with 100 μl/well of 2% oxalic acid. Absorbance was read at 405 nm. As shown in FIG. 11, HuTIG1-IgG1.AA bound to human TIGIT in a dose-dependent manner. The half maximal effective concentration (EC$_{50}$) of HuTIG1-IgG1.AA for binding to TIGIT was 65 ng/ml. This shows that HuTIG1-IgG1.AA is a good binder to human TIGIT.

Figure 12:
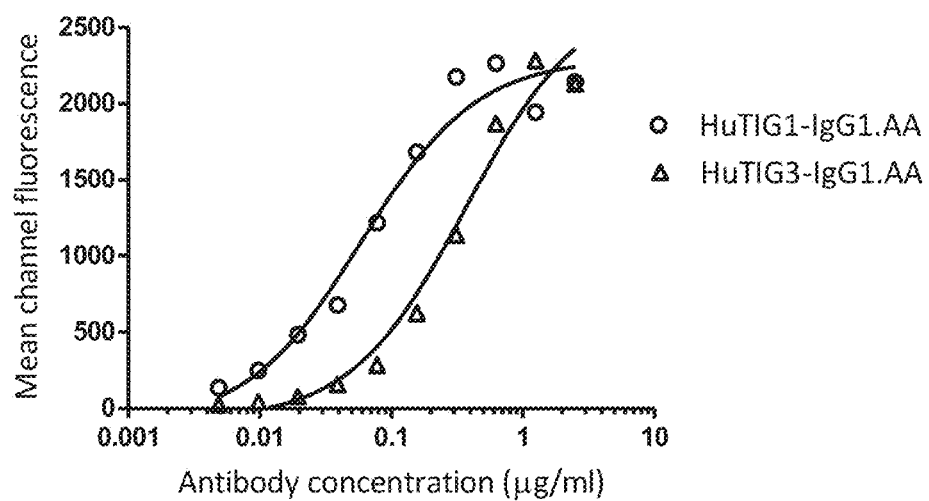
FIG. 12 depicts a FACS analysis for binding of HuTIG1-IgG1.AA and HuTIG3-IgG1.AA to human TIGIT.

Binding of HuTIG1-IgG1.AA to human TIGIT was also examined by flow cytometry. NS0-hTIGIT cells (8×10$^5$ cells) were incubated in 160 μl of FACS Buffer (PBS containing 0.5% bovine serum albumin and 0.05% sodium azide) in the presence (or absence) of various concentrations of HuTIG1-IgG1.AA, starting at 10 μg/ml and serial 2-fold dilutions, for 20 min at 4° C. After washing with FACS Buffer, HuTIG1-IgG1.AA binding on NS0-hTIGIT cells were detected with PE-labeled goat anti-human IgG antibody in FACS Buffer. After incubation for 20 min and washing with FACS Buffer, the cells were subjected to flow cytometry using a FACScan flow cytometer (BD Biosciences, San Jose, Calif.) to obtain the mean channel fluorescence (MCF) at each antibody concentration. FIG. 12 shows the plot of the MCF (vertical axis) at each antibody concentration (horizontal axis). The EC$_{50}$ value was 60 ng/ml. This shows that HuTIG1-IgG1.AA is a good binder to human TIGIT expressed on the cell surface.

Figure 13:
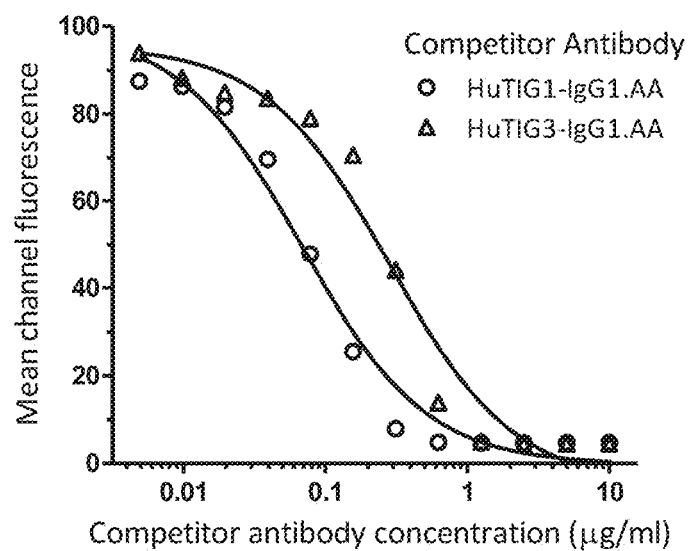
FIG. 13 is a graph showing the blocking of the interaction between human TIGIT and human CD155 by HuTIG1-IgG1.AA and HuTIG3-IgG1.AA.

The activity of HuTIG1-IgG1.AA to block the interaction between human TIGIT and human CD155 was analyzed by flow cytometry using NS0-hTIGIT cells. NS0-hTIGIT cells (10$^6$ cells) were incubated with sub-saturating concentration (125 ng/ml) of FITC-labeled hCD155-Fc fusion proteins (hCD155-Fc-FITC) in 200 μl of FACS Buffer in the presence (or absence) of various concentrations of HuTIG1-IgG1.AA, starting at 10 μg/ml and serial 2-fold dilutions, for 20 min at 4° C. After washing with FACS Buffer, NS0-hTIGIT cells were subjected to flow cytometry using a FACScan flow cytometer (BD Biosciences, San Jose, Calif.). To examine the binding of hCD155-Fc-FITC on the cells, MCF was obtained at each antibody concentration. As shown in FIG. 13, HuTIG1-IgG1.AA blocked the interaction between hCD155-Fc-FITC and TIGIT on the cell surface in a dose-dependent manner. The half maximal inhibitory concentration (IC$_{50}$) of HuTIG1-IgG1.AA to block the TIGIT-CD155 interaction was 67 ng/ml. This indicates that HuTIG1-IgG1.AA is an effective blocker of the interaction between CD155 and TIGIT.

Example 6: Construction and Expression of Humanized TIG3 Antibody

Humanization of TIG3 VH and VL was carried out following the general procedure described in Example 4. The amino acid sequence of the designed humanized TIG3 VH (HuTIG3 VH) is MNFGLRLIFLVLTLK-GVNCEVQLVESGGGLVQPGGSLRLSCAASGFAFSDY-DMSWV RQAPGKGLEWVAYISDGGYNTYYPDTVK-GRFTISRDNAKNSLYLQMNSLRAEDTAV YYCARQILLRYYFDYWGQGTTVTVSS (SEQ ID NO: 42). The mature HuTIG3 VH amino acid sequence, EVQLVESGGGLVQPGGSLRLSCAASGFAFSDYDM-SWVRQAPGKGLEWVAYISDGG YNTYYPDTVKGR-FTISRDNAKNSLYLQMNSLRAEDTAVYYCARQILL-RYYFDYWGQ GTTVTVSS (SEQ ID NO:43), starts at position 20 in SEQ ID NO:42.

The amino acid sequence of the designed humanized TIG3 VL (HuTIG3 VL) is MDSQAQVLMLLLLWVS-GTCGDIQMTQSPSSLSASVGDRVTITCKSSQSLLYSS-NQKN YLAWYQQKPGKAPKLLIYWASTRES GVPSRF-SGSGSGTDFTLTISSLQPEDFAVYYC QQYHSYPWTFGGGTKVEIK (SEQ ID NO:44). The mature HuTIG3 VL amino acid sequence, DIQMTQSPSSLSASVGDRVTITCKSSQSLLYSSNQK-NYLAWYQQKPGKAPKLLIYWA STRESGVPSRF-SGSGSGTDFTLTISSLQPEDFAVYYCQQYHSYPWTF-GGGTKVEIK (SEQ ID NO:45), starts at position 21 in SEQ ID NO:44.

A gene encoding HuTIG3 VH was synthesized as an exon including a splice donor signal at the 3' end of the coding region, a SpeI site at the 5' end of the fragment, and a HindIII site at the 3' end of the fragment. The nucleotide sequence of the synthetic HuTIG3 VH gene (SEQ ID NO:46) is shown alongside the deduced amino acid sequence (SEQ ID NO:42) in FIG. 14A.

A gene encoding humanized TIG3 VL (HuTIG3 VL) was synthesized as an exon including a splice donor signal at the 3' end of the coding region, a NheI site at the 5' end of the fragment, and an EcoRI site at the 3' end of the fragment. The nucleotide sequence of the synthetic HuTIG3 VL gene (SEQ ID NO:47) is shown alongside the deduced amino acid sequence (SEQ ID NO:44) in FIG. 14B.

The mammalian expression vector pHuTIG3.AA for production of the humanized IgG1/kappa form of the anti-human TIGIT monoclonal antibody TIG3 (HuTIG3-IgG1.AA) was constructed by modifying pHuTIG1.AA as follows: (1) the HuTIG1 VH gene was replaced with the HuTIG3 VH gene between the SpeI and HindIII sites, and (2) the HuTIG1 VL gene was replaced with the HuTIG3 VL gene between the NheI and EcoRI sites. The CH2 region encoded in pHuTIG3.AA carries amino acid substitutions to alanine residues at positions 234 and 235 (Eu numbering) (L234A/L235A) to eliminate effector functions.

The amino acid sequence of the mature gamma heavy chain of HuTIG3-IgG1.AA encoded in pHuTIG3.AA is (SEQ ID NO: 48)
EVQLVESGGGLVQPGGSLRLSCAASGFAFSDYDMSWVRQAPGKGLEWVAY

ISDGGYNTYYPDTVKGRFTISRDNAKNSLYLQMNSLRAEDTAVYYCARQI

LLRYYFDYWGQGTTVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPEAAGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPGK

The C-terminal lysine may or may not be present.
The amino acid sequence of the mature kappa light chain of HuTIG3-IgG1.AA encoded in pHuTIG3.AA is (SEQ ID NO: 49)
DIQMTQSPSSLSASVGDRVTITCKSSQSLLYSSNQKNYLAWYQQKPGKAP

KLLIYWASTRESGVPSRFSGSGSGTDFTLTISSLQPEDFAVYYCQQYHSY

PWTFGGGTKVEIKRTVAAPSVFIFPPSDEQLKSGTASVVCLLNNFYPREA

KVQWKVDNALQSGNSQESVTEQDSKDSTYSLSSTLTLSKADYEKHKVYAC

EVTHQGLSSPVTKSFNRGEC.

Transient transfection of pHuTIG3.AA into 100 ml of exponentially growing Expi293 cells (Thermo Fisher Scientific) was carried out according to the supplier's protocol. CHO-K1 stable transfectants highly producing HuTIG3-IgG1.AA were also generated by electroporation of pHuTIG3.AA as described above and expanded in SFM4CHO until the cell viability became less than 50%. HuTIG3-IgG1.AA was purified from culture supernatants of each of transiently transfected Expi293 cells and stably transfected CHO-K1 cells by a protein A affinity column as described above.

Example 7: Characterization of HuTIG3-IgG1.AA

Figure 15:
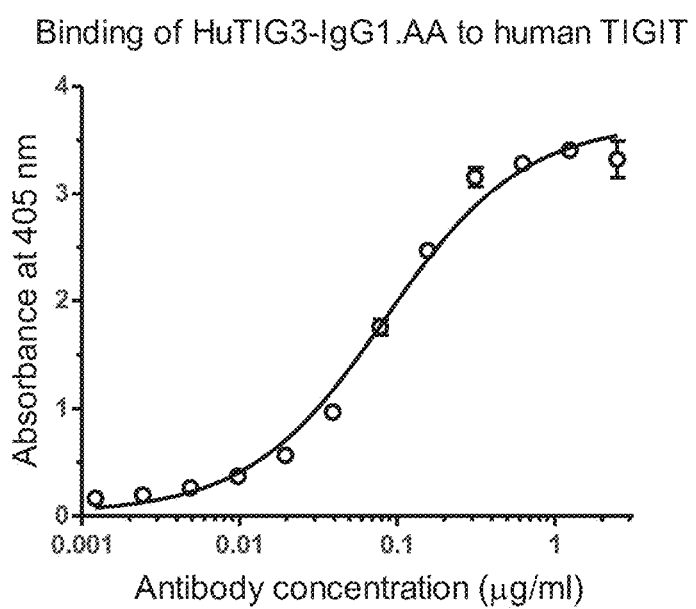
FIG. 15 depicts an ELISA analysis for binding of HuTIG3-IgG1.AA to human TIGIT.

Binding of HuTIG3-IgG1.AA to human TIGIT was examined by ELISA as described in Example 5. As shown in FIG. 15, HuTIG3-IgG1.AA bound to human TIGIT in a dose-dependent manner. The half maximal effective concentration ($EC_{50}$) of HuTIG3-IgG1.AA for binding to TIGIT was 85 ng/ml. This shows that HuTIG3-IgG1.AA is a good binder to human TIGIT.

Binding of HuTIG3-IgG1.AA to human TIGIT was also examined by flow cytometry as described in Example 5. As shown in FIG. 12, HuTIG3-IgG1.AA bound to human TIGIT in a dose-dependent manner. The half maximal effective concentration ($EC_{50}$) of HuTIG3-IgG1.AA for binding to TIGIT was 370 ng/ml. This shows that HuTIG3-IgG1.AA is a good binder to human TIGIT.

The activity of HuTIG3-IgG1.AA to block the interaction of TIGIT with CD155 was analyzed by flow cytometry using NS0-hTIGIT cells and FITC-labeled hCD155-Fc as described in Example 5. As shown in FIG. 13, HuTIG3-IgG1.AA blocked the interaction between TIGIT and CD155 in a dose-dependent manner. The half maximal inhibitory concentration ($IC_{50}$) of HuTIG3-IgG1.AA to block the TIGIT-CD155 interaction was 279 ng/ml. This indicates that HuTIG3-IgG1.AA is an effective blocker of the interaction between CD155 to TIGIT.

Example 8: IL-2 Cytokine Response to Tetanus Toxoid in Human T Cells is Enhanced by TIGIT Blockade The ability of murine anti-TIGIT antibodies to enhance antigen-specific T cell responses was examined using an in vitro antigen-specific recall assay to tetanus toxoid (see, e.g., Piersma et al., *Vaccine*. 2006 Apr. 12; 24(16):3076-83; Zaunders et al., *J Immunol*. 2009 Aug. 15; 183(4):2827-36). Sufficient vaccine protection to tetanus toxoid is achieved by booster injections which allow for the immune system to induce CD4+ and CD8+ T cell memory responses. As a surrogate measure of the effectiveness (see, e.g., Plotkin et al., *Clin Vaccine Immunol*. 2010 July; 17(7): 1055-1065; Goulon et al. November 1972 *Presse Med*. 1:3049-3050.), serum levels of 0.1 IU/mL of anti-Tetanus Toxoid are indicative of a maintained immune response.

Figure 16:
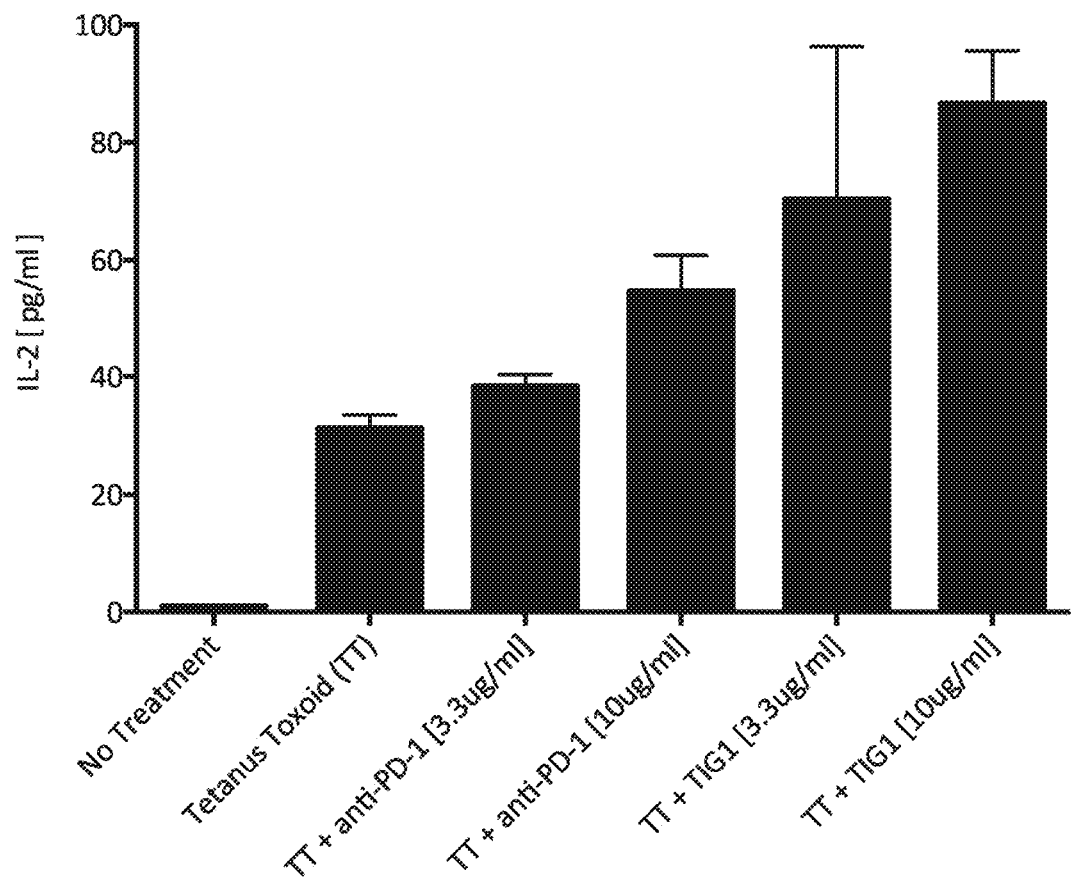
FIG. 16 shows increased IL-2 Production by TIG1 in an antigen-specific recall stimulation.

Peripheral blood mononuclear cells (PBMCs) from human volunteers vaccinated with tetanus toxoid were obtained (iQ Biosciences) with tetanus blood titer of the volunteers was confirmed to be higher than 1.0 IU/ml by ELISA (Genway). 800,000 PBMCs were cultured in RPMI 1640 medium (Invitrogen) containing 10% fetal bovine serum (FBS) in 96-well round bottom plates (Nunc). 2 µg/ml of tetanus toxoid (List Biological Laboratories) was added to the wells containing PBMCs in the presence of mouse anti-PD-1 antibody (Biolegend, clone EH12.2H7) or anti-TIGIT antibody (TIG1) at 3.3 µg/ml or 10 µg/ml for 4 days at 37° C. in a 5% CO2 incubator. As a control, 2 µg/ml of tetanus toxoid was added to PBMCs without any antibodies. Supernatants from the cultured wells were harvested and a cytokine indicative of T cell activation, IL-2, was measured by cytokine bead arrays (BD Pharmingen, CBA Th1/Th2 Cytokine Kit) by flow cytometry (BD FACSCalibur). As shown in FIG. 16, IL-2 production by tetanus toxoid stimulation alone was 31 pg/ml. IL-2 production was further enhanced to 70 pg/ml and 86 pg/ml in the presence of mouse anti-TIGIT antibody TIG1 at 3.3 µg/ml and 10 µg/ml respectively. IL-2 production by tetanus toxoid stimulation was also enhanced to 39 pg/ml and 57 pg/ml in the presence of mouse anti-PD-1 antibody EH12.2H7 at 3.3 µg/ml and 10 µg/ml respectively. These data indicate TIG1 has the functional capacity to enhance antigen specific T cell cytokine responses.

Example 9: Human T Cell Proliferative Response to Tetanus Toxoid is Enhanced by TIGIT Blockade The ability of murine anti-TIGIT antibodies to enhance antigen-specific T cell responses was examined using an in vitro antigen-specific recall assay to tetanus toxoid (see, e.g., Piersma et al., *Vaccine*. 2006 Apr. 12; 24(16):3076-83; Zaunders et al., *J Immunol*. 2009 Aug. 15; 183(4):2827-36). PBMCs from human volunteers vaccinated with tetanus toxoid were obtained (iQ Biosciences) as described in Example 8. PBMCs were labeled with carboxyfluorescein succinimidyl ester (CFSE) (ThermoFisher), a reagent used for in vitro and in vivo labeling of cells to trace multiple generations using dye dilution by flow cytometry. 250,000 CFSE-labeled PBMCs were cultured in AIM-V medium (Invitrogen) in 96-well round bottom plates (Nunc). 2 µg/ml tetanus toxoid (Astarte Biologics, LLC) was added to each well in the presence of mouse anti-PD-1 antibody (Biolegend clone EH12.2H7) or TIG1 at 2.5 µg/ml, 5 µg/ml, or 10 µg/ml in each well. Cells were incubated for 4 days at 37° C. in a 5% CO2 incubator. On Day 4, IL-2 [50 units/ml] (Peprotech) was added to the cultures and on Day 6, PBMCs were collected for proliferative measurements by flow cytometry (BD FACSCalibur) for CFSE dilution on CD4+ T cells or CD8+ T cells.

Figure 17:
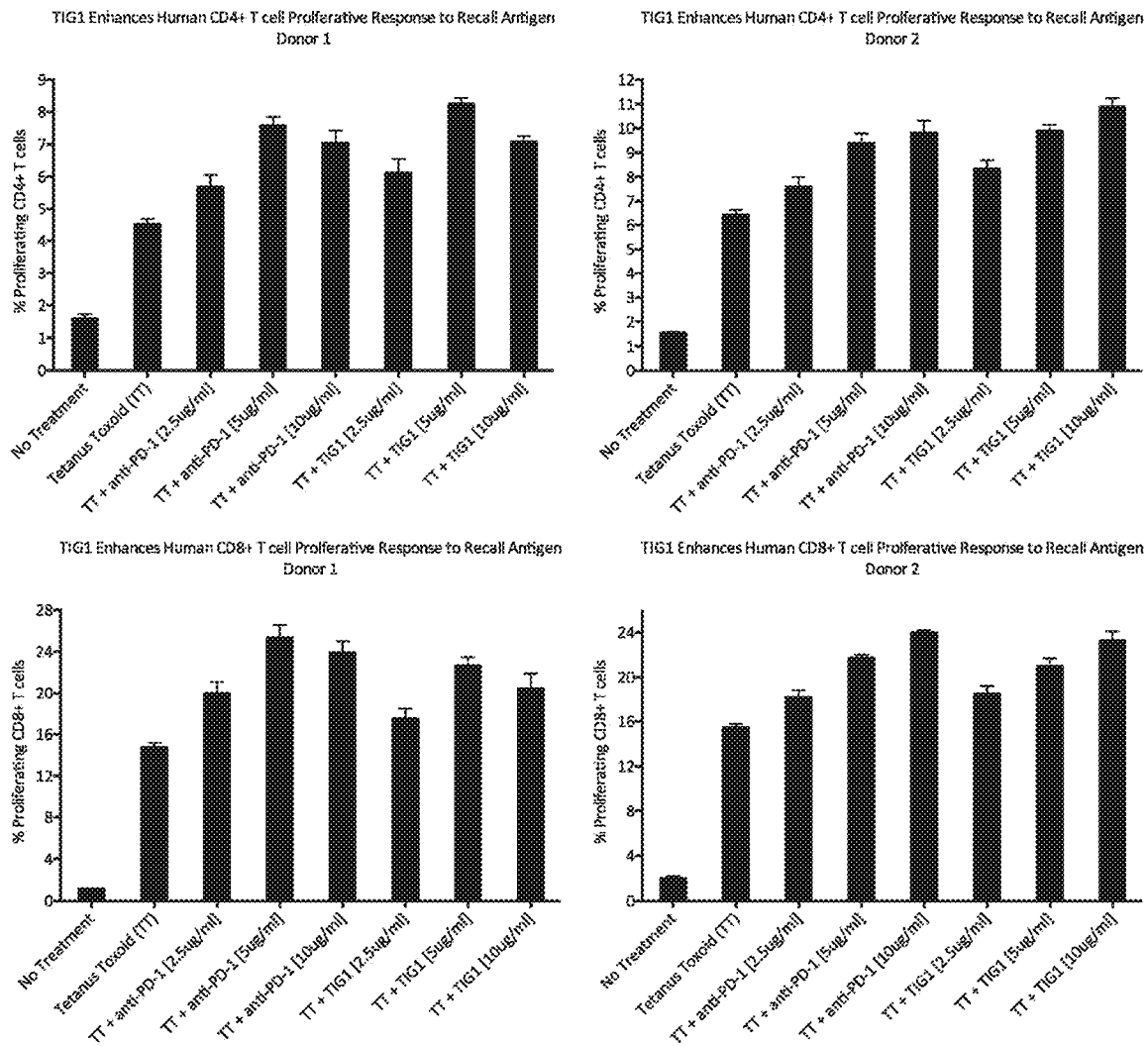
FIG. 17 depicts increased CD4+ and CD8+ T cell proliferation by TIG1 in an antigen-specific recall stimulation.

As shown in FIG. 17 (top panels), tetanus toxoid induced proliferation of 4.5% and 6.5% of human CD4+ T cells derived from donors 1 and 2, respectively. The addition of TIG1 further enhanced CD4+ T cell proliferation at all antibody concentrations tested (2.5 µg/ml, 5 µg/ml and 10 µg/ml) with similar proliferative effects observed with the anti-PD-1 antibody at those dose ranges.

As shown in FIG. 17 (bottom panels), tetanus toxoid induced proliferation of 15% and 15.5% of human CD8+ T cells derived from donors 1 and 2 respectively. The addition of TIG1 further enhanced CD8+ T cell proliferation at all antibody concentrations tested (2.5 µg/ml, 5 µg/ml and 10 µg/ml) with similar proliferative effects observed with anti-PD-1 antibody EH12.2H7 at those dose ranges. These results demonstrate that TIG1 has the capacity to enhance antigen specific T cell proliferative responses.

Example 10: Increase of NK Cell-Mediated Cytotoxicity with Human Primary Effector Cells and K562 Target Cells by TIGIT Blockade Human NK cells are able to elicit natural cytotoxicity to target cells that lack MHC I such as K562, a chronic myelogenous leukemia (CML) cell line (see, e.g., Nagel et al., *Cancer Res* 1981; 41:2284-2288; Andersson et al., *Int J Cancer*. 1979 February; 23(2):143-7; Lozzio et al., *Leuk Res*. 1979; 3(6):363-70). The expression of CD155 (PVR) on K562 cells (ATCC) was confirmed using a commercial antibody (Biolegend anti-CD155 clone SKII.4). As shown in FIG. 18 (top panel), 98% of K562 cells were found to express high levels of CD155 (black histogram). TIGIT expression on human CD56-positive NK cells in PBMCs (iQ Biosciences) using commercial antibodies (eBiosciences anti-TIGIT clone MBSA43 and Biolegend anti-CD56 clone HCD56) was also confirmed on 3 representative human donors (FIG. 18, bottom panels).

Figure 19:
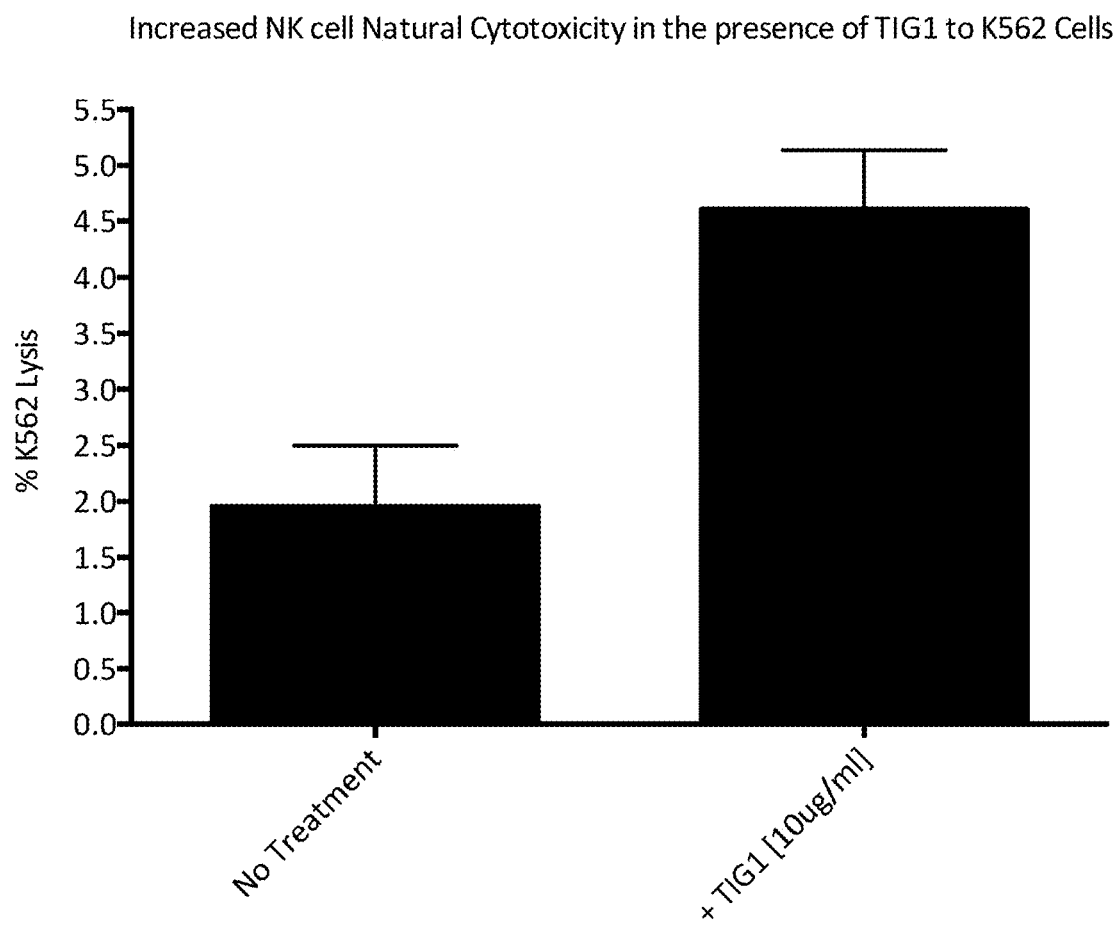
FIG. 19 depicts enhanced NK cell mediated cytotoxicity by TIG1 on K562 target cells.

Lysis of K562 cells mediated by NK cells were measured with and without TIG1. PBMCs were cultured overnight in AIM-V medium (Invitrogen) in the presence of interleukin-2 (IL-2) [200 units/ml] (Peprotech) at 37° C. in a 5% CO2 incubator. The following day, K562 cells were CFSE labeled and co-cultured 1:100 with PBMCs (Target:PBMCs; one K562 cell to one hundred PBMCs that contain approximately 5% NK cells) for 4 hours at 37° C. in a 5% CO2 incubator in the presence of 10 µg/ml TIG1. Following incubation period, cells were harvested and stained with 5 nM Sytox Red (ThermoFisher) to distinguish dead target cells by (CFSE+Sytox Red+). Percentages of K562 target cells lysed by NK cells were determined by flow cytometry (FACSCalibur; FlowJo Analysis). As shown in FIG. 19, 2% K562 cells were lysed without TIG1. When TIG1 was added, 4.4% K562 cells were lysed. The addition of TIG1 enhanced NK cell mediated natural cytotoxicity of K562 cells by two-fold, demonstrating that TIG1 has the capacity to increase the level of target cell killing by the subset of human effector cells.

Example 11: SEB-Induced Human T-Cell Cytokine Production is Enhanced by TIGIT Blockade Superantigens such as SEB (*Staphylococcus* Enterotoxin B), activate T-cells by linking MHC class II molecules on antigen presenting cells to the vβ element of the TCR resulting in the production of cytokines including interleukin-2 (IL-2), interleukin-6 (IL-6), tumor necrosis factor alpha (TNFα), and interferon gamma (IFNγ) (see, e.g., Krakauer et al., *Toxins* (Basel). 2010 August; 2(8): 1963-1983). Compared to a typical recall antigen-induced T-cell response where 0.1-0.001% of the T cells might be activated, SEB is capable of activating up to 10-20% of the T-cells in human blood depending on the fraction of T cells bearing the vβ3, vβ12, vβ14, and vβ17 found in each particular blood donor. Therefore, SEB can be used for a T cell based cytokine secretion assay to determine the level of target modulation by TIGIT blockade with human whole blood cells (WBC).

Freshly isolated WBC samples (Stanford Blood Center) were obtained using sodium heparin within 4 hours of draw with no visual signs of hemolysis. 250 µl were aliquoted to wells in a 96-well round bottom plates (Nunc) and stimulated with SEB (Toxin Technology) at 1 µg/ml final concentration in the presence of 10 µg/ml a humanized anti-PD-1 monoclonal antibody or 10 µg/ml HuTIG1-IgG1.AA for 24 hours at 37° C. in a 5% CO2 incubator. After 24 hours, 96-well plates are briefly centrifuged to separate the plasma layer for collection. Following plasma sample collection, the expression level of IL-2, IL-6, TNFα and IFNγ were measured by cytokine bead arrays (Biolegend, LEGENDplex™ Human CD8/NK Panel) by flow cytometry (BD FACSCalibur) and analyzed with Biolegend software for quantitative measurement.

Figure 20:
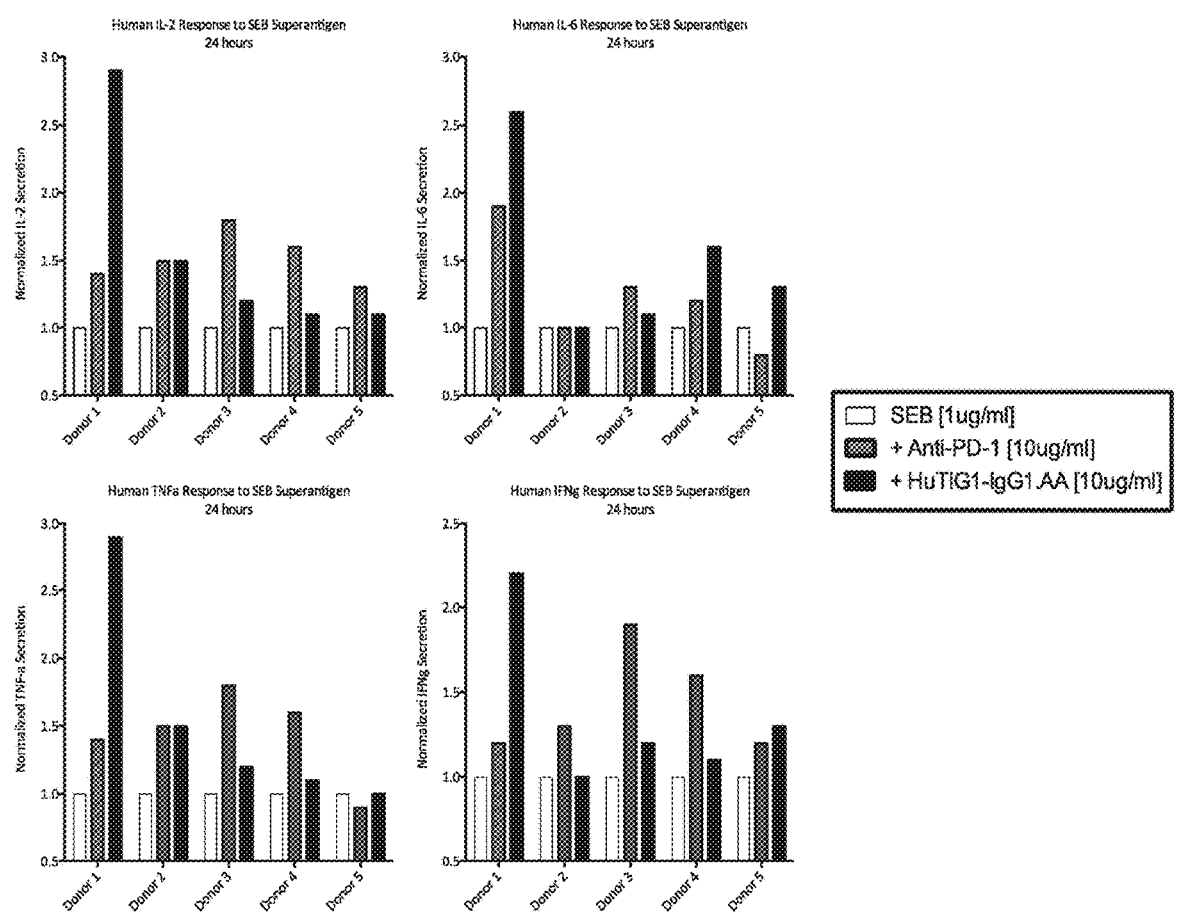
FIG. 20 indicates that HuTIG1-IgG1.AA potentiates cytokine effector responses.

To determine the change of the expression level of each of IL-2, IL-6, TNFα and IFNγ, the cytokine level in the presence of a test antibody (plus SEB) is divided by the cytokine level in the absence of antibody for each donor. A 2-fold change (e.g. detected in the presence of anti-TIGIT) thus means that the absolute concentration of cytokines measured in the experiment is twice the amount found in the SEB-stimulated control conditions. As shown in FIG. 20, SEB-stimulated IL-2, IL-6, TNFα, or IFNγ production by healthy donor blood cells was enhanced in the presence of 10 µg/ml humanized anti-PD-1 or 10 µg/ml of HuTIG1-IgG1.AA. Under these conditions, SEB-induced cytokine production by WBCs and its modulation by HuTIG1-IgG1.AA is a read-out of potentiation of cytokine effector responses. HuTIG1-IgG1.AA was capable of potentiating immune responses as demonstrated by stimulation of the production of IL-2, IL-6, TNFα and IFNγ in the assay shown here.

Figure 21:
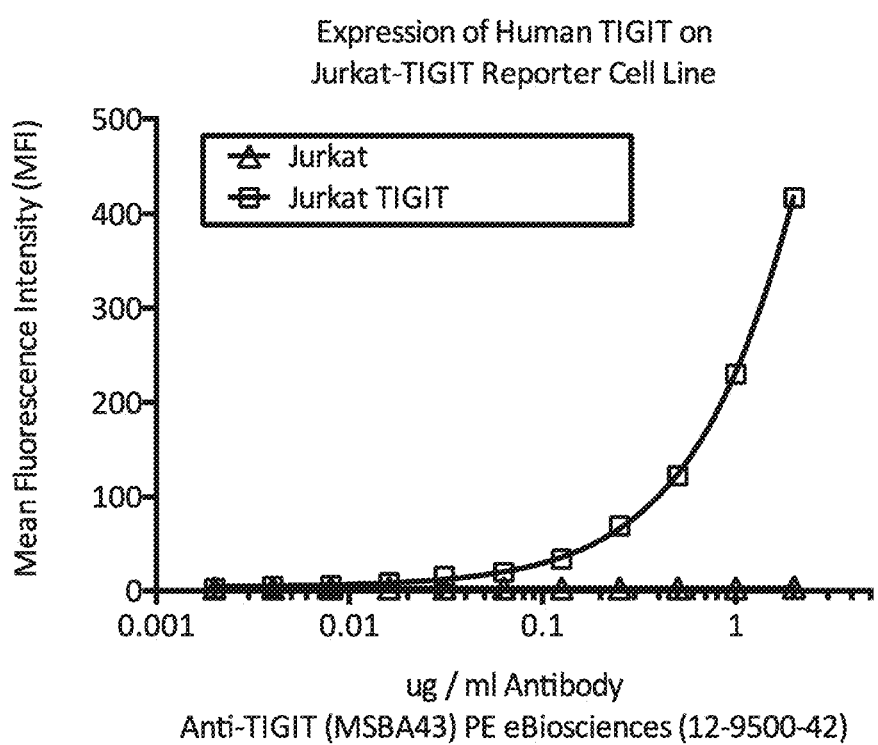
FIG. 21 depicts Jurkat-TIGIT cell line expression of human TIGIT on its cell surface.

Example 12: Characterization of HuTIG1-IgG1.AA and HuTIG3-IgG1.AA Mediated Complement-Dependent Cytotoxicity Complement-dependent cytotoxicity (CDC) refers to the lysis of a cell that expresses its target molecules in the presence of complement (see, e.g., Gazzano-Santoro et al., *J. Immunol. Methods,* 202:163). Activation of the classical complement pathway is initiated by the binding of the first component of the complement system (C1q) to antibodies (of the appropriate subclass), which are bound to their cognate antigen on the cell surface. To assess complement activation, a human T cell Jurkat dual reporter parental cell line (Dual Jurkat; Invivogen) was engineered to stably express human TIGIT (Jurkat-TIGIT) on the surface. As shown in FIG. 21, the expression of TIGIT on the surface of Jurkat-TIGIT cells was confirmed by flow cytometry with a commercial PE-labeled anti-TIGIT antibody (eBiosciences clone MSBA43). Jurkat-TIGIT was therefore used as target cells that constitutively express membrane bound TIGIT and thus can be subjected to antibody bound CDC activity in the presence of complement.

A CDC assay was performed with Jurkat-TIGIT cells and human complement in the presence of HuTIG1-IgG1.AA, HuTIG3-IgG1.AA, or rabbit anti-thymocyte globulin (ATG) (Fresenius Biotech GmbH) with increasing concentrations up to 50 ATG was used as a positive control due to its reactivity with Jurkat cells and documented complement-dependent cytotoxicity activity with Jurkat cells (see, e.g., Eiermann et al., *J Hematother Stem Cell Res.* 2001 June; 10(3):385-90; Ayuk et al., *AntiCancer Research* 29: 1355-1360 (2009). 50,000 Jurkat-TIGIT cells in RPMI 1640 medium (Invitrogen) containing 10% fetal bovine serum (FBS) were seeded into a 96-well round bottom plates (Nunc). Treatment antibodies were added starting at a top concentration of 50 µg/ml followed by a three-fold dilution series and allowed to incubate with cells for 1 hour at 37° C. in a 5% CO2 incubator. After this 1 hour incubation, human complement was added and allowed to incubator for an additional 3 hours at 37° C. in a 5% CO2 incubator. Following the completion of this 3 hour incubation, 5 µg/ml of propidium iodide (ThermoFisher) was added and samples were analyzed by flow cytometry (BD FACSCalibur) to determine the percentages of propidium iodide positivity as a readout for cell death.

Figure 22:
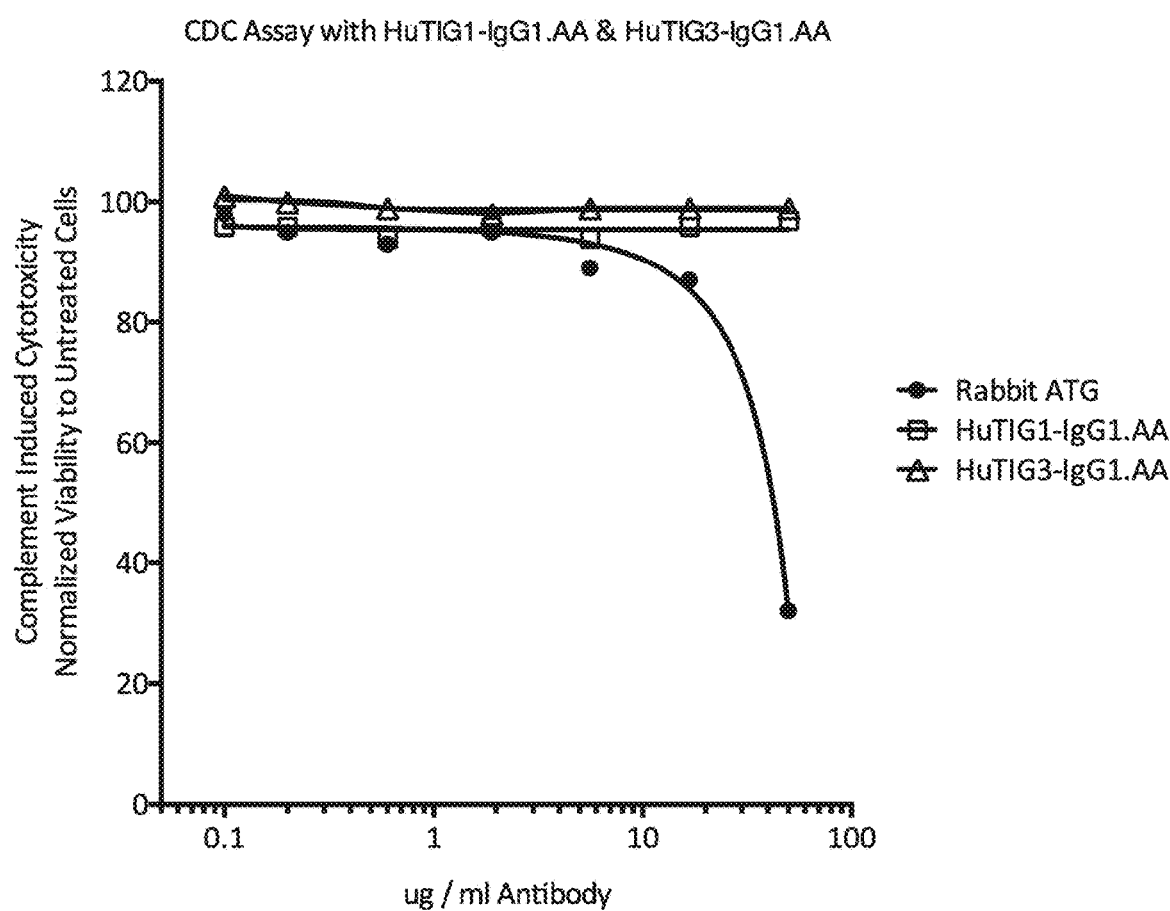
FIG. 22 indicates that HuTIG1-IgG1.AA and HuTIG3-IgG1.AA do not elicit CDC activity.

To determine normalized changes, the viability percentages were measured by flow cytometry and the percentage of propidium iodide positive cells were evaluated as dead cells. Untreated sample values were normalized to 100%. The viability percentages of samples in the presence of antibody are divided by the normalized untreated to give a fold change in viability. As shown in FIG. 22, neither HuTIG1-IgG1.AA nor HuTIG3-IgG1.AA up to 50 µg/ml induced CDC activity. These data demonstrate that binding of neither HuTIG1-IgG1.AA nor HuTIG3-IgG1.AA to TIGIT leads to complement mediated cell death of T cells.

Example 13: Jurkat Dual Reporter Cell Line Characterization of HuTIG1-IgG1.AA and HuTIG3-IgG1.AA The functional consequence of blocking human TIGIT receptor was analyzed using Jurkat-TIGIT reporter cell line which carries in the chromosome a secreted luciferase reporter gene which is driven by an IFNβ minimal promoter fused to five copies of the NF-κB consensus transcriptional response element and three copies of the c-Rel binding site. Jurkat-TIGIT cells also express a secreted embryonic alkaline phosphatase (SEAP) reporter gene under the control of an ISG54 minimal promoter in conjunction with five IFN-stimulated response elements.

The assays include two cell lines representing T effector cells (Jurkat-TIGIT) and antigen-presenting cells. The T effector cells stably express a luciferase reporter that is activated downstream of T cell receptor (TCR). The antigen-presenting cells (artificial antigen-presenting cells, or "aAPC") stably express a T cell activator protein that binds and activates the T effector cell, such as Jurkat-TIGIT, in an antigen-independent manner (Promega). The aAPC cells are further engineered to express the CD155. When the T effector cell is co-cultured with its corresponding aAPC cell, the interaction of TIGIT with CD155 inhibits the activation of T effector cells and reduces the expression of luciferase. Addition of an anti-TIGIT blocking antibody releases the inhibitory signal allowing expression of luciferase activity.

In this assay, 16,000 aAPC that express human CD155 and a T cell activator protein (TCR Activator CD155 CHO-K1) (Promega) are plated onto a 96-well half-area plate and incubated at 37° C. in a 5% CO2 incubator for 24 hours. The next day, 50,000 human Jurkat-TIGIT cells were co-cultured with TCR Activator CD155 CHO-K1 cells in the absence or presence of HuTIG1-IgG1.AA or HuTIG3-IgG1.AA starting at 10 µg/ml of with a two-fold dilution series for an additional 24 hours. Supernatants were collected and secreted luciferase measured using QUANTI-Luc (Invivogen) and a multimode plate reader (Perkin Elmer EnSpire) as relative light units. To determine relative light unit fold changes, the relative light units of the Jurkat-TIGIT co-cultured with TCR Activator CD155 CHO-K1 in the presence of various concentrations of anti-TIGIT antibodies is divided by the relative light units in the absence of antibody. Therefore as an example, a 2-fold increase (e.g. detected in the presence of anti-TIGIT) thus means that the relative light units measured in the experiment is twice the amount found in the TCR-activator only stimulated control conditions.

Figure 23:
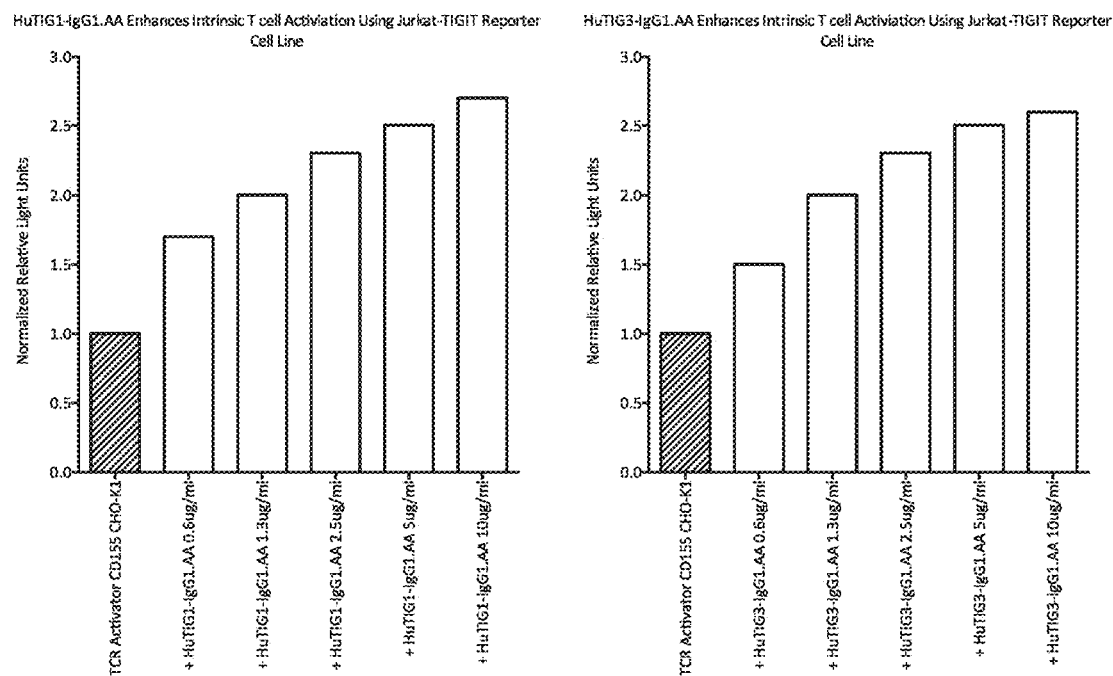
FIG. 23 shows that HuTIG1-IgG1.AA and HuTIG3-IgG1.AA increased intrinsic T cell activation in an in vitro T-cell antagonistic activity assay for anti-human TIGIT antibodies.

As shown in FIG. 23, both HuTIG1-IgG1.AA and HuTIG3-IgG1.AA were able to increase intrinsic T cell activation signaling as determined by the increasing relative light units induced in the presence of each blocking TIGIT antibody from 0.6 µg/ml to 10 µg/ml by an approximately 1.5 to 2.5 fold increase. These data demonstrate that anti-TIGIT antibodies have antagonistic activity by blocking the function of TIGIT and increase intrinsic T cell activity.

Example 14: Competitive Binding to TIGIT

Flow cytometry is used to identify an antibody that competes with TIG1 for binding to human TIGIT. TIG1 is labeled with a fluorescent dye FITC using Pierce FITC Antibody Labeling Kit (Thermo Fisher Scientific) according to the manufacturer's protocol. Binding of the resulting FITC-labeled TIG1 to human TIGIT is examined by flow cytometry using NS0-hTIGIT cells. One hundred thousand NS0-hTIGIT cells are incubated with various concentrations of FITC-labeled TIG1, starting at 10 µg/ml and two-fold serial dilutions, in 200 µl of FACS Buffer (PBS containing 0.5% bovine serum albumin and 0.05% sodium azide) at 4° C. for 30 min. After washing with 2 ml of FACS Buffer, NS0-hTIGIT cells are suspended in 0.2 ml of FACS Buffer and subjected to flow cytometry analysis using a FACScan flow cytometer (BD Biosciences, San Jose, Calif.) and the mean channel fluorescence (MCF) at each antibody concentration is obtained. The sub-saturating concentration, where 90% of the maximal fluorescence level is achieved, is determined for FITC-labeled TIG1.

The sub-saturating concentration of FITC-labeled TIG1 is incubated with one hundred thousand NS0-hTIGIT cells in the presence (or absence) of a 200-fold higher concentration of a test antibody in 200 µl of FACS Buffer at 4° C. for 30 min. For example, when 0.1 µg/ml of FITC-labeled TIG1 is used for binding to NS0-hTIGIT cells, 20 µg/ml of the test antibody is added to the cell suspension. As a background control, one hundred thousand NS0-hTIGIT cells are incubated without any antibodies. After washing with 2 ml of FACS Buffer, NS0-hTIGIT cells are suspended in 0.2 ml of FACS Buffer and subjected to flow cytometry analysis.

The MCF of NS0-hTIGIT cells incubated with FITC-labeled TIG1 [MCF A] is normalized to 100%, and the MCF of NS0-hTIGIT cells incubated with no antibodies [MCF B] is normalized to 0%. The MCF of NS0-hTIGIT cells incubated with FITC-labeled TIG1 and the test antibody [MCF C] is normalized by the following formula: 100×([MCF C]−[MCF B])/([MCF A]−[MCF B]). When the normalized MCF of NS0-hTIGIT cells incubated with FITC-labeled TIG1 and the test antibody is less than 20%, the test antibody is determined to compete with TIG1 for binding to human TIGIT.

The same assay can be used to identify antibodies that compete with TIG2 or TIG3.

Example 15: Affinity Measurement

The antigen-binding affinity of monoclonal antibodies can be measured by label-free optical surface plasmon resonance (SPR) biosensors, such as Biacore T100 (GE Healthcare Life Sciences, Marlborough, Mass.), ProteOn XPR36 (Bio-Rad, Hercules, Calif.), Octet RED384 (ForteBio, Menlo Park, Calif.) and IBIS MX96 (Wasatch Microfluidics, Salt Lake City, Utah) (Yang et al., *Anal. Biochem.* 508:78-96, 2016). The antigen-binding affinity of each of TIG1, TIG2 and TIG3 is measured using Biacore T100 as described by Yang et al. (supra). Protein A/G (Thermo Fisher Scientific) is immobilized onto flow cells in a CM5 sensor chip (GE Healthcare Life Sciences) using a standard coupling protocol. A test antibody (TIG1, TIG2 or TIG3) is captured by protein A/G on the CM5 sensor chip. Various concentrations of recombinant human TIGIT proteins, such as Recombinant Human TIGIT, His tagged (Creative BioMart, Shirley, N.Y.), are used in a flow for binding to the test antibody on the sensor chip. The on-rate (ka) and off-rate (kd) of the interaction between the test antibody and human TIGIT are obtained using the BIAevaluation software (GE Healthcare Life Sciences). The association constant (Ka) is calculated by dividing the on-rate (ka) by the off-rate (kd) for each of TIG1, TIG2 and TIG3. The dissociation constant (Kd) is calculated by dividing the off-rate (kd) by the on-rate (ka).

Biosensor studies for HuTIG1-IgG1.AA were run on a BioRad ProteOn XPR36 system in 10 mM HEPES, 150 mM NaCl, pH 7.4, 0.005% TWEEN®-20 (polysorbate 20) and 0.2 mg/ml BSA at 25° C. HuTIG1-IgG1.AA was diluted to 3.7, 1.2 and 0.4 nM and captured for 5 minutes onto a GLM sensor chip coated with ~10,000 RU of GE's anti-human IgG antibody. His-tagged soluble recombinant human TIGIT (Cat # TIT-H52H3; Acro Biosystems, Newark, Del.) was tested at 100 nM as the highest concentration in a 3-fold dilution series down to 1.2 nM. The data from the three different density antibody surfaces were globally fit to a 1:1 interaction model using a local Rmax. The obtained on-rate (ka) and off-rate (kd) are $(4.42\pm0.02)\times10^5$ $M^{-1}s^{-1}$ and $(4.09\pm0.02)\times10^{-4}$ $s^{-1}$, respectively. The calculated dissociation constant (Kd) is 925±7 pM.

Example 16: Epitope Mapping

To localize the epitope recognized by each of TIG1, TIG2 and TIG3 in the TIGIT molecule, single amino acid substitution mutants were generated in the extracellular region of TIGIT (SEQ ID NO:3) by site-directed mutagenesis using the overlap-extension PCR method (Higuchi, R., 1989, in "PCR Technology: Principles and Applications for DNA Amplification", Erlich, H. A., ed., Stockton Press, New York, N.Y., pp 61-70). The following six mutants in the extracellular region of TIGIT were used for the assay: Q35A (SEQ ID NO:50), N37A (SEQ ID NO:51), E39A (SEQ ID NO:52), N49A (SEQ ID NO:53), D51A (SEQ ID NO:54) and F86A (SEQ ID NO:55). The letter on the left, number in the middle, and the letter on the right in the name of each mutant denote an amino acid residue in the wild-type TIGIT, location by counting from the N-terminal methionine residue in the extracellular region of TIGIT (SEQ ID NO:3), and an amino acid in the mutant, respectively. Amino acid residues are in single letter code. Each of these six mutants carries an amino acid substitution near the interface of the TIGIT-CD155 complex (Stengel, Proc. Natl. Acad. Sci. USA, 109:5399-5404, 2012).

A mammalian expression vector pFCm179 has the same structure as pFCm404 (FIG. 1), except that (i) the puromycin N-acetyl-transferase gene is replaced by the E. coli xanthine guanine phosphoribosyl transferase gene, and (ii) the extracellular region of human TIGIT is replaced by human IL-15. DNA fragments encoding the six alanine substitution mutants of the extracellular region of human TIGIT were individually introduced into pFCm179 to replace the IL-15-coding region. The resulting expression vectors, pFCm179-Q35A, pFCm179-N37A, pFCm179-E39A, pFCm179-N49A, pFCm179-D51A and pFCm179-F86A carry the Q35A, N37A, E39A, N49A, D51A and F86A mutants in the TIGIT-coding region, respectively, and express the same sequence of TIGIT-Fc fusion proteins encoded in pFCm404 except for a single amino acid substitution specific for each mutant.

Wild-type and mutant TIGIT-Fc fusion proteins were transiently expressed in the human embryonic kidney cell line HEK293. HEK293 cells were grown in DMEM containing 10% FCS at 37° C. in a 7.5% CO2 incubator. The expression vectors of the wild-type and mutant TIGIT-Fc fusion proteins (pFCm404, pFCm179-Q35A, pFCm179-N37A, pFCm179-E39A, pFCm179-N49A, pFCm179-D51A and pFCm179-F86A) were individually transfected into HEK293 cells using the polyethylenimine method (Durocher et al. Nucl. Acids Res. 30: e9, 2002). The production level of TIGIT-Fc fusion proteins in culture supernatants was measured by ELISA. In brief, an ELISA plate was coated with 100 µl/well of goat anti-human IgG Fc-specific polyclonal antibody (Sigma-Aldrich), 1/2,000-diluted in PBS at 4° C. overnight, washed with Wash Buffer, and blocked with 200 µl/well of ELISA Buffer for 20 min at room temperature. After washing with Wash Buffer, culture supernatants of transiently transfected HEK293 cells appropriately diluted in ELISA Buffer (100 µl/well) were applied to the ELISA plate. Purified hTIGIT-Fc was used as a standard. After incubating the ELISA plate for 30 min at room temperature and washing with Wash Buffer, bound Fc fusion proteins were detected using 100 µl/well of HRP-conjugated goat anti-human IgG polyclonal antibody (SouthernBiotech), 1,2000-diluted in ELISA Buffer. After incubating the plate for 30 min at room temperature and washing with Wash Buffer, color development was initiated by adding 100 µl/well of ABTS substrate (Sigma-Aldrich) and stopped with 100 µl/well of 2% oxalic acid. Absorbance was read at 405 nm.

Binding of each of mouse TIG1, TIG2 and TIG3 antibodies to the TIGIT mutants was examined by ELISA. An ELISA plate was coated with 100 µl/well of goat anti-human IgG Fc-specific polyclonal antibody (Sigma-Aldrich), 1/2,000-diluted in PBS at 4° C. overnight, washed with Wash Buffer, and blocked with 200 µl/well ELISA Buffer for 20 min at room temperature. After washing with Wash Buffer, 0.5 µg/ml of transiently expressed TIGIT-Fc fusion proteins, carrying either the wild-type TIGIT or one of the six TIGIT mutants, in ELISA Buffer (100 µl/well) were applied to the ELISA plate in duplicates for incubation at room temperature for 30 min. As a negative control, culture supernatants of untransfected HEK293 cells were used. After washing with Wash Buffer, 100 µl/well of 200 ng/ml of a test antibody (TIG1, TIG2 or TIG3) in ELISA Buffer (100 µl/well) was applied. After incubating the ELISA plate for 30 min at room temperature and washing with Wash Buffer, bound antibodies were detected using 100 µl/well of HRP-conjugated goat anti-mouse kappa chain polyclonal antibody (Bethyl Laboratories, Montgomery, Tex.), 1/2,000-diluted in ELISA Buffer. After incubating the plate for 0.5 hr at room temperature and washing with Wash Buffer, color development was initiated by adding 100 µl/well of ABTS substrate (Sigma-Aldrich) and stopped with 100 µl/well of 2% oxalic acid. Absorbance was read at 405 nm.

TABLE 1

Binding of TIG1, TIG2 and TIG3 to TIGIT mutants

| TIGIT mutant | Relative binding to TIGIT (%) | | |
|---|---|---|---|
| | TIG1 | TIG2 | TIG3 |
| Q35A (SEQ ID NO: 50) | −0.1 | 29.1 | 57.8 |
| N37A (SEQ ID NO: 51) | 0.8 | 75.1 | 83.5 |
| E39A (SEQ ID NO: 52) | 71.1 | 69.1 | 94.2 |
| N49A (SEQ ID NO: 53) | 0.5 | 42.6 | 37.2 |
| D51A (SEQ ID NO: 54) | 1.8 | 61.0 | 41.1 |
| F86A (SEQ ID NO: 55) | 49.5 | 40.5 | 43.2 |

For each of TIG1, TIG2 and TIG3, the relative binding to each TIGIT mutant was calculated in the following formula. The average absorbance with the wild type TIGIT-Fc fusion proteins [Abs A] was normalized to 100%, and the average absorbance with culture supernatants of untransfected HEK293 cells [Abs B] was normalized to 0%. The average absorbance with a mutant TIGIT-Fc fusion protein [Abs C] was normalized by the following formula: 100×([Abs C]−[Abs B])/([Abs A]−[Abs B]). The result is summarized in Table 1. The relative binding of TIG1 was less than 5% when an amino acid residue was substituted by alanine at position 35, 37, 49 or 51, indicating that the amino acid residues at these four positions are critical for the binding of TIG1 to TIGIT. None of the TIGIT mutants used in this assay abolished the binding of TIG2 and TIG3 to TIGIT.

Figure 24:
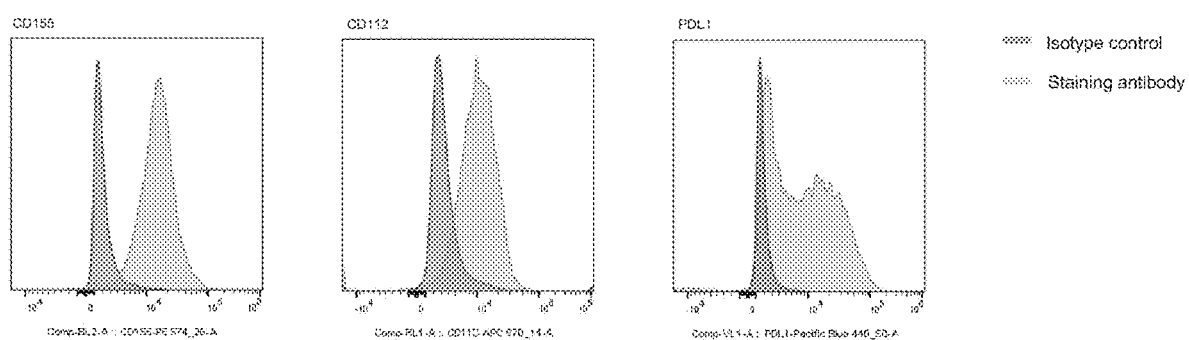
FIG. 24 depicts GM-CSF/IL-4 differentiated monocyte-derived dendritic cells (moDCs) expressed CD112, CD155 and PD-L1.

Example 17: Enhanced Secretion of IFNγ Upon Addition of HuTIG1-IgG1.AA, Anti-PD-L1 Antibody and HuTIG1-IgG1.AA in Combination with Anti-PD-L1 Antibody Human PBMCs were first isolated from a buffy coat by layering the blood on density gradient medium (Lymphoprep; STEMCELL; 07801) and collecting the PBMCs after centrifugation from the interphase. In a next step, human monocytes were isolated from the PBMCs by CD14 positive selection (EasySep Human CD14 Positive Selection kit; STEMCELL; Cat#18058) according to manufacturer protocol and cultivated for six days in RPMI medium supplemented with 5% FBS and 0.1 µg/ml GM-CSF (R&D; Cat#215-GM-050/CF) and 0.1 µg/ml IL-4 (R&D; Cat#204-IL-050/CF). Differentiated monocyte-derived dendritic cells (moDCs) were harvested and checked for expression of CD155, CD112 and PD-L1 by flow cytometry (FIG. 24).

Human CD4+ cells from 4 different donors were isolated from buffy coats by negative depletion (RosetteSep human CD4 T cell enrichment cocktail; STEMCELL; #15062) and purity was determined using flow cytometry.

moDCs and CD4+ cells were combined in a 1:4 ratio (25,000 moDCs; 100,000 CD4+ cells) and cultivated for four days in serum free medium (X-Vivo-20; LONZA; Cat#04-448Q) in the presence of HuTIG1-IgG1.AA (5 µg/ml or 15 µg/ml) or anti-PD-L1 antibody (10 µg/ml; clone 243.55.S1; SEQ ID NOs: 56 & 57) or both HuTIG1-IgG1.AA (15 µg/ml) and anti-PD-L1 antibody (10 µg/ml) for 4 days prior to IFNγ quantification using Cytometric Bead Array (CBA; Human IFNγ Flex Set; BD; Cat#560111). Human IgG1 Fc (25 µg/ml; BioXcell; Cat# BE0096) was used as control.

Figure 25:
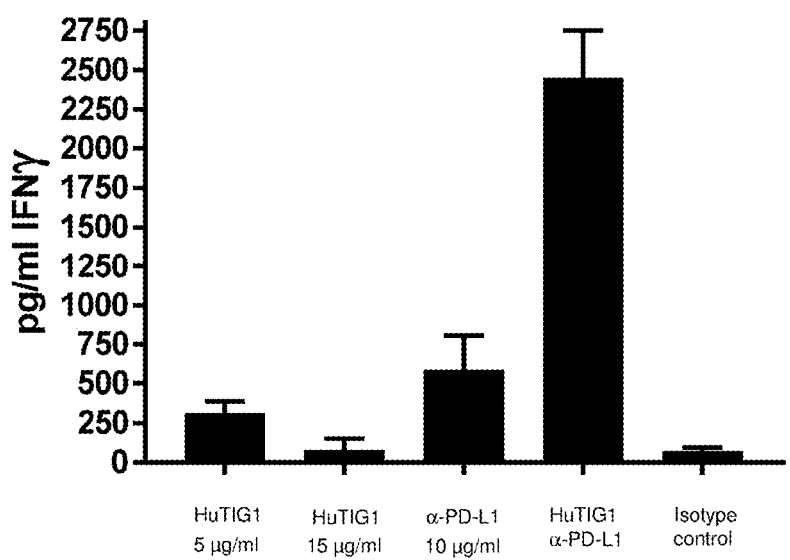
FIG. 25 depicts enhanced secretion of IFNγ upon addition of HuTIG1-IgG1.AA, anti-PD-L1 antibody and HuTIG1-IgG1.AA in combination with anti-PD-L1 antibody.

As shown in FIG. 25, HuTIG1-IgG1.AA and anti-PD-L1 antibody blockade independently increased production of IFNγ compared to appropriate isotype control antibody. Combination of HuTIG1-IgG1.AA with anti-PD-L1 antibody significantly and synergistically enhanced production of IFNγ compared to either monotherapy alone.

Figures 26A, 26B:
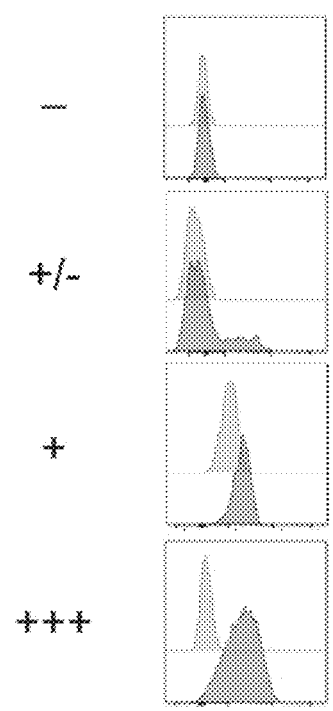
FIG. 26A depicts expression of TIGIT and CD96 on human lymphoid and myeloid cells.
FIG. 26B depicts representative histograms of anti-TIGIT staining at various expression levels.

Example 18: HuTIG1-IgG1.AA and HuTIG3-IgG1.AA Detect TIGIT Expressed on Human Lymphoid and Myeloid Cells Total human PBMCs isolated from ten donors were co-stained with directly conjugated antibodies delineating T cell, B cell, NK cell and myeloid-lineage subsets. Dead cells were excluded using Live/dead Fixable Aqua Dead Cell Stain kit. Expression of TIGIT was determined using HuTIG1-IgG1.AA and HuTIG3-IgG1.AA antibodies conjugated to Alexa647 dye. Expression of CD96 was determined using commercially available anti-CD96 antibody (clone NK92.39). In FIG. 26A, a plus (+) sign indicates expression above background with (+++) representing the highest expression observed. Plus/minus (+/−) sign indicates that only a subset of cells within the designated population express TIGIT or CD96 above background, and a minus (−) sign indicates a lack of expression above background. In all instances, background was determined using a modified Fluorescence Minus One (FMO) method in which all the fluorochromes used in the staining panel were added with the exception of the target antibody (i.e. HuTIG1-IgG1.AA, HuTIG3-IgG1.AA, anti-CD96 antibody). Rather, the target antibody was replaced with an IgG specific isotype control antibody of the same conjugation. FIG. 26B shows representative histograms of anti-TIGIT antibody staining in PBMCs at various expression levels which were used to assign expression levels of CD96 in FIG. 26A. Light histograms represent modified FMO. Dark histograms represent HuTIG1-IgG1.AA or HuTIG3-IgG1.AA staining.

Dissociated tumor cells from melanoma, colorectal cancer, non-small cell lung carcinoma, and renal clear cell carcinoma were purchased from a commercial source and stained with directly conjugated antibodies delineating T cell and antigen-presenting cell subsets. Leukocytes were identified using a pan isoform anti-CD45 antibody (clone HI30). Dead cells were excluded using Live/dead Fixable Aqua Dead Cell Stain kit. Expression of TIGIT was determined using HuTIG1-IgG1.AA antibody conjugated to Alexa647 dye. In all instances, background was determined using a modified Fluorescence Minus One (FMO) method in which all the fluorochromes used in the staining panel were added with the exception of the target antibody (i.e. HuTIG1-IgG1.AA). Rather, the target antibody was replaced with an IgG specific isotype control antibody of the same conjugation. FIG. 32B shows representative histograms of anti-TIGIT staining on tumor infiltrating lymphocytes (TILs) at various expression levels, shown in FIG. 32A. Light histograms represent modified FMO. Dark histograms represent HuTIG1-IgG1.AA staining.

Example 19: Epitope Mapping of Anti-Human TIGIT Antibody HuTIG1-IgG1.AA by Flow Cytometry Human TIGIT cDNA was cloned into pcDNA 3.1 (+) with a 9 residue hemagglutinin (HA) peptide tag followed by a 10 residue peptide linker inserted after the 21 residue native signal peptide and before the N-terminus of the mature TIGIT protein (SEQ ID NO:58). Amino acid residues of interest (T34, Q35, N37, E39, L44, I47, N49, D51, L52, H55, F86, I88, H90, Y92 and T96) in the extracellular region of human TIGIT were mutated to alanine, one amino acid at a time. Plasmids were purified and transiently transfected into CHO-K1 cells using Fugene 6 (Promega) transfection reagent according to manufacturer's recommendation. HA-tagged human TIGIT mutant expression was confirmed by anti-HA antibody detection.

For flow cytometry analysis of the anti-hTIGIT antibody binding epitope, HA-tagged human TIGIT proteins with or without single amino acid mutation were transiently transfected into CHO-K1 cells. After 24 hr, transfected cells were suspended in HBSS buffer (Thermo Fisher Scientific, Cat#14175095), and incubated with HuTIG1-IgG1.AA antibody at varying concentrations in 50 µL volume. After 1 hr incubation at 4° C., cells were washed and a second incubation with 50 µL Alexa488 conjugated anti-human IgG(H+L) secondary antibody (Thermo Fisher Scientific, Cat#A-11013) was performed to detect cells bound by antibody. Cells were incubated with an anti-HA antibody (Sigma, Cat# H7411) as a positive control, and non-transfected CHO-K1 cells were used as a negative control. The cells were analyzed on an Attune NxT Cytometer (Thermo Fisher Scientific) and the data were processed using FlowJo software. For each mutant, the saturating antibody binding MFI (mean fluorescence intensity) were normalized to 100% POC (percent of control), and no primary antibody binding control MFI were normalized to 0% POC. Data were then fit to a four parameter non-linear sigmoidal curve using Graph- Pad Prism 7 curve fitting using following formula: $Y=Bottom+(Top-Bottom)/(1+10^{((LogEC_{50}-X)*HillSlope)})$.

Figure 27:
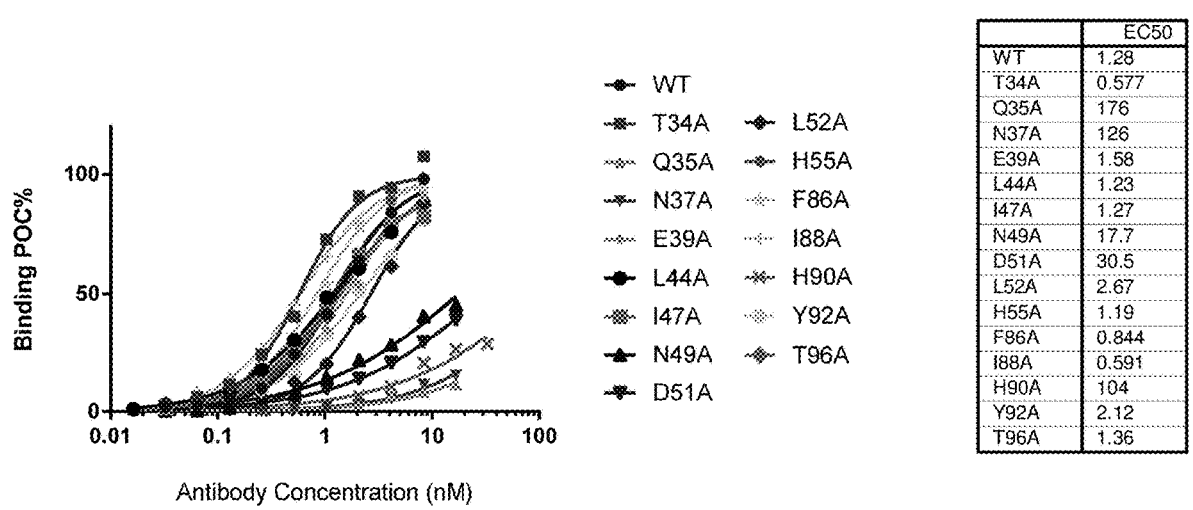
FIG. 27 depicts HuTIG1-IgG1.AA epitope mapping by flow cytometry.
Figure 28:
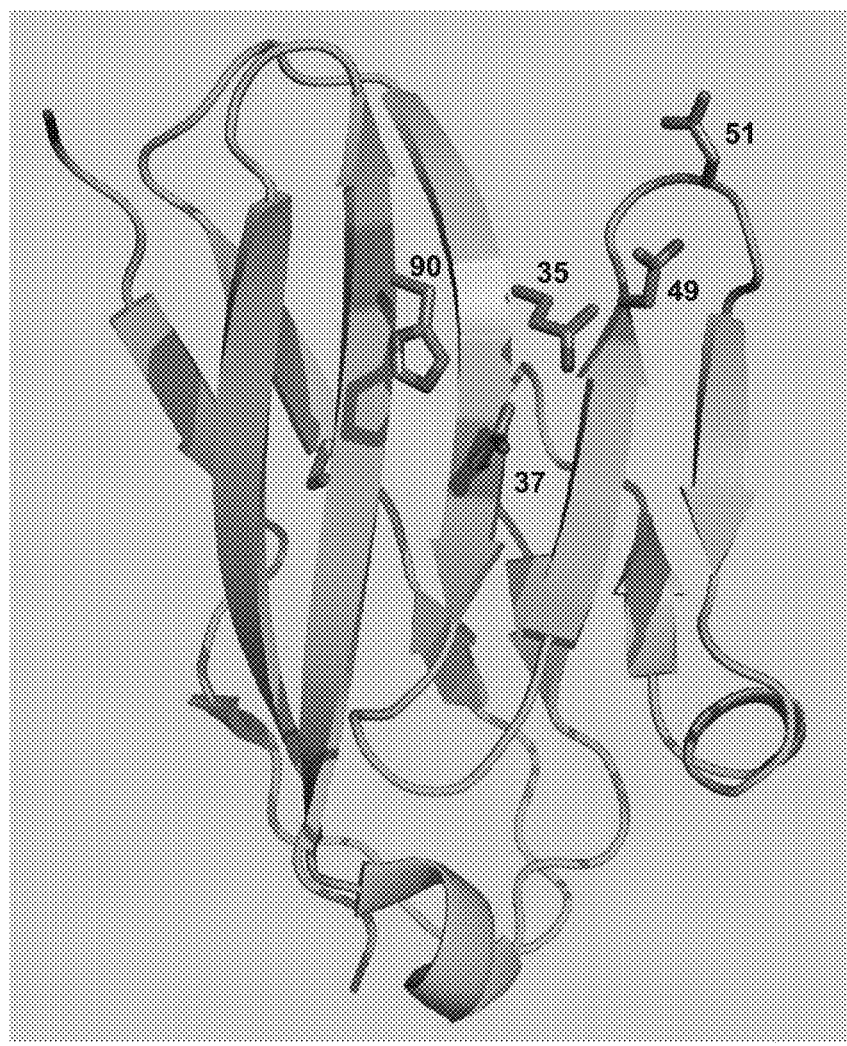
FIG. 28 depicts a ribbon representation of the extracellular IgV domain of human TIGIT with numbered epitope residue side-chains displayed in stick representation.

In this assay, HuTIG1-IgG1.AA bound to wild type human TIGIT with an $EC_{50}$=1.28 nM. Five of the fifteen single-point alanine TIGIT mutants bound HuTIG1-IgG1.AA with a greater than 10-fold decrease in binding affinity. Human TIGIT (SEQ ID NO: 3) with mutations N49A, D51A, H90A, N37A or Q35A bound HuTIG1-IgG1.AA with decreasing potency ranging from $EC_{50}$=17.7 to 176 nM, respectively (FIG. 27). All of these residues co-locate to one discrete region on the front β-sheet structure of the TIGIT IgV extracellular Domain (FIG. 28).

Example 20: Ex Vivo Immunophenotyping of T-Cell Subsets from Whole Blood of Non-Human Primates Dosed HuTIG1-IgG1.AA A pharmacokinetic study was performed by Charles River Laboratories (Reno, Nev.). The objective of this study was to examine ex vivo whole blood samples from cynomolgus monkeys treated with a single dose of 10 mg/kg of anti-TIGIT (HuTIG1-IgG1.AA) antibody for the indirect assessment of receptor occupancy for TIGIT.

Three experimentally naïve female cynomolgus monkeys (#67, #68 & #69) were administered with a single intravenous dose of 10 mg/kg HuTIG1-IgG1.AA antibody. Whole blood in sodium heparin samples were received within 24 hours of the last sampling time-point that corresponded with pre-dose, Day 1, 2, 7, 14, 21, and 28 post-dose time-points. For whole blood flow cytometry studies, fluorescently labeled anti-human TIGIT from BioLegend (clone MBSA43) was used to determine expression levels of TIGIT on cynomolgus monkey blood lymphocyte cell subsets as it has been shown to cross-react to non-human primates (*PLoS Pathog.* 2016 January; 12(1); BioLegend). Live cells were acquired by FACSCalibur and analyzed by FlowJo software.

Figure 29A:
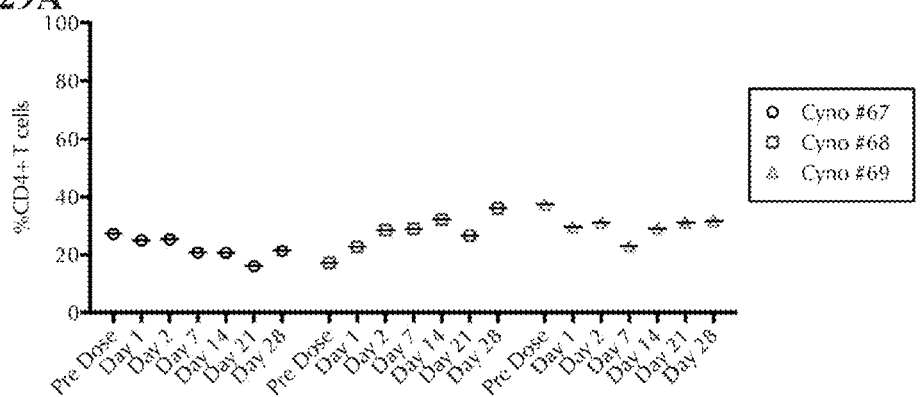
FIG. 29A and FIG. 29B depict the results of a CD4+ T-cell subset analysis for TIGIT expression.
Figure 29B:
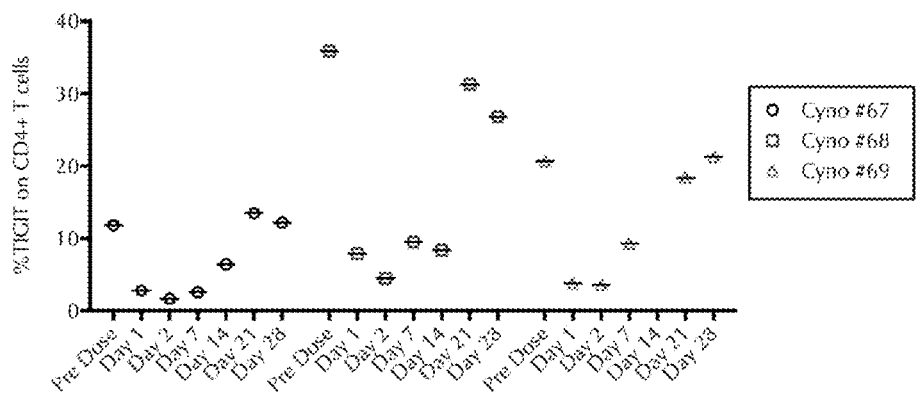
Figure 30A:
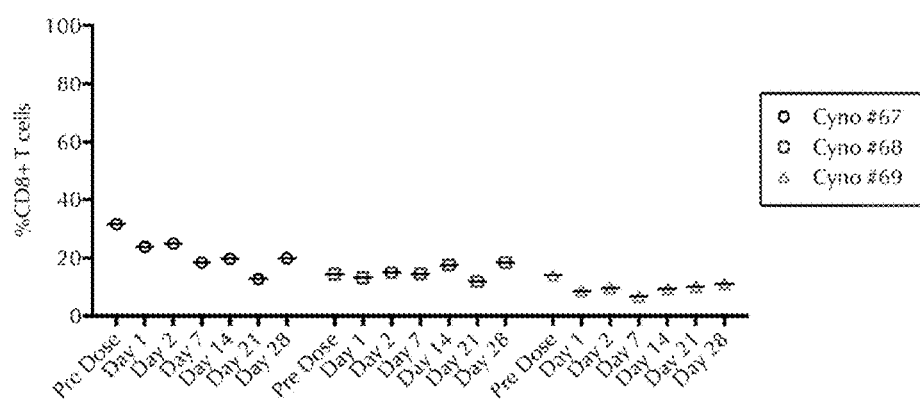
FIG. 30A and FIG. 30B depict the results of a CD8+ T-cell subset analysis for TIGIT expression.
Figure 30B:
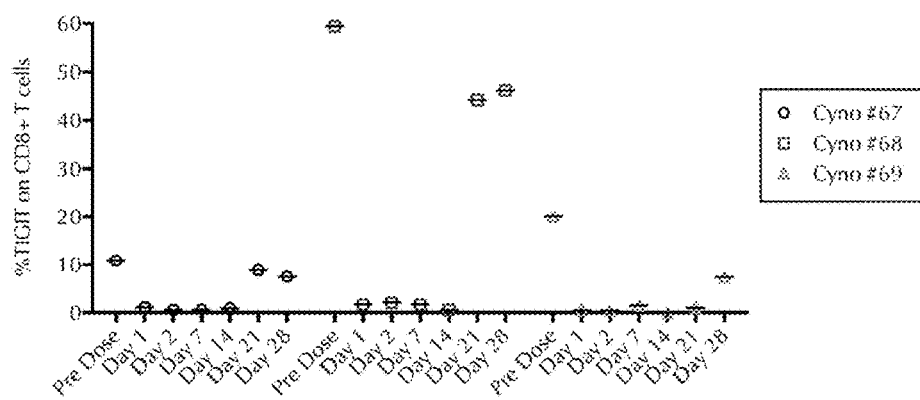

Anti-TIGIT (MBSA43) was able to bind both CD4+ and CD8+ T-cell subsets when staining pre-dose whole blood samples. Following dosing, anti-TIGIT (MBSA43) was unable to detect TIGIT expression on these T-cell subsets until Day 14 or 21 depending on the different monkey examined with levels returning to pre-dose detection levels by Day 21 or 28 depending on different animals examined (FIGS. 29B & 30B). This inability to detect TIGIT expression was not due to significant changes in CD4+ or CD8+ T cell frequency (FIGS. 29A & 30A, respectively) suggesting that surface TIGIT was occupied by the treatment antibody (HuTIG1-IgG1.AA) and not due to T-cell subset depletion.

These data support that anti-TIGIT antibody HuTIG1-IgG1.AA is cross-reactive to cynomolgus monkey and using anti-human TIGIT from BioLegend (clone MBSA43), provides an assessment of TIGIT receptor occupancy Example 21: Enhanced NK Cell Mediated Cytotoxicity by HuTIG1-IgG1.AA and HuTIG3-IgG1.AA on K562 Target Cells The NK cell-mediated cytotoxicity assay described in Example 10 was repeated using purified NK cells in place of PBMCs. To obtain sufficient and appropriate purified NK cells for these experiments, it is important to screen for donor PBMCs with high NK cell frequency, sufficient TIGIT surface expression, and sufficient CD226 expression. Peripheral Blood LeukoPak (consisting of 10 billion cells or more) were obtained and NK cell isolation was performed using Miltenyi autoMACS Pro Separator according to manufacturer's instructions (Miltenyi Biotec, catalog#130-092-657). Purified NK cells were re-suspended in medium containing interleukin-2 (IL-2) [200 units/ml] in 6-well plates. 6-well plates were placed at 37° C. in a 5% CO2 incubator for 24 hours prior to performing natural cytotoxicity studies with cells harvested from the wells.

Lysis of K562 cells mediated by purified NK cells were measured with and without anti-TIGIT antibody (TIG1). NK cells were cultured in RPMI 1640 medium (Invitrogen) in the presence of interleukin-2 (IL-2) [200 units/ml] (Peprotech) overnight at 37° C. in a 5% CO2 incubator. The following day, K562 cells were CFSE labeled and co-cultured 1:20 with NK cells (Target:NK; one K562 cell to twenty NK cells) for 4 hours at 37° C. in a 5% CO2 incubator in the presence of 10 μg/ml Rituxan or humanized anti-TIGIT antibodies (HuTIG1-IgG1.AA or HuTIG3-IgG1.AA). Rituxan was used as a negative control as K562 cells do not express CD20. Following the incubation period, cells were harvested and stained with 5 nM Sytox Red (ThermoFisher) to distinguish dead target cells by (CFSE+ Sytox Red+). Percentages of K562 target cells lysed by NK cells were determined by flow cytometry (FACSCalibur; FlowJo Analysis).

Figure 31:
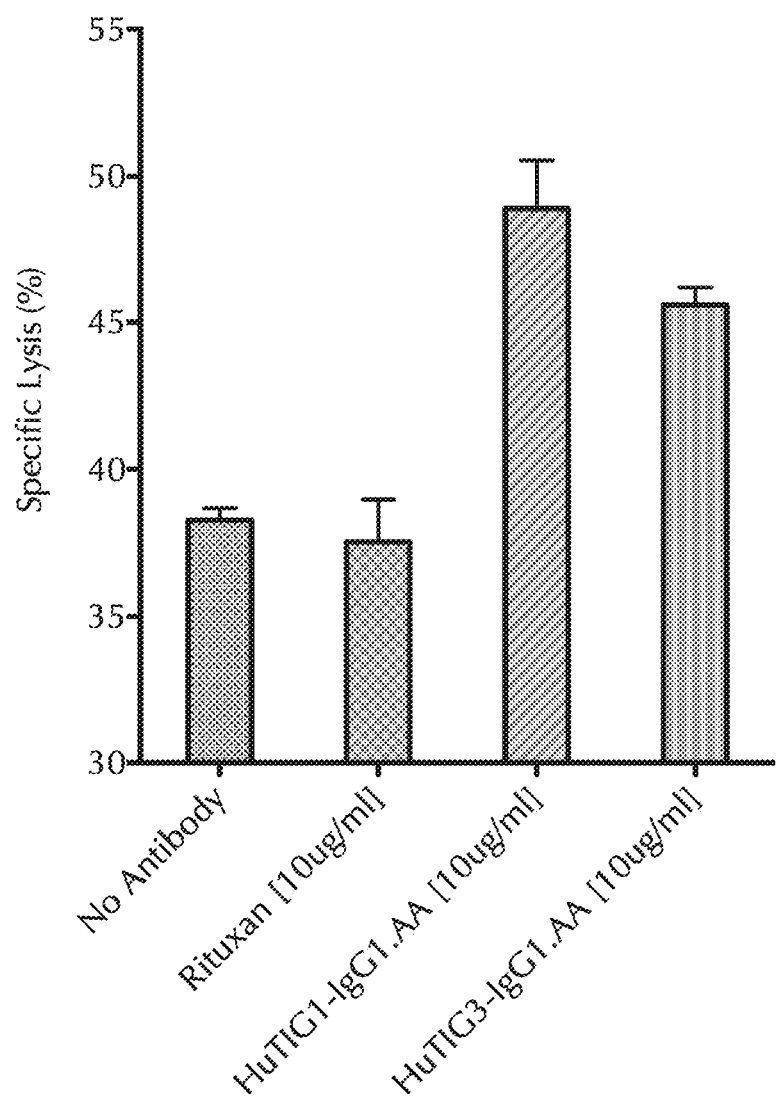
FIG. 31 depicts enhanced NK cell-mediated cytotoxicity by HuTIG1-IgG1.AA and HuTIG3-IgG1.AA on K562 target cells.

As shown in FIG. 31, when using purified NK cells, the addition of anti-TIGIT antibodies enhanced NK cell mediated natural cytotoxicity of K562 cells, demonstrating that anti-TIGIT antibodies (HuTIG1-IgG1.AA or HuTIG3-IgG1.AA) have the capacity to increase the level of target cell killing (by 28% or 19%, respectively, relative to 'No Antibody' or Rituxan normalized percentages) by the subset of human effector cells.

---

SEQUENCES

SEQ ID NO: 1: Amino acid sequence of mature human TIGIT:
MMTGTIETTGNISAEKGGSIILQCHLSSTTAQVTQVNWEQQDQLLAICNADLGWHISP
SFKDRVAPGPGLGLTLQSLTVNDTGEYFCIYHTYPDGTYTGRIFLEVLESSVAEHGAR
FQIPLLGAMAATLVVICTAVIVVVALTRKKKALRIHSVEGDLRRKSAGQEEWSPSAPS
PPGSCVQAEAAPAGLCGEQRGEDCAELHDYFNVLSYRSLGNCSFFTETG SEQ ID NO: 2: Amino acid sequence of the signal peptide upstream of the extracellular region of human TIGIT: MGWSWIFFFLLSGTASVLS SEQ ID NO: 3: Amino acid sequence of the extracellular region of human TIGIT (hTIGIT):
MMTGTIETTGNISAEKGGSIILQCHLSSTTAQVTQVNWEQQDQLLAICNADLGWHISP
SFKDRVAPGPGLGLTLQSLTVNDTGEYFCIYHTYPDGTYTGRIFLEVLESSVAEHGAR
FQIPTG SEQ ID NO: 4: Amino acid sequence of the polypeptide linker immediately downstream of hTIGIT: TGGG

| SEQUENCES |
|---|

SEQ ID NO: 5: Amino acid sequence of the human γ1 Fc region:
EPKSCDKTHTCPPCPAPELLGGPSVFLFPPKPKDTLMISRTPEVTCVVVDVSHEDPEV
KFNWYVDGVEVHNAKTKPREEQYNSTYRVVSVLTVLHQDWLNGKEYKCKVSNKA
LPAPIEKTISKAKGQPREPQVYTLPPSRDELTKNQVSLTCLVKGFYPSDIAVEWESNG
QPENNYKTTPPVLDSDGSFFLYSKLTVDKSRWQQGNVFSCSVMHEALHNHYTQKSL
SLSPGK SEQ ID NO: 6: Amino acid sequence of the extracellular region of human CD155:
DVVVQAPTQVPGFLGDSVTLPCYLQVPNMEVTHVSQLTWARHGESGSMAVFHQTQ
GPSYSESKRLEFVAARLGAELRNASLRMFGLRVEDEGNYTCLFVTFPQGSRSVDIWL
RVLAKPQNTAEVQKVQLTGEPVPMARCVSTGGRPPAQITWHSDLGGMPNTSQVPGF
LSGTVTVTSLWILVPSSQVDGKNVTCKVEHESFEKPQLLTVNLTVYYPPEVSISGYDN
NWYLGQNEATLTCDARSNPEPTGYNWSTTMGPLPPFAVAQGAQLLIRPVDKPINTTL
ICNVTNALGARQAELTVQVKEGPPSEHSGMSRNA SEQ ID NO: 7: Amino acid sequence of the extracellular region of human CD155 fused to
the human γ1 Fc region chain (hCD155-Fc):
DVVVQAPTQVPGFLGDSVTLPCYLQVPNMEVTHVSQLTWARHGESGSMAVFHQTQ
GPSYSESKRLEFVAARLGAELRNASLRMFGLRVEDEGNYTCLFVTFPQGSRSVDIWL
RVLAKPQNTAEVQKVQLTGEPVPMARCVSTGGRPPAQITWHSDLGGMPNTSQVPGF
LSGTVTVTSLWILVPSSQVDGKNVTCKVEHESFEKPQLLTVNLTVYYPPEVSISGYDN
NWYLGQNEATLTCDARSNPEPTGYNWSTTMGPLPPFAVAQGAQLLIRPVDKPINTTL
ICNVTNALGARQAELTVQVKEGPPSEHSGMSRNATGGGEPKSCDKTHTCPPCPAPEL
LGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAKGQPREPQ
VYTLPPSRDELTKNQVSLTCLVKGFYPSDIAVEWESNGQPENNYKTTPPVLDSDGSFF
LYSKLTVDKSRWQQGNVFSCSVMHEALHNHYTQKSLSLSPGK SEQ ID NO: 8: Amino acid sequence of the FLAG ® peptide (FLAG ®): DYKDDDDK SEQ ID NO: 9: Amino acid sequence of the glycosylphosphatidylinositol linkage signal of
human CD55 (GPI): PNKGSGTTSGTTRLLSGHTCFTLTGLLGTLVTMGLLT SEQ ID NO: 10: Amino acid sequence of TIG1 VH:
DVQLVESGGGLVQPGGSRKLSCAASGFTFSNFGMHWVRQAPEKGLEWVAFISSGSS
SIYYADTVKGRFTISRDNPKNTLFLQMTSLRSEDTAMYYCARMRLDYYAMDYWGQ
GTSVTVSS SEQ ID NO: 11: Amino acid sequence of TIG1 VH CDR1: NFGMH SEQ ID NO: 12: Amino acid sequence of TIG1 VH CDR2: FISSGSSSIYYADTVKG SEQ ID NO: 13: Amino acid sequence of TIG1 VH CDR3: MRLDYYAMDY SEQ ID NO: 14: Amino acid sequence of TIG1 VL:
DVQITQSPSYLAASPGETITINCRASKSISKYLAWYQEKPGKTNKLLIYSGSTLQSGIPS
RFSGSGSGTDFTLTISSLEPEDFAMYYCQQHNEYPWTFGGGTKLEIK SEQ ID NO: 15: Amino acid sequence of TIG1 VL CDR1: RASKSISKYLA SEQ ID NO: 16: Amino acid sequence of TIG1 VL CDR2: SGSTLQS SEQ ID NO: 17: Amino acid sequence of TIG1 VL CDR3: QQHNEYPWT SEQ ID NO: 18: Amino acid sequence of TIG2 VH:
EVQLQQSGPELVKPGASVKISCKTSGYTFTEYTMHWVKQSHGKNLEWIGGINPNNG
GTSYNQKFKGRATLTVDKSSSTAYMELRSLTSDDSAVYYCARPGWYNYAMDYWG
QGTSVTVSS SEQ ID NO: 19: Amino acid sequence of TIG2 VH CDR1: EYTMH SEQ ID NO: 20: Amino acid sequence of TIG2 VH CDR2: GINPNNGGTSYNQKFKG SEQ ID NO: 21: Amino acid sequence of TIG2 VH CDR3: PGWYNYAMDY SEQ ID NO: 22: Amino acid sequence of TIG2 VL:
DIVMTQSHKFMSTSVGDRVNITCKASQGVSTAVAWYQQKPGQSPKLLIYSASYRYT
GVPDRFTGSGSGTDFTFTISSVQAEDLAVYHCQQHYITPWTFGGGTKLEIK SEQ ID NO: 23: Amino acid sequence of TIG2 VL CDR1: KASQGVSTAVA SEQ ID NO: 24: Amino acid sequence of TIG2 VL CDR2: SASYRYT SEQ ID NO: 25: Amino acid sequence of TIG2 VL CDR3: QQHYITPWT

SEQUENCES

SEQ ID NO: 26: Amino acid sequence of TIG3 VH:
EVQLVESGGGLVKPGGSLKLSCAASGFAFSDYDMSWVRQTPEKRLEWVAYISDGGY
NTYYPDTVKGRFTISRDNAKNTLYLQMSSLKSEDTAIYYCARQILLRYYFDYWGQGT
TLTVSS SEQ ID NO: 27: Amino acid sequence of TIG3 VH CDR1: DYDMS SEQ ID NO: 28: Amino acid sequence of TIG3 VH CDR2: YISDGGYNTYYPDTVKG SEQ ID NO: 29: Amino acid sequence of TIG3 VH CDR3: QILLRYYFDY SEQ ID NO: 30: Amino acid sequence of TIG3 VL:
DIVMSQSPSSLAVSVGEKVTMTCKSSQSLLYSSNQKNYLAWYQQKPGQSPKLLIYW
ASTRESGVPDRFTGSGSGTDFTLTISSVKAEDLAVYYCQQYHSYPWTFGGGTKLEIK SEQ ID NO: 31: Amino acid sequence of TIG3 VL CDR1: KSSQSLLYSSNQKNYLA SEQ ID NO: 32: Amino acid sequence of TIG3 VL CDR2: WASTRES SEQ ID NO: 33: Amino acid sequence of TIG3 VL CDR3: QQYHSYPWT SEQ ID NO: 34: Amino acid sequence of the designed humanized TIG1 VH (HuTIG1 VH):
MDSRLNLVFLVLILKGVQCEVQLVESGGGLVQPGGSLRLSCAASGFTFSNFGMHWV
RQAPGKGLEWVAFISSGSSSIYYADTVKGRFTISRDNAKNSLYLQMNSLRAEDTAVY
YCARMRLDYYAMDYWGQGTMVTVSS SEQ ID NO: 35: Amino acid sequence of the mature HuTIG1 VH:
EVQLVESGGGLVQPGGSLRLSCAASGFTFSNFGMHWVRQAPGKGLEWVAFISSGSSS
IYYADTVKGRFTISRDNAKNSLYLQMNSLRAEDTAVYYCARMRLDYYAMDYWGQ
GTMVTVSS SEQ ID NO: 36: Amino acid sequence of the designed humanized TIG1 VL (HuTIG1 VL):
MRFQVQVLGLLLLWISGAQCDIQMTQSPSSLSASVGDRVTITCRASKSISKYLAWYQ
QKPGKAPKLLIYSGSTLQSGVPSRFSGSGSGTDFTLTISSLQPEDFATYYCQQHNEYP
WTFGGGTKVEIK SEQ ID NO: 37: Amino acid sequence of the mature HuTIG1 VL:
DIQMTQSPSSLSASVGDRVTITCRASKSISKYLAWYQQKPGKAPKLLIYSGSTLQSGV
PSRFSGSGSGTDFTLTISSLQPEDFATYYCQQHNEYPWTFGGGTKVEIK SEQ ID NO: 38: Nucleotide sequence of the synthetic HuTIG1 VH gene in pHuTIG1.AA:
ACTAGTACCACCATGGACTCCAGGCTCAATCTGGTTTTCCTTGTCCTTATTCTGAA
AGGCGTCCAGTGTGAAGTGCAGCTGGTGGAGTCTGGGGGAGGCTTGGTGCAGCC
TGGAGGGTCCCTGAGACTCTCCTGTGCAGCCTCTGGATTCACTTTCAGTAACTTTG
GAATGCACTGGGTTCGACAGGCTCCAGGGAAGGGGCTGGAGTGGGTCGCATTCA
TTAGTAGTGGCAGTAGTTCCATCTACTATGCAGACACAGTGAAGGGCCGATTCAC
CATCTCCAGAGACAATGCCAAGAACAGCCTGTACCTGCAAATGAACAGTCTGAG
GGCTGAGGACACTGCCGTGTATTACTGTGCAAGAATGAGACTGGATTACTATGCT
ATGGACTACTGGGGTCAAGGAACCATGGTCACCGTCTCCTCAGGTAAGTATGGCC
TCTAAGCTT SEQ ID NO: 39: Nucleotide sequence of the synthetic HuTIG1 VL gene in pHuTIG1.AA:
GCTAGCACCACCATGAGGTTCCAGGTTCAGGTTCTGGGGCTCCTTCTGCTCTGGA
TCTCAGGAGCCCAGTGTGATATCCAGATGACCCAGTCTCCATCTTCTCTTTCTGCA
TCTGTTGGAGATAGAGTCACTATTACTTGCAGGGCAAGTAAGAGCATTAGCAAAT
ATCTGGCCTGGTATCAACAGAAACCTGGGAAAGCTCCTAAGCTGCTTATCTACTC
TGGGTCCACTTTGCAATCTGGAGTTCCATCAAGATTCAGTGGCAGTGGATCTGGT
ACAGATTTCACTCTCACCATCAGTAGCCTGCAGCCTGAAGATTTTGCAACCTATT
ACTGTCAACAGCATAATGAATACCCCTGGACCTTCGGCGGAGGCACCAAAGTCG
AAATCAAACGTAAGTAGAATCCAAAGAATTC SEQ ID NO: 40: Amino acid sequence of the mature gamma heavy chain of HuTIG1-
IgG1.AA encoded in pHuTIG1.AA:
EVQLVESGGGLVQPGGSLRLSCAASGFTFSNFGMHWVRQAPGKGLEWVAFISSGSSS
IYYADTVKGRFTISRDNAKNSLYLQMNSLRAEDTAVYYCARMRLDYYAMDYWGQ
GTMVTVSSASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKVEPKSCDKT
HTCPPCPAPEAAGGPSVFLFPPKPKDTLMISRTPEVTCVVVDVSHEDPEVKFNWYVD
GVEVHNAKTKPREEQYNSTYRVVSVLTVLHQDWLNGKEYKCKVSNKALPAPIEKTI
SKAKGQPREPQVYTLPPSRDELTKNQVSLTCLVKGFYPSDIAVEWESNGQPENNYKT
TPPVLDSDGSFFLYSKLTVDKSRWQQGNVFSCSVMHEALHNHYTQKSLSLSPGK

SEQUENCES

SEQ ID NO: 41: Amino acid sequence of the mature kappa light chain of HuTIG1-IgG1.AA
encoded in pHuTIG1.AA:
DIQMTQSPSSLSASVGDRVTITCRASKSISKYLAWYQQKPGKAPKLLIYSGSTLQSGV
PSRFSGSGSGTDFTLTISSLQPEDFATYYCQQHNEYPWTFGGGTKVEIKRTVAAPSVFI
FPPSDEQLKSGTASVVCLLNNFYPREAKVQWKVDNALQSGNSQESVTEQDSKDSTY
SLSSTLTLSKADYEKHKVYACEVTHQGLSSPVTKSFNRGEC SEQ ID NO: 42: Amino acid sequence of the designed humanized TIG3 VH (HuTIG3 VH):
MNFGLRLIFLVLTLKGVNCEVQLVESGGGLVQPGGSLRLSCAASGFAFSDYDMSWV
RQAPGKGLEWVAYISDGGYNTYYPDTVKGRFTISRDNAKNSLYLQMNSLRAEDTAV
YYCARQILLRYYPDYWGQGTTVTVSS SEQ ID NO: 43: Amino acid sequence of the mature HuTIG3 VH:
EVQLVESGGGLVQPGGSLRLSCAASGFAFSDYDMSWVRQAPGKGLEWVAYISDGG
YNTYYPDTVKGRFTISRDNAKNSLYLQMNSLRAEDTAVYYCARQILLRYYFDYWGQ
GTTVTVSS SEQ ID NO: 44: Amino acid sequence of the designed humanized TIG3 VL (HuTIG3 VL):
MDSQAQVLMLLLLWVSGTCGDIQMTQSPSSLSASVGDRVTITCKSSQSLLYSSNQKN
YLAWYQQKPGKAPKLLIYWASTRESGVPSRFSGSGSGTDFTLTISSLQPEDFAVYYC
QQYHSYPWTFGGGTKVEIK SEQ ID NO: 45: Amino acid sequence of the mature HuTIG3 VL:
DIQMTQSPSSLSASVGDRVTITCKSSQSLLYSSNQKNYLAWYQQKPGKAPKLLIYWA
STRESGVPSRFSGSGSGTDFTLTISSLQPEDFAVYYCQQYHSYPWTFGGGTKVEIK SEQ ID NO: 46: Nucleotide sequence of the synthetic HuTIG3 VH gene in pHuTIG3.AA:
ACTAGTACCACCATGAACTTTGGGCTCAGATTGATTTTCCTTGTCCTTACTCTGAA
AGGCGTGAACTGTGAAGTCCAGCTCGTGGAGTCTGGGGGAGGCCTTGTGCAGCC
TGGAGGGTCCCTGAGACTCTCCTGTGCAGCCTCTGGATTCGCTTTCAGTGACTAT
GACATGTCTTGGGTTCGCCAGGCTCCTGGCAAGGGGCTGGAGTGGGTCGCATAC
ATTAGTGATGGCGGTTATAACACCTACTATCCAGACACTGTGAAGGGCCGATTCA
CCATCTCCAGAGACAATGCCAAGAACTCCCTGTACCTGCAAATGAACAGTCTGA
GGGCTGAGGACACAGCCGTCTATTACTGTGCAAGACAAATTCTGCTGCGGTACTA
CTTTGACTACTGGGGCCAAGGCACCACTGTCACAGTCTCCTCAGGTGAGTCCTTA
AAACAAGCTT SEQ ID NO: 47: Nucleotide sequence of the synthetic HuTIG3 VL gene in pHuTIG3.AA:
GCTAGCACCACCATGGATTCACAGGCCCAGGTTCTTATGCTGCTGCTGCTCTGGG
TTTCTGGAACCTGTGGGGACATTCAGATGACACAGTCTCCATCCTCCCTGTCTGC
CTCAGTTGGAGACAGGGTTACTATCACCTGCAAGTCCAGTCAGAGTCTTCTGTAT
AGTAGCAATCAAAAGAACTACTTGGCCTGGTACCAGCAGAAACCAGGGAAGGCT
CCTAAACTGCTGATTTACTGGGCATCCACTAGGGAATCTGGGGTCCCTAGTCGCT
TCTCAGGCAGTGGATCTGGGACAGATTTCACTCTCACCATCAGCAGTCTGCAGCC
TGAAGACTTCGCAGTTTATTACTGTCAGCAATATCATAGCTATCCCTGGACCTTC
GGCGGAGGCACCAAGGTGGAAATCAAACGTAAGTAGAATCCAAAGAATTC SEQ ID NO: 48: Amino acid sequence of the mature gamma heavy chain of HuTIG3-
IgG1.AA encoded in pHuTIG3.AA:
EVQLVESGGGLVQPGGSLRLSCAASGFAFSDYDMSWVRQAPGKGLEWVAYISDGG
YNTYYPDTVKGRFTISRDNAKNSLYLQMNSLRAEDTAVYYCARQILLRYYFDYWGQ
GTTVTVSSASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKVEPKSCDKT
HTCPPCPAPEAAGGPSVFLFPPKPKDTLMISRTPEVTCVVVDVSHEDPEVKFNWYVD
GVEVHNAKTKPREEQYNSTYRVVSVLTVLHQDWLNGKEYKCKVSNKALPAPIEKTI
SKAKGQPREPQVYTLPPSRDELTKNQVSLTCLVKGFYPSDIAVEWESNGQPENNYKT
TPPVLDSDGSFFLYSKLTVDKSRWQQGNVFSCSVMHEALHNHYTQKSLSLSPGK SEQ ID NO: 49: Amino acid sequence of the mature kappa light chain of HuTIG3-IgG1.AA
encoded in pHuTIG3.AA:
DIQMTQSPSSLSASVGDRVTITCKSSQSLLYSSNQKNYLAWYQQKPGKAPKLLIYWA
STRESGVPSRFSGSGSGTDFTLTISSLQPEDFAVYYCQQYHSYPWTFGGGTKVEIKRT
VAAPSVFIFPPSDEQLKSGTASVVCLLNNFYPREAKVQWKVDNALQSGNSQESVTEQ
DSKDSTYSLSSTLTLSKADYEKHKVYACEVTHQGLSSPVTKSFNRGEC SEQ ID NO: 50: Amino acid sequences of the extracellular region of human TIGIT with the
Q35A mutation:
MMTGTIETTGNISAEKGGSIILQCHLSSTTAQVTAVNWEQQDQLLAICNADLGWHISP
SFKDRVAPGPGLGLTLQSLTVNDTGEYFCIYHTYPDGTYTGRIFLEVLESSVAEHGAR
FQIPTG SEQ ID NO: 51: Amino acid sequences of the extracellular region of human TIGIT with the
N37A mutation:
MMTGTIETTGNISAEKGGSIILQCHLSSTTAQVTQVAWEQQDQLLAICNADLGWHISP
SFKDRVAPGPGLGLTLQSLTVNDTGEYFCIYHTYPDGTYTGRIFLEVLESSVAEHGAR
FQIPTG

| SEQUENCES |
|---|
| SEQ ID NO: 52: Amino acid sequences of the extracellular region of human TIGIT with the Q39A mutation:<br>MMTGTIETTGNISAEKGGSIILQCHLSSTTAQVTQVNWAQQD QLLAICNADLGWHIS<br>PSFKDRVAPGPGLGLTLQSLTVNDTGEYFCIYHTYPDGTYTGRIFLEVLESSVAEH GA<br>RFQIPTG |
| SEQ ID NO: 53: Amino acid sequences of the extracellular region of human TIGIT with the N49A mutation:<br>MMTGTIETTGNISAEKGGSIILQCHLSSTTAQVTQVNWEQQDQLLAICAADLGWHISP<br>SFKDRVAPGPGLGLTLQSLTVNDTGEYFCIYHTYPDGTYTGRIFLEVLESSVAEHGAR<br>FQIPTG |
| SEQ ID NO: 54: Amino acid sequences of the extracellular region of human TIGIT with the D51A mutation:<br>MMTGTIETTGNISAEKGGSIILQCHLSSTTAQVTQVNWEQQDQLLAICNAALGWHISP<br>SFKDRVAPGPGLGLTLQSLTVNDTGEYFCIYHTYPDGTYTGRIFLEVLESSVAEHGAR<br>FQIPTG |
| SEQ ID NO: 55: Amino acid sequences of the extracellular region of human TIGIT with the F86A mutation:<br>MMTGTIETTGNISAEKGGSIILQCHLSSTTAQVTQVNWEQQDQLLAICNADLGWHISP<br>SFKDRVAPGPGLGLTLQSLTVNDTGEYACIYHTYPDGTYTGRIFLEVLESSVAEHGAR<br>FQIPTG |
| SEQ ID NO: 56: Amino acid sequence of mature anti-human PD-L1 antibody heavy chain<br>EVQLVESGGGLVQPGGSLRLSCAASGFTFSDSWIHWVRQAPGKGLEWVAWISPYGG<br>STYYADSVKGRFTISADTSKNTAYLQMNSLRAEDTAVYYCARRHWPGGFDYWGQG<br>TLVTVSAASTKGPSVFPLAPSSKSTSGGTAALGCLVKDYFPEPVTVSWNSGALTSGV<br>HTFPAVLQSSGLYSLSSVVTVPSSSLGTQTYICNVNHKPSNTKVDKKVEPKSCDKTHT<br>CPPCPAPELLGGPSVFLFPPKPKDTLMISRTPEVTCVVVDVSHEDPEVKFNWYVDGV<br>EVHNAKTKPREEQYASTYRVVSVLTVLHQDWLNGKEYKCKVSNKALPAPIEKTISK<br>AKGQPREPQVYTLPPSRDELTKNQVSLTCLVKGFYPSDIAVEWESNGQPENNYKTTP<br>PVLDSDGSFFLYSKLTVDKSRWQQGNVFSCSVMHEALHNHYTQKSLSLSPG |
| SEQ ID NO: 57: Amino acid sequence of mature anti-human PD-L1 antibody light chain<br>DIQMTQSPSSLSASVGDRVTITCRASQDVSTAVAWYQQKPGKAPKLLIYSASFLYSG<br>VPSRFSGSGSGTDFTLTISSLQPEDFATYYCQQYLFTPPTFGQGTKVEIKRTVAAPSVFI<br>FPPSDEQLKSGTASVVCLLNNFYPREAKVQWKVDNALQSGNSQESVTEQDSKDSTY<br>SLSSTLTLSKADYEKHKVYACEVTHQGLSSPVTKSFNRGEC |
| SEQ ID NO: 58: Amino acid sequence of signal, HA tag and linker peptides fused to mature human TIGIT:<br>MRWCLLLIWAQGLRQAPLASGYPYDVPDYAGGGGSGGGGSMMTGTIETTGNISAE<br>KGGSIILQCHLSSTTAQVTQVNWEQQDQLLAICNADLGWHISPSFKDRVAPGPGLGL<br>TLQSLTVNDTGEYFCIYHTYPDGTYTGRIFLEVLESSVAEHGARFQIPLLGAMAATLV<br>VICTAVIVVVALTRKKKALRIHSVEGDLRRKSAGQEEWSPSAPSPPGSCVQAEAAPA<br>GLCGEQRGEDCAELHDYFNVLSYRSLGNCSFFTETG |
| SEQ ID NO: 59: Amino acid sequence of the extracellular region of human TIGIT fused to the Fc region of human immunoglobulin γ1 chain (hTIGIT-Fc):<br>MMTGTIETTGNISAEKGGSIILQCHLSSTTAQVTQVNWEQQDQLLAICNADLGWHISP<br>SFKDRVAPGPGLGLTLQSLTVNDTGEYFCIYHTYPDGTYTGRIFLEVLESSVAEHGAR<br>FQIPTGTGGGEPKSCDKTHTCPPCPAPELLGGPSVFLFPPKPKDTLMISRTPEVTCVVV<br>DVSHEDPEVKFNWYVDGVEVHNAKTKPREEQYNSTYRVVSVLTVLHQDWLNGKE<br>YKCKVSNKALPAPIEKTISKAKGQPREPQVYTLPPSRDELTKNQVSLTCLVKGFYPSD<br>IAVEWESNGQPENNYKTTPPVLDSDGSFFLYSKLTVDKSRWQQGNVFSCSVMHEAL<br>HNHYTQKSLSLSPGK |
| SEQ ID NO: 60: Amino acid sequence of the mature gamma heavy chain of HuTIG1-IgG1.Q:<br>EVQLVESGGGLVQPGGSLRLSCAASGFTFSNFGMHWVRQAPGKGLEWVAFISSGSSS<br>IYYADTVKGRFTISRDNAKNSLYLQMNSLRAEDTAVYYCARMRLDYYAMDYWGQ<br>GTMVTVSSASTKGPSVFPLAPSSKSTSGGTAALGCLVKDYFPEPVTVSWNSGALTSG<br>VHTFPAVLQSSGLYSLSSVVTVPSSSLGTQTYICNVNHKPSNTKVDKKVEPKSCDKT<br>HTCPPCPAPELLGGPSVFLFPPKPKDTLMISRTPEVTCVVVDVSHEDPEVKFNWYVD<br>GVEVHNAKTKPREEQYQSTYRVVSVLTVLHQDWLNGKEYKCKVSNKALPAPIEKTI<br>SKAKGQPREPQVYTLPPSRDELTKNQVSLTCLVKGFYPSDIAVEWESNGQPENNYKT<br>TPPVLDSDGSFFLYSKLTVDKSRWQQGNVFSCSVMHEALHNHYTQKSLSLSPGK |

| SEQUENCES |
|---|
| SEQ ID NO: 61: Amino acid sequence of the mature gamma heavy chain of HuTIG1-IgG4.P:<br>EVQLVESGGGLVQPGGSLRLSCAASGFTFSNFGMHWVRQAPGKGLEWVAFISSGSSSIY<br>YADTVKGRFTISRDNAKNSLYLQMNSLRAEDTAVYYCARMRLDYYAMDYWGQGT<br>MVTVSSASTKGPSVFPLAPCSRSTSESTAALGCLVKDYFPEPVTVSWNSGALTSGVH<br>TFPAVLQSSGLYSLSSVVTVPSSSLGTKTYTCNVDHKPSNTKVDKRVESKYGPPCPPC<br>PAPEFLGGPSVFLFPPKPKDTLMISRTPEVTCVVVDVSQEDPEVQFNWYVDGVEVHN<br>AKTKPREEQFNSTYRVVSVLTVLHQDWLNGKEYKCKVSNKGLPSSIEKTISKAKGQP<br>REPQVYTLPPSQEEMTKNQVSLTCLVKGFYPSDIAVEWESNGQPENNYKTTPPVLDS<br>DGSFFLYSRLTVDKSRWQEGNVFSCSVMHEALHNHYTQKSLSLSLGK<br><br>SEQ ID NO: 62: Amino acid sequence of the mature gamma heavy chain of HuTIG3-IgG1.Q:<br>EVQLVESGGGLVQPGGSLRLSCAASGFAFSDYDMSWVRQAPGKGLEWVAYISDGG<br>YNTYYPDTVKGRFTISRDNAKNSLYLQMNSLRAEDTAVYYCARQILLRYYFDYWGQ<br>GTTVTVSSASTKGPSVFPLAPSSKSTSGGTAALGCLVKDYFPEPVTVSWNSGALTSG<br>VHTFPAVLQSSGLYSLSSVVTVPSSSLGTQTYICNVNHKPSNTKVDKKVEPKSCDKT<br>HTCPPCPAPELLGGPSVFLFPPKPKDTLMISRTPEVTCVVVDVSHEDPEVKFNWYVD<br>GVEVHNAKTKPREEQYQSTYRVVSVLTVLHQDWLNGKEYKCKVSNKALPAPIEKTI<br>SKAKGQPREPQVYTLPPSRDELTKNQVSLTCLVKGFYPSDIAVEWESNGQPENNYKT<br>TPPVLDSDGSFFLYSKLTVDKSRWQQGNVFSCSVMHEALHNHYTQKSLSLSPGK<br><br>SEQ ID NO: 63: Amino acid sequence of the mature gamma heavy chain of HuTIG3-IgG4.P:<br>EVQLVESGGGLVQPGGSLRLSCAASGFAFSDYDMSWVRQAPGKGLEWVAYISDGG<br>YNTYYPDTVKGRFTISRDNAKNSLYLQMNSLRAEDTAVYYCARQILLRYYFDYWGQ<br>GTTVTVSSASTKGPSVFPLAPCSRSTSESTAALGCLVKDYFPEPVTVSWNSGALTSGV<br>HTFPAVLQSSGLYSLSSVVTVPSSSLGTKTYTCNVDHKPSNTKVDKRVESKYGPPCPP<br>CPAPEFLGGPSVFLFPPKPKDTLMISRTPEVTCVVVDVSQEDPEVQFNWYVDGVEVH<br>NAKTKPREEQFNSTYRVVSVLTVLHQDWLNGKEYKCKVSNKGLPSSIEKTISKAKGQ<br>PREPQVYTLPPSQEEMTKNQVSLTCLVKGFYPSDIAVEWESNGQPENNYKTTPPVLD<br>SDGSFFLYSRLTVDKSRWQEGNVFSCSVMHEALHNHYTQKSLSLSLGK<br><br>SEQ ID NO: 64: Amino acid sequence of the mature kappa light chain of HuTIG1-IgG1.Q and HuTIG1-IgG4.P:<br>DIQMTQSPSSLSASVGDRVTITCRASKSISKYLAWYQQKPGKAPKLLIYSGSTLQSGV<br>PSRFSGSGSGTDFTLTISSLQPEDFATYYCQQHNEYPWTFGGGTKVEIKRTVAAPSVFI<br>FPPSDEQLKSGTASVVCLLNNFYPREAKVQWKVDNALQSGNSQESVTEQDSKDSTY<br>SLSSTLTLSKADYEKHKVYACEVTHQGLSSPVTKSFNRGEC<br><br>SEQ ID NO: 65: Amino acid sequence of the mature kappa light chain of HuTIG3-IgG1.Q and HuTIG3-IgG4.P:<br>DIQMTQSPSSLSASVGDRVTITCKSSQSLLYSSNQKNYLAWYQQKPGKAPKLLIYWA<br>STRESGVPSRFSGSGSGTDFTLTISSLQPEDFAVYYCQQYHSYPWTFGGGTKVEIKRT<br>VAAPSVFIFPPSDEQLKSGTASVVCLLNNFYPREAKVQWKVDNALQSGNSQESVTEQ<br>DSKD STYSLSSTLTLSKADYEKHKVYACEVTHQGLSSPVTKSFNRGEC |

We claim:

1. A monoclonal antibody that binds to a TIGIT polypeptide, comprising a heavy chain CDR1 comprising the amino acid sequence of SEQ ID NO: 11, a heavy chain CDR2 comprising the amino acid sequence of SEQ ID NO: 12, a heavy chain CDR3 comprising the amino acid sequence of SEQ ID NO: 13, a light chain CDR1 comprising the amino acid sequence of SEQ ID NO: 15, a light chain CDR2 comprising the amino acid sequence of SEQ ID NO: 16, and a light chain CDR3 comprising the amino acid sequence of SEQ ID NO: 17.

2. The anti-TIGIT antibody of claim 1, comprising a mature heavy chain variable region with at least 90% sequence identity to SEQ ID NO:35 and a mature light chain variable region with at least 90% sequence identity to SEQ ID NO:37.

3. The anti-TIGIT antibody of claim 2, wherein the mature heavy chain variable region is linked to a heavy chain constant region comprising SEQ ID NO: 40 provided that the C-terminal lysine may or may not be present, and the mature light chain variable region is linked to a light chain constant region comprising SEQ ID NO: 41.

4. The anti-TIGIT antibody of claim 2, wherein the mature heavy chain variable region is linked to a heavy chain constant region comprising SEQ ID NO: 60 provided that the C-terminal lysine may or may not be present, and the mature light chain variable region is linked to a light chain constant region comprising SEQ ID NO: 64.

5. The anti-TIGIT antibody of claim 2, wherein the mature heavy chain variable region is linked to a heavy chain constant region comprising SEQ ID NO: 61 provided that the C-terminal lysine may or may not be present, and the mature light chain variable region is linked to a light chain constant region comprising SEQ ID NO: 64.

6. A monoclonal antibody that binds to a TIGIT polypeptide, comprising a heavy chain CDR1 comprising the amino acid sequence of SEQ ID NO: 11, a heavy chain CDR2 comprising the amino acid sequence of SEQ ID NO: 12, a heavy chain CDR3 comprising the amino acid sequence of SEQ ID NO: 13, a light chain CDR1 comprising the amino acid sequence of SEQ ID NO: 15, a light chain CDR2 comprising the amino acid sequence of SEQ ID NO: 16, and a light chain CDR3 comprising the amino acid sequence of SEQ ID NO: 17, wherein the antibody has one or more of the following properties:

(a) inhibits binding of TIGIT to CD155 optionally with an $IC_{50}$ of 15-100 ng/ml,
(b) increases intrinsic T-cell activation in the presence of antigen presenting cells expressing CD155 as measured by IL-2 production, optionally by 1.5-3 fold, as compared to intrinsic T-cell activation in the presence of antigen presenting cells expressing CD155 and in the absence of the antibody,
(c) increases antigen-specific T-cell activation as measured by IL-2 production, optionally by 1.5-3 fold, as compared to antigen-specific T-cell activation in the absence of the antibody,
(d) increases natural killer cell activation as measured by production of any of IL-2, IL-6, TNFα or IFNγ, optionally by 1.5-3 fold, as compared to natural killer cell activation in the absence of the antibody,
(e) increases T-cell production of at least one pro-inflammatory cytokine, optionally by 1.5-3 fold, as compared to T-cell production of the at least one pro-inflammatory cytokine in the absence of the antibody, and
(f) reduces T-cell production of a least one anti-inflammatory cytokine, optionally by 1.5-3 fold, as compared to T-cell production of the a least one anti-inflammatory cytokine in the absence of the antibody.

7. The anti-TIGIT antibody of claim 1, wherein the antibody is a, a chimeric antibody, a humanized antibody, or a veneered antibody.

8. The anti-TIGIT antibody of claim 1, wherein the antibody (1) has a human IgG1 kappa isotype; (2) has a human IgG4 kappa isotype; (3) is an intact antibody; or (4) is a (a) single-chain antibody, (b) Fab fragment, or (c) F(ab')2 fragment.

9. A pharmaceutical composition comprising an antibody according to claim 1 and a pharmaceutically acceptable carrier.

* * * * *

UNITED STATES PATENT AND TRADEMARK OFFICE
CERTIFICATE OF CORRECTION

| | |
|---|---|
| PATENT NO. | : 10,537,633 B2 |
| APPLICATION NO. | : 15/449665 |
| DATED | : January 21, 2020 |
| INVENTOR(S) | : J. Yun Tso et al. |

It is certified that error appears in the above-identified patent and that said Letters Patent is hereby corrected as shown below:

In the Specification

In Column 4, Lines 4-5, please replace "a heavy chain constant region comprising" with -- a heavy chain constant region, resulting in a heavy chain comprising --.

In Column 4, Lines 7-8, please replace "a light chain constant region comprising" with -- a light chain constant region, resulting in a light chain comprising --.

In Column 4, Lines 57-58, please replace "a heavy chain constant region comprising" with -- a heavy chain constant region, resulting in a heavy chain comprising --.

In Column 4, Lines 60-61, please replace "a light chain constant region comprising" with -- a light chain constant region, resulting in a light chain comprising --.

In Column 4, Line 63, please replace "a heavy chain constant region comprising" with -- a heavy chain constant region, resulting in a heavy chain comprising --.

In Column 4, Line 66, please replace "a light chain constant region comprising" with -- a light chain constant region, resulting in a light chain comprising --.

In Column 5, Lines 1-2, please replace "a heavy chain constant region comprising" with -- a heavy chain constant region, resulting in a heavy chain comprising --.

In Column 5, Lines 4-5, please replace "a light chain constant region comprising" with -- a light chain constant region, resulting in a light chain comprising --.

In Column 5, Lines 18-19, please replace "a heavy chain constant region comprising" with -- a heavy chain constant region, resulting in a heavy chain comprising --.

Signed and Sealed this
Tenth Day of June, 2025

Coke Morgan Stewart
*Acting Director of the United States Patent and Trademark Office*

CERTIFICATE OF CORRECTION (continued)
U.S. Pat. No. 10,537,633 B2

In Column 5, Lines 21-22, please replace "a light chain constant region comprising" with -- a light chain constant region, resulting in a light chain comprising --.

In Column 5, Line 24, please replace "a heavy chain constant region comprising" with -- a heavy chain constant region, resulting in a heavy chain comprising --.

In Column 5, Line 27, please replace "a light chain constant region comprising" with -- a light chain constant region, resulting in a light chain comprising --.

In Column 5, Lines 29-30, please replace "a heavy chain constant region comprising" with -- a heavy chain constant region, resulting in a heavy chain comprising --.

In Column 5, Lines 32-33, please replace "a light chain constant region comprising" with -- a light chain constant region, resulting in a light chain comprising --.

In Column 17, Lines 65-66, please replace "a heavy chain constant region consisting" with -- a heavy chain constant region, resulting in a heavy chain consisting --.

In Column 18, Lines 1-2, please replace "a light chain constant region consisting" with -- a light chain constant region, resulting in a light chain consisting --.

In Column 18, Lines 19-20, please replace "a heavy chain constant region consisting" with -- a heavy chain constant region, resulting in a heavy chain consisting --.

In Column 18, Line 23, please replace "a light chain constant region consisting" with -- a light chain constant region, resulting in a light chain consisting --.

In the Claims

In Claim 3, Column 121, Lines 63-64, please replace "a heavy chain constant region comprising" with -- a heavy chain constant region, resulting in a heavy chain comprising --.

In Claim 3, Column 121, Lines 66-67, please replace "a light chain constant region comprising" with -- a light chain constant region, resulting in a light chain comprising --.

In Claim 4, Column 122, Lines 46-47, please replace "a heavy chain constant region comprising" with -- a heavy chain constant region, resulting in a heavy chain comprising --.

In Claim 4, Column 122, Lines 49-50, please replace "a light chain constant region comprising" with -- a light chain constant region, resulting in a light chain comprising --.

In Claim 5, Column 122, Lines 52-53, please replace "a heavy chain constant region comprising" with -- a heavy chain constant region, resulting in a heavy chain comprising --.

In Claim 5, Column 122, Lines 55-56, please replace "a light chain constant region comprising" with -- a light chain constant region, resulting in a light chain comprising --.